(12) United States Patent
Hinga et al.

(10) Patent No.: US 9,994,862 B2
(45) Date of Patent: Jun. 12, 2018

(54) RICE RESISTANT TO HPPD AND ACCASE INHIBITING HERBICIDES

(71) Applicant: RICETEC, INC., Houston, TX (US)

(72) Inventors: Melissa Hinga, League City, TX (US); Melissa Shannon Moon, Pearland, TX (US); Venu Reddyvari Channarayappa, Friendswood, TX (US); Russell D. Rasmussen, League City, TX (US); Federico Cuevas, League City, TX (US)

(73) Assignee: RiceTec, Inc., Alvin, TX (US)

( * ) Notice: Subject to any disclaimer, the term of this patent is extended or adjusted under 35 U.S.C. 154(b) by 0 days. days.

(21) Appl. No.: 15/051,440

(22) Filed: Feb. 23, 2016

(65) Prior Publication Data
US 2016/0319298 A1 Nov. 3, 2016

Related U.S. Application Data

(63) Continuation of application No. 14/465,242, filed on Aug. 21, 2014, now Pat. No. 9,303,270, which is a continuation-in-part of application No. 13/975,034, filed on Aug. 23, 2013, and a continuation-in-part of application No. 13/554,675, filed on Jul. 20, 2012, now Pat. No. 9,370,149.

(60) Provisional application No. 61/869,608, filed on Aug. 23, 2013, provisional application No. 61/692,861, filed on Aug. 24, 2012, provisional application No. 61/510,585, filed on Jul. 22, 2011, provisional application No. 61/541,832, filed on Sep. 30, 2011.

(51) Int. Cl.
| | |
|---|---|
| A01H 5/10 | (2018.01) |
| A01H 1/04 | (2006.01) |
| C12N 15/82 | (2006.01) |
| A01N 41/10 | (2006.01) |
| A01N 43/60 | (2006.01) |
| C12N 9/00 | (2006.01) |
| C07K 14/415 | (2006.01) |
| C12N 9/02 | (2006.01) |

(52) U.S. Cl.
CPC ......... *C12N 15/8274* (2013.01); *A01H 1/04* (2013.01); *A01H 5/10* (2013.01); *A01N 41/10* (2013.01); *A01N 43/60* (2013.01); *C07K 14/415* (2013.01); *C12N 9/0069* (2013.01); *C12N 9/93* (2013.01); *C12Y 113/11027* (2013.01); *C12Y 604/01002* (2013.01)

(58) Field of Classification Search
CPC .................. A01H 5/10; C12N 15/8274; C12Y 604/01002; C12Y 113/11027
See application file for complete search history.

(56) References Cited

U.S. PATENT DOCUMENTS

| | | |
|---|---|---|
| 4,443,971 A | 4/1984 | Chaleff |
| 5,290,696 A | 3/1994 | Somers et al. |
| 5,428,001 A | 6/1995 | Somers et al. |
| 5,539,092 A | 7/1996 | Haselkorn et al. |
| 5,736,629 A | 4/1998 | Croughan |
| 5,756,290 A | 5/1998 | Haselkorn et al. |
| 5,767,373 A | 6/1998 | Ward et al. |
| 5,786,513 A | 7/1998 | Schulz |
| 5,792,627 A | 8/1998 | Haselkorn et al. |
| 5,801,233 A | 9/1998 | Haselkorn et al. |
| 5,910,626 A | 6/1999 | Haselkorn et al. |
| 5,939,602 A | 8/1999 | Volrath et al. |
| 5,972,644 A | 10/1999 | Haselkorn et al. |
| 5,990,046 A | 11/1999 | Fenderson et al. |
| 6,066,779 A | 5/2000 | Yan |
| 6,069,298 A | 5/2000 | Gengenbach et al. |
| 6,084,155 A | 7/2000 | Volrath et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,281,168 B1 | 8/2001 | Shaner et al. |
| 6,282,837 B1 | 9/2001 | Ward et al. |
| 6,288,306 B1 | 9/2001 | Ward et al. |
| 6,308,458 B1 | 10/2001 | Volrath et al. |
| 6,399,342 B1 | 6/2002 | Haselkorn et al. |
| 6,448,476 B1 | 9/2002 | Barry |
| 6,455,688 B1 | 9/2002 | Slabas et al. |
| 6,727,414 B2 | 4/2004 | Moldenhauer et al. |
| 6,808,904 B2 | 10/2004 | Ward et al. |
| 6,870,075 B1 | 3/2005 | Beetham et al. |
| 6,911,589 B2 | 6/2005 | Johnson |
| 6,943,280 B2 | 9/2005 | Croughan |

(Continued)

FOREIGN PATENT DOCUMENTS

| | | | |
|---|---|---|---|
| CA | 2823290 | 5/2012 | |
| CN | 101595886 A | * 12/2009 | ............. A01N 47/36 |

(Continued)

OTHER PUBLICATIONS

Délye, Christophe, Marie Jasieniuk, and Valerie Le Corre. "Deciphering the evolution of herbicide resistance in weeds." Trends in Genetics 29.11 (2013): 649-658.*

(Continued)

*Primary Examiner* — Lee A Visone
*Assistant Examiner* — Weihua Fan
(74) *Attorney, Agent, or Firm* — Barnes & Thornburg LLP; Alice O. Martin

(57) ABSTRACT

Rice is described that is tolerant/resistant to a plurality of herbicides, for example, ACCase and HPPD inhibitors. Use of the rice for weed control and methods of producing tolerant/resistant rice are also described.

4 Claims, 27 Drawing Sheets

(56) References Cited

U.S. PATENT DOCUMENTS

| | | | |
|---|---|---|---|
| 6,953,881 B2 | 10/2005 | Tillman | |
| 6,956,154 B2 | 10/2005 | Xie | |
| 7,005,567 B2 | 2/2006 | Tillman | |
| 7,094,606 B2 | 8/2006 | Arntzen et al. | |
| 7,141,726 B2 | 11/2006 | Moldenhauer et al. | |
| 7,253,347 B2 | 8/2007 | Linscombe | |
| 7,301,083 B2 | 11/2007 | Sarreal et al. | |
| 7,304,223 B2 | 12/2007 | Sarreal et al. | |
| 7,345,221 B2 | 3/2008 | Croughan | |
| 7,351,891 B2 | 4/2008 | Sarreal et al. | |
| 7,351,892 B2 | 4/2008 | Sarreal et al. | |
| 7,351,893 B2 | 4/2008 | Sarreal et al. | |
| 7,399,905 B2 | 7/2008 | Croughan | |
| 7,429,697 B2 | 9/2008 | Moldenhauer et al. | |
| 7,485,784 B2 | 2/2009 | Sarreal et al. | |
| 7,579,531 B2 | 8/2009 | Jodari | |
| 7,612,269 B2 | 11/2009 | Jodari | |
| 7,622,661 B2 | 11/2009 | Johnson | |
| 7,642,434 B2 | 1/2010 | Moldenhauer | |
| 7,642,435 B2 | 1/2010 | Sarreal et al. | |
| 7,671,254 B2 | 3/2010 | Tranel et al. | |
| 7,687,690 B2 | 3/2010 | Johnson et al. | |
| 7,754,947 B2 | 7/2010 | Croughan | |
| 7,786,360 B2 | 8/2010 | Linscombe | |
| 7,803,991 B2 | 9/2010 | Daniell | |
| 7,820,883 B2 | 10/2010 | Walsh et al. | |
| 7,838,733 B2 | 11/2010 | Wright et al. | |
| 7,842,856 B2 | 11/2010 | Tranel et al. | |
| H2258 H | 6/2011 | Arnevik et al. | |
| 7,973,083 B2 | 7/2011 | Clemens et al. | |
| 8,071,847 B2 | 12/2011 | Walsh et al. | |
| 8,088,979 B2 | 1/2012 | Walsh et al. | |
| 8,097,774 B2 | 1/2012 | Hawkes et al. | |
| 8,106,276 B2 | 1/2012 | Luo | |
| 8,134,058 B2 | 3/2012 | Moldenhauer | |
| 8,153,870 B2 | 4/2012 | Re et al. | |
| 8,268,622 B2 | 9/2012 | Gocal et al. | |
| 8,283,536 B1 | 10/2012 | Re et al. | |
| 8,283,537 B1 | 10/2012 | Re et al. | |
| 8,288,635 B2 | 10/2012 | Moldenhauer | |
| 8,449,917 B2 | 5/2013 | Dave et al. | |
| 8,598,080 B2 | 12/2013 | Linscombe | |
| 8,771,959 B2 | 7/2014 | Andrews et al. | |
| 8,796,177 B2 | 8/2014 | Mann et al. | |
| 8,841,233 B2 | 9/2014 | Yerkes et al. | |
| 8,847,017 B2 | 9/2014 | Poree et al. | |
| 8,847,018 B2 | 9/2014 | Poree et al. | |
| 8,853,495 B2 | 10/2014 | Poree et al. | |
| 8,853,496 B2 | 10/2014 | Poree et al. | |
| 8,859,856 B2 | 10/2014 | Poree et al. | |
| 2001/0031704 A1* | 10/2001 | Hacker | A01N 57/20 504/127 |
| 2004/0107465 A1 | 6/2004 | Tillman et al. | |
| 2004/0123343 A1 | 6/2004 | La Rosa et al. | |
| 2007/0074303 A1 | 3/2007 | McCutchen et al. | |
| 2008/0256668 A1 | 10/2008 | Beetham et al. | |
| 2008/0300139 A1 | 12/2008 | Zawierucha et al. | |
| 2009/0093366 A1* | 4/2009 | Wright | C12N 9/0069 504/142 |
| 2009/0165166 A1 | 6/2009 | Feng et al. | |
| 2009/0235395 A1 | 9/2009 | Arntzen et al. | |
| 2009/0240073 A1 | 9/2009 | Barry | |
| 2010/0029485 A1* | 2/2010 | Livore | C12N 9/1022 504/241 |
| 2010/0048405 A1 | 2/2010 | Raymer et al. | |
| 2010/0197503 A1* | 8/2010 | Hawkes | C12N 9/0069 504/348 |
| 2010/0293628 A1 | 11/2010 | Tuinstra et al. | |
| 2011/0028324 A1 | 2/2011 | Cordingley et al. | |
| 2011/0124503 A1 | 5/2011 | Wright et al. | |
| 2011/0214196 A1 | 9/2011 | Raymer et al. | |
| 2012/0021913 A1 | 1/2012 | James et al. | |
| 2012/0284812 A1 | 11/2012 | Mankin et al. | |
| 2012/0284853 A1 | 11/2012 | Mankin et al. | |
| 2013/0019349 A1 | 1/2013 | Gocal et al. | |
| 2013/0023416 A1 | 1/2013 | Hinga et al. | |
| 2013/0111618 A1 | 5/2013 | Mankin et al. | |
| 2014/0024530 A1 | 1/2014 | Poree et al. | |
| 2014/0045686 A1 | 2/2014 | Mankin et al. | |
| 2014/0059721 A1 | 2/2014 | Hinga et al. | |
| 2014/0250543 A1 | 9/2014 | Ostlie et al. | |
| 2014/0274710 A1 | 9/2014 | Mann et al. | |

FOREIGN PATENT DOCUMENTS

| | | |
|---|---|---|
| EP | 2453012 | 5/2012 |
| WO | WO 95/29246 | 11/1995 |
| WO | WO 98/54330 | 12/1998 |
| WO | WO 2009/034188 | 3/2009 |
| WO | WO 2010/040485 | 4/2010 |
| WO | WO 2010/046437 | 4/2010 |
| WO | WO 2011/028832 | 3/2011 |
| WO | WO 2011/028833 | 3/2011 |
| WO | WO 2011/028836 | 3/2011 |
| WO | WO 2013/016210 | 1/2013 |
| WO | WO 2015/025031 | 2/2015 |

OTHER PUBLICATIONS

Rogue—A Novel Herbicide for US Rice Production, Louisiana Agricultural Technology and Management Conference, Feb. 18, 2016.*

Chen et al, "Genome-wide association analyses provide genetic and biochemical insights into natural variation in rice metabolism," *Nature Genetics*, 46: 714-721 (2014).

Oryza sativa acetyl-coenzyme A carboxylase mutant G2107S, Database Geneseq [Online], accession No. AZG28702, Apr. 28, 2001.

Sekino et al., "Herbicidal activity of a new paddy bleaching herbicide, benzobicyclon," *J. Pest. Sci.*, 33(4): 364-370 (2008).

Abe et al., "Genome sequencing reveals agronomically important loci in rice using MutMap," *Nat. Biotech.*, 30, 174-178 (2012).

Cruz-Hipolito et al., "Resistance mechanism to acetyl coenzyme A carboxylase inhibiting herbicides in Phalaris paradoxa collected in Mexican wheat fields," *Plant Soil*, 355:121-130 (2012).

Délye et al, "'Universal' primers for PCR-sequencing of grass chloroplastic acetyl-CoA carboxylase domains involved in resistance to herbicides," Weed Research, 45:323-330 (2005).

Délye et al., "An Isoleucine Residue within the Carboxyl-Transferase Domain of Multidomain Acetyl-Coenzyme A Carboxylase is a Major Determinant of Sensitivity to Aryloxyphenoxypropionate but not to Cyclohexanedione Inhibitors," Plant Physiology, 132: 1716-1723 (2003).

Délye et al., "Molecular Bases for Sensitivity to Acetyl-Coenzyme A Carboxylase Inhibitors in Black-Grass," Plant Physiology, 137: 794-806 (2005).

Guo et al., "Protein tolerance to random amino acid change," Proc. Natl. Acad. Sci. USA 101: 9205-9210 (2004).

Jain, "Tissue culture-derived variation in crop improvement," Euphytica, 118:153-166 (2001).

Liu et al., "Single-Site Mutations in the Carboxyltransferase Domain of Plastid Acetyl-CoA Carboxylase Confer Resistance to Grass-Specific Herbicides," PNAS, 104(9): 3627-3632 (2007).

Martins et al., "Alleles Contributing to ACCase-Resistance in an Italian Ryegrass (*Lolium perenne* ssp. *multiflorum*) Population from Oregon," Weed Science, 62:468-473 (2014).

Matringe et al., "p-Hydroxyphenylpyruvate dioxygenase inhibitor-resistant plants," Pest. Manage. Sci., 61:269-276 (2005).

Okuzaki, A., and K. Toriyama. "Chimeric RNA/DNA oligonucleotide-directed gene targeting in rice." Plant cell reports 22.7 (2004): 509-512.

Ostlie et al., "Development and characterization of mutant winter wheat (*Triticum aestivum* L.) accessions resistant to the herbicide quizalofop," Theor. Appl. Genet., 128:343-351 (2015).

Ouyang et al., "The TIGR Rice Genome Annotation Resource: improvements and new features," Nucleic Acid Research, 35 Database Issue: D846-851 (Jan. 1, 2007).

Ruiz-Santaella et al., Detection of a new mutation of glycine to serine in the ACCase of a resistant biotype of Phalaris paradoxa. In:

(56) References Cited

OTHER PUBLICATIONS

Annual Meeting of the Weed Science Society of America, Abstracts, New York: WSSA, 46:93 (2006).
Rutger et al., "Registration of nine indica germplasms of rice," Crop Sci., 45:1170-1171 (2005).
Suzuki et al., "MNU-induced mutant pools and high performance TILLING enable finding of any gene mutation in rice," Mol. Genet. Genomics, 279:213-223 (2008).
Zhu et al., "Computational Simulations of the Interactions between Acetyl-Coenzyme-A Carboxylase and Clodinafop: Resistance Mechanism Due to Active and Nonactive Site Mutations," J. Chem. Inf. Model, 49(8): 1936-1943 (2009).
Delye et al., "Cross-resistance patterns to ACCase-inhibiting herbicides conferred by mutant ACCase isoforms in *Alopecurus myosuroides Huds*. (black-grass), re-examined at the recommend herbicide field rate," *Pest Management Science*, 64(11): 1179-86 (2008).
Scarabel et al., "Allelic variation of the ACCase gene and response to ACCase-inhibiting herbicides in pinoxaden-resistant *Lolium* spp.," *Pest Management Science*, 67(8): 932-941 (2011).
Zhu et al., The resistance mechanism research of ACCase inhibitor, *Journal of Huazhong Normal University Natural Sciences*, 43(1): 76-82 (2009).
Office Action issued in App. No. CN201280036348.5 (dated 2017).
Collavo, "Resistance to graminicides in monocotyledons weeds, Case studies of *Lolium* spp. and *Phalaris paradoxa* in Italy," Ph.D. Dissertation, University of Padova (2008).
UniProt Accession No. A2Y2U1.
Yu et al., "Diversity of Acetyl-Coenzyme a Carboxylase Mutations in Resistant *Lolium* Populations: Evaluation Using Clethodim$^{1[O4]}$," *Plant Physiology*, 145: 547-558 (2007).
Search Report and Written Opinion issued in App. No. PCT/EP17/69865 (dated Oct. 10, 2017).
Examination Report issued in App. No. PH 1-2014-500183 (Jan. 8, 2018).
Anyszka et al., "The Response of Snap Bean and Barnyardgrass (Echinochloa Crus-Galli) on quizalofop-P-Tefuryl," Vegetable Crops Research Bulletin, 51:95-102 (1999) (Abstract).
Maneechote et al., "Controlling invasive wild rice with ACCase-inhibiting herbicides," Proceedings of the 4th Intl Crop Science Congress, Brisbane, Australia (2004).
Maneechote et al., "Resistance to ACCase-inhibiting herbicides in sprangletop (*Leptochloa chinensis*)," Weed Science, 53:290-295 (2005).

\* cited by examiner

| Source Name | Notes | id20203988 | id20204054 | id20204500 | id20204125 | id20204163 | id20204200 | id20204245 | id20204316 | id20204396 | id20204418 | id20204446 | id20204457 | id20204489 | id20204583 | id20204617 | id20204662 |
|---|---|---|---|---|---|---|---|---|---|---|---|---|---|---|---|---|---|
| 76266 | L-031 | R0146 | R0146 | R0146 | P1003 | P1003 | P1003 | P1003 | P1003 | P1003 | P1003 | P1003 | P1003 | P1003 | P1003 | P1003 | P1003 |
| 76139 | L-051 | R0146 | R0146 | R0146 | R0146 | R0146 | P1003 | P1003 | P1003 | P1003 | P1003 | P1003 | P1003 | P1003 | P1003 | P1003 | P1003 |
| 76401 | Additional Plant-1 | R0146 | R0146 | R0146 | R0146 | R0146 | R0146 | P1003 | P1003 | P1003 | P1003 | P1003 | P1003 | P1003 | P1003 | P1003 | P1003 |
| 76253 | L-031 | R0146 | R0146 | R0146 | R0146 | R0146 | R0146 | R0146 | P1003 | P1003 | P1003 | P1003 | P1003 | P1003 | P1003 | P1003 | P1003 |
| 76411 | Additional Plant-1 | R0146 | R0146 | R0146 | R0146 | R0146 | R0146 | R0146 | R0146 | P1003 | P1003 | P1003 | P1003 | P1003 | P1003 | P1003 | P1003 |
| 76247 | L-031 | R0146 | R0146 | R0146 | R0146 | R0146 | R0146 | R0146 | R0146 | R0146 | P1003 | P1003 | P1003 | P1003 | P1003 | P1003 | P1003 |
| 76258 | L-031 | R0146 | R0146 | R0146 | R0146 | R0146 | R0146 | R0146 | R0146 | R0146 | R0146 | R0146 | P1003 | P1003 | P1003 | P1003 | P1003 |
| 76400 | Additional Plant-1 | R0146 | R0146 | R0146 | R0146 | R0146 | R0146 | R0146 | R0146 | R0146 | R0146 | R0146 | R0146 | R0146 | P1003 | P1003 | P1003 |
| 76132 | L-051 | P1003 | P1003 | P1003 | P1003 | P1003 | P1003 | P1003 | P1003 | P1003 | P1003 | P1003 | P1003 | R0146 | R0146 | R0146 | R0146 |
| 76417 | Additional Plant-1 | P1003 | P1003 | P1003 | P1003 | P1003 | P1003 | P1003 | P1003 | P1003 | P1003 | R0146 | R0146 | R0146 | R0146 | R0146 | R0146 |
| 76158 | L-051 | P1003 | P1003 | P1003 | P1003 | P1003 | P1003 | P1003 | P1003 | P1003 | R0146 | R0146 | R0146 | R0146 | R0146 | R0146 | R0146 |
| 76149 | L-051 | P1003 | P1003 | P1003 | P1003 | P1003 | P1003 | P1003 | R0146 | R0146 | R0146 | R0146 | R0146 | R0146 | R0146 | R0146 | R0146 |
| 76194 | L-031 | P1003 | P1003 | P1003 | P1003 | P1003 | P1003 | P1003 | R0146 | R0146 | R0146 | R0146 | R0146 | R0146 | R0146 | R0146 | R0146 |
| 76133 | L-051 | P1003 | P1003 | P1003 | P1003 | P1003 | P1003 | P1003 | R0146 | R0146 | R0146 | R0146 | R0146 | R0146 | R0146 | R0146 | R0146 |
| 76311 | Plant-061 | P1003 | P1003 | P1003 | P1003 | P1003 | P1003 | P1003 | P1003 | R0146 | R0146 | R0146 | R0146 | R0146 | R0146 | R0146 | R0146 |
| 76134 | L-051 | P1003 | P1003 | P1003 | P1003 | P1003 | P1003 | P1003 | R0146 | R0146 | R0146 | R0146 | R0146 | R0146 | R0146 | R0146 | R0146 |
| 76177 | L-031 | P1003 | P1003 | P1003 | P1003 | P1003 | P1003 | P1003 | R0146 | R0146 | R0146 | R0146 | R0146 | R0146 | R0146 | R0146 | R0146 |

FIG. 17

```
NIPPONBARE.TXT   CCTGTTCTGCTAGGAATAATAGAACTACATACTGCTATGATTTTCCACTGGTGAGTTGAC
R0146.TXT        CCTGTTCTGCTAGGAATAATAGAACTACATACTGCTATGATTTTCCACTGGTGAGTTGAC
09PM72399.TXT    CCTGTTCTGCTAGGAATAATAGAACTACATACTGCTATGATTTTCCACTGGTGAGTTGAC

NIPPONBARE.TXT   TGCTCCCTTATATTCAATGCATTACCATAGCAAATTCATATTCGTTCATGTTGTCAAAAT
R0146.TXT        TGCTCCCTTATATTCAATGCATTACCATAGCAAATTCATATTCGTTCATGTTGTCAAAAT
09PM72399.TXT    TGCTCCCTTATATTCAATGCATTACCATAGCAAATTCATATTCGTTCATGTTGTCAAAAT

NIPPONBARE.TXT   AAGCCGATGAAAATTCAAAACTGTAGGCATTTGAAACTGCAGTGAGGAAGTCATGGTCCT
R0146.TXT        AAGCCGATGAAAATTCAAAACTGTAGGCATTTGAAACTGCAGTGAGGAAGTCATGGTCCT
09PM72399.TXT    AAGCCGATGAAAATTCAAAACTGTAGGCATTTGAAACTGCAGTGAGGAAGTCATGGTCCT

NIPPONBARE.TXT   CTAGTACCTCTGGTGCTTCTAAAGGTGTTGAAAATGCCCAATGTTATGTTAAAGCTACAG
R0146.TXT        CTAGTACCTCTGGTGCTTCTAAAGGTGTTGAAAATGCCCAATGTTATGTTAAAGCTACAG
09PM72399.TXT    CTAGTACCTCTGGTGCTTCTAAAGGTGTTGAAAATGCCCAATGTTATGTTAAAGCTACAG

NIPPONBARE.TXT   AGTTGGTATTTGCGGACAAACATGGGTCATGGGGCACTCCTTTAGTTCAAATGGACCGGC
R0146.TXT        AGTTGGTATTTGCGGACAAACATGGGTCATGGGGCACTCCTTTAGTTCAAATGGACCGGC
09PM72399.TXT    AGTTGGTATTTGCGGACAAACATGGGTCATGGGGCACTCCTTTAGTTCAAATGGACCGGC

NIPPONBARE.TXT   CTGCTGGGCTCAATGACATTGGTATGGTAGCTTGGACCTTGAAGATGTCCACTCCTGAAT
R0146.TXT        CTGCTGGGCTCAATGACATTGGTATGGTAGCTTGGACCTTGAAGATGTCCACTCCTGAAT
09PM72399.TXT    CTGCTGGGCTCAATGACATTGGTATGGTAGCTTGGACCTTGAAGATGTCCACTCCTGAAT

NIPPONBARE.TXT   TTCCTAGTGGTAGGGAGATTATTGTTGTTGCAAATGATATTACGTTCAGAGCTGGATCAT
R0146.TXT        TTCCTAGTGGTAGGGAGATTATTGTTGTTGCAAATGATATTACGTTCAGAGCTGGATCAT
09PM72399.TXT    TTCCTAGTGGTAGGGAGATTATTGTTGTTGCAAATGATATTACGTTCAGAGCTGGATCAT

NIPPONBARE.TXT   TTGGCCCAAGGGAAGATGCATTTTTTGAAGCTGTTACCAACCTAGCCTGTGAGAAGAAAC
R0146.TXT        TTGGCCCAAGGGAAGATGCATTTTTTGAAGCTGTTACCAACCTAGCCTGTGAGAAGAAAC
09PM72399.TXT    TTGGCCCAAGGGAAGATGCATTTTTTGAAGCTGTTACCAACCTAGCCTGTGAGAAGAAAC

NIPPONBARE.TXT   TTCCTCTTATTTATTTGGCAGCAAATTCTGGTGCTCGAATTGGCATAGCAGATGAAGTGA
R0146.TXT        TTCCTCTTATTTATTTGGCAGCAAATTCTGGTGCTCGAATTGGCATAGCAGATGAAGTGA
09PM72399.TXT    TTCCTCTTATTTATTTGGCAGCAAATTCTGGTGCTCGAATTGGCATAGCAGATGAAGTGA

NIPPONBARE.TXT   AATCTTGCTTCCGTGTTGGGTGGTCTGATGATGGCAGCCCTGAACGTGGGTTTCAGTACA
R0146.TXT        AATCTTGCTTCCGTGTTGGGTGGTCTGATGATGGCAGCCCTGAACGTGGGTTTCAGTACA
09PM72399.TXT    AATCTTGCTTCCGTGTTGGGTGGTCTGATGATGGCAGCCCTGAACGTGGGTTTCAGTACA

NIPPONBARE.TXT   TTTATCTAAGCGAAGAAGACTATGCTCGTATTGGCACTTCTGTCATAGCACATAAGATGC
R0146.TXT        TTTATCTAAGCGAAGAAGACTATGCTCGTATTGGCACTTCTGTCATAGCACATAAGATGC
09PM72399.TXT    TTTATCTAAGCGAAGAAGACTATGCTCGTATTGGCACTTCTGTCATAGCACATAAGATGC

NIPPONBARE.TXT   AGCTAGACAGTGGTGAAATTAGGTGGGTTATTGATTCTGTTGTGGGCAAGGAAGATGGAC
R0146.TXT        AGCTAGACAGTGGTGAAATTAGGTGGGTTATTGATTCTGTTGTGGGCAAGGAAGATGGAC
09PM72399.TXT    AGCTAGACAGTGGTGAAATTAGGTGGGTTATTGATTCTGTTGTGGGCAAGGAAGATGGAC
```

FIG. 20

```
NIPPONBARE.TXT    TTGGTGTGGAGAATATACATGGAAGTGCTGCTATTGCCAGTGCTTATTCTAGGGCATATA
R0146.TXT         TTGGTGTGGAGAATATACATGGAAGTGCTGCTATTGCCAGTGCTTATTCTAGGGCATATA
09PM72399.TXT     TTGGTGTGGAGAATATACATGGAAGTGCTGCTATTGCCAGTGCTTATTCTAGGGCATATA

NIPPONBARE.TXT    AGGAGACATTTACACTTACATTTGTGACTGGAAGAACTGTTGGAATAGGAGCTTATCTTG
R0146.TXT         AGGAGACATTTACACTTACATTTGTGACTGGAAGAACTGTTGGAATAGGAGCTTATCTTG
09PM72399.TXT     AGGAGACATTTACACTTACATTTGTGACTGGAAGAACTGTTGGAATAGGAGCTTATCTTG

NIPPONBARE.TXT    CTCGACTTGGCATCCGGTGCATACAGCGTCTTGACCAGCCTATTATTCTTACAGGCTATT
R0146.TXT         CTCGACTTGGCATCCGGTGCATACAGCGTCTTGACCAGCCTATTATTCTTACAGGCTATT
09PM72399.TXT     CTCGACTTGGCATCCGGTGCATACAGCGTCTTGACCAGCCTATTATTCTTACAGGCTATT

NIPPONBARE.TXT    CTGCACTGAACAAGCTTCTTGGGCGGGAAGTGTACAGCTCCCACATGCAGTTGGGTGGTC
R0146.TXT         CTGCACTGAACAAGCTTCTTGGGCGGGAAGTGTACAGCTCCCACATGCAGTTGGGTGGTC
09PM72399.TXT     CTGCACTGAACAAGCTTCTTGGGCGGGAAGTGTACAGCTCCCACATGCAGTTGGGTGGTC

NIPPONBARE.TXT    CCAAAATCATGGCAACTAATGGTGTTGTCCATCTTACTGTTTCAGATGACCTTGAAGGCG
R0146.TXT         CCAAAATCATGGCAACTAATGGTGTTGTCCATCTTACTGTTTCAGATGACCTTGAAGGCG
09PM72399.TXT     CCAAAATCATGGCAACTAATGGTGTTGTCCATCTTACTGTTTCAGATGACCTTGAAGGCG

NIPPONBARE.TXT    TTTCTAATATATTGAGGTGGCTCAGTTATGTTCCTGCCTACATTGGTGGACCACTTCCAG
R0146.TXT         TTTCTAATATATTGAGGTGGCTCAGTTATGTTCCTGCCTACATTGGTGGACCACTTCCAG
09PM72399.TXT     TTTCTAATATATTGAGGTGGCTCAGTTATGTTCCTGCCTACATTGGTGGACCACTTCCAG

NIPPONBARE.TXT    TAACAACACCGTTGGACCCACCGGACAGACCTGTTGCATACATTCCTGAGAACTCGTGTG
R0146.TXT         TAACAACACCGTTGGACCCACCGGACAGACCTGTTGCATACATTCCTGAGAACTCGTGTG
09PM72399.TXT     TAACAACACCGTTGGACCCACCGGACAGACCTGTTGCATACATTCCTGAGAACTCGTGTG

NIPPONBARE.TXT    ATCCTCGAGCGGCTATCCGTGGTGTTGATGACAGCCAAGGGAAATGGTTAGGTGGTATGT
R0146.TXT         ATCCTCGAGCGGCTATCCGTGGTGTTGATGACAGCCAAGGGAAATGGTTAGGTGGTATGT
09PM72399.TXT     ATCCTCGAGCGGCTATCCGTGGTGTTGATGACAGCCAAGGGAAATGGTTAGGTGGTATGT

NIPPONBARE.TXT    TTGATAAAGACAGCTTTGTGGAAACATTTGAAGGTTGGGCTAAGACAGTGGTTACTGGCA
R0146.TXT         TTGATAAAGACAGCTTTGTGGAAACATTTGAAGGTTGGGCTAAGACAGTGGTTACTGGCA
09PM72399.TXT     TTGATAAAGACAGCTTTGTGGAAACATTTGAAGGTTGGGCTAAGACAGTGGTTACTGGCA

NIPPONBARE.TXT    GAGCAAAGCTTGGTGGAATTCCAGTGGGTGTGATAGCTGTGGAGACTCAGACCATGATGC
R0146.TXT         GAGCAAAGCTTGGTGGAATTCCAGTGGGTGTGATAGCTGTGGAGACTCAGACCATGATGC
09PM72399.TXT     GAGCAAAGCTTGGTGGAATTCCAGTGGGTGTGATAGCTGTGGAGACTCAGACCATGATGC

NIPPONBARE.TXT    AAACTATCCCTGCTGACCCTGGTCAGCTTGATTCCCGTGAGCAATCTGTTCCTCGTGCTG
R0146.TXT         AAACTATCCCTGCTGACCCTGGTCAGCTTGATTCCCGTGAGCAATCTGTTCCTCGTGCTG
09PM72399.TXT     AAACTATCCCTGCTGACCCTGGTCAGCTTGATTCCCGTGAGCAATCTGTTCCTCGTGCTG

NIPPONBARE.TXT    GACAAGTGTGGTTTCCAGATTCTGCAACCAAGACTGCGCAGGCATTGCTGGACTTCAACC
R0146.TXT         GACAAGTGTGGTTTCCAGATTCTGCAACCAAGACTGCGCAGGCATTGCTGGACTTCAACC
09PM72399.TXT     GACAAGTGTGGTTTCCAGATTCTGCAACCAAGACTGCGCAGGCATTGCTGGACTTCAACC
```

FIG. 20 (cont.)

| | |
|---|---|
| NIPPONBARE.TXT | GTGAAGGATTACCTCTGTTCATCCTCGCTAACTGGAGAGGCTTCTCTGGTGGACAAAGAG |
| R0146.TXT | GTGAAGGATTACCTCTGTTCATCCTCGCTAACTGGAGAGGCTTCTCTGGTGGACAAAGAG |
| 09PM72399.TXT | GTGAAGGATTACCTCTGTTCATCCTCGCTAACTGGAGAGGCTTCTCTGGTGGACAAAGAG |
| | |
| NIPPONBARE.TXT | ATCTTTTTGAAGGAATTCTTCAGGCTGGCTCGACTATTGTTGAGAACCTTAGGACATACA |
| R0146.TXT | ATCTTTTTGAAGGAATTCTTCAGGCTGGCTCGACTATTGTTGAGAACCTTAGGACATACA |
| 09PM72399.TXT | ATCTTTTTGAAGGAATTCTTCAGGCTGGCTCGACTATTGTTGAGAACCTTAGGACATACA |
| | |
| NIPPONBARE.TXT | ATCAGCCTGCCTTTGTCTACATTCCCATGGCTGCAGAGCTACGAGGAGGGGCTTGGGTTG |
| R0146.TXT | ATCAGCCTGCCTTTGTCTACATTCCCATGGCTGCAGAGCTACGAGGAGGGGCTTGGGTTG |
| 09PM72399.TXT | ATCAGCCTGCCTTTGTCTACATTCCCATGGCTGCAGAGCTACGAGGAGGGGCTTGGGTTG |
| | |
| NIPPONBARE.TXT | TGGTTGATAGCAAGATAAACCCAGACCGCATTGAGTGCTATGCTGAGAGGACTGCAAAAG |
| R0146.TXT | TGGTTGATAGCAAGATAAACCCAGACCGCATTGAGTGCTATGCTGAGAGGACTGCAAAAG |
| 09PM72399.TXT | TGGTTGATAGCAAGATAAACCCAGACCGCATTGAGTGCTATGCTGAGAGGACTGCAAAAA |
| | |
| NIPPONBARE.TXT | GCAATGTTCTGGAACCGCAAGGGGTTAATTGAGATCAAGTTCAGGTCAGAGGAACTCCAGG |
| R0146.TXT | GCAATGTTCTGGAACCGCAAGGGGTTAATTGAGATCAAGTTCAGGTCAGAGGAACTCCAGG |
| 09PM72399.TXT | GCAATGTTCTGGAACCGCAAGGGGTTAATTGAGATCAAGTTCAGGTCAGAGGAACTCCAGG |
| | |
| NIPPONBARE.TXT | ATTGCATGAGTCGGCTTGACCCAACATTAATTGATCTGAAAGCAAAACTCGAAGTAGCAA |
| R0146.TXT | ATTGCATGAGTCGGCTTGACCCAACATTAATTGATCTGAAAGCAAAACTCGAAGTAGCAA |
| 09PM72399.TXT | ATTGCATGAGTCGGCTTGACCCAACATTAATTGATCTGAAAGCAAAACTCGAAGTAGCAA |
| | |
| NIPPONBARE.TXT | ATAAAAATGGAAGTGCTGACACAAAATCGCTTCAAGAAAATATAGAAGCTCGAACAAAAC |
| R0146.TXT | ATAAAAATGGAAGTGCTGACACAAAATCGCTTCAAGAAAATATAGAAGCTCGAACAAAAC |
| 09PM72399.TXT | ATAAAAATGGAAGTGCTGACACAAAATCGCTTCAAGAAAATATAGAAGCTCGAACAAAAC |
| | |
| NIPPONBARE.TXT | AGTTGATGCCTCTATATACTCAGATTGCGATACGGTTTGCTGAATTGCATGATACATCCC |
| R0146.TXT | AGTTGATGCCTCTATATACTCAGATTGCGATACGGTTTGCTGAATTGCATGATACATCCC |
| 09PM72399.TXT | AGTTGATGCCTCTATATACTCAGATTGCGATACGGTTTGCTGAATTGCATGATACATCCC |
| | |
| NIPPONBARE.TXT | TCAGAATGGCTGCGAAAGGTGTGATTAAGAAAGTTGTGGACTGGGAAGAATCACGATCTT |
| R0146.TXT | TCAGAATGGCTGCGAAAGGTGTGATTAAGAAAGTTGTGGACTGGGAAGAATCACGATCTT |
| 09PM72399.TXT | TCAGAATGGCTGCGAAAGGTGTGATTAAGAAAGTTGTGGACTGGGAAGAATCACGATCTT |
| | |
| NIPPONBARE.TXT | TCTTCTATAAGAGATTACGGAGGAGGATCTCTGAGGATGTTCTTGCAAAAGAAATTAGAG |
| R0146.TXT | TCTTCTATAAGAGATTACGGAGGAGGATCTCTGAGGATGTTCTTGCAAAAGAAATTAGAG |
| 09PM72399.TXT | TCTTCTATAAGAGATTACGGAGGAGGATCTCTGAGGATGTTCTTGCAAAAGAAATTAGAG |
| | |
| NIPPONBARE.TXT | CTGTAGCAGGTGAGCAGTTTTCCCACCAACCAGCAATCGAGCTGATCAAGAAATGGTATT |
| R0146.TXT | CTGTAGCAGGTGAGCAGTTTTCCCACCAACCAGCAATCGAGCTGATCAAGAAATGGTATT |
| 09PM72399.TXT | CTGTAGCAGGTGAGCAGTTTTCCCACCAACCAGCAATCGAGCTGATCAAGAAATGGTATT |
| | |
| NIPPONBARE.TXT | CAGCTTCACATGCAGCTGAATGGGATGATGACGATGCTTTTGTTGCTTGGATGGATAACC |
| R0146.TXT | CAGCTTCACATGCAGCTGAATGGGATGATGACGATGCTTTTGTTGCTTGGATGGATAACC |
| 09PM72399.TXT | CAGCTTCACATGCAGCTGAATGGGATGATGACGATGCTTTTGTTGCTTGGATGGATAACC |

FIG. 20 (cont.)

```
NIPPONBARE.TXT   CTGAAAACTACAAGGATTATATTCAATATCTTAAGGCTCAAAGAGTATCCCAATCCCTCT
R0146.TXT        CTGAAAACTACAAGGATTATATTCAATATCTTAAGGCTCAAAGAGTATCCCAATCCCTCT
09PM72399.TXT    CTGAAAACTACAAGGATTATATTCAATATCTTAAGGCTCAAAGAGTATCCCAATCCCTCT

NIPPONBARE.TXT   CAAGTCTTTCAGATTCCAGCTCAGATTTGCAAGCCCTGCCACAGGGTCTTTCCATGTTAC
R0146.TXT        CAAGTCTTTCAGATTCCAGCTCAGATTTGCAAGCCCTGCCACAGGGTCTTTCCATGTTAC
09PM72399.TXT    CAAGTCTTTCAGATTCCAGCTCAGATTTGCAAGCCCTGCCACAGGGTCTTTCCATGTTAC

NIPPONBARE.TXT   TAGATAAGGTAATTAGCTTACTGATGCTTATATAAATTCTTTTTCATTACATATGGCTGG
R0146.TXT        TAGATAAGGTAATTAGCTTACTGATGCTTATATAAATTCTTTTTCATTACATATGGCTGG
09PM72399.TXT    TAGATAAGGTAATTAGCTTACTGATGCTTATATAAATTCTTTTTCATTACATATGGCTGG

NIPPONBARE.TXT   AGAACTATCTAATCAAATAATGATTATAATTCCAATCGTTCTTTTTATGCCATTATGATC
R0146.TXT        AGAACTATCTAATCAAATAATGATTATAATTCCAATCGTTCTTTTTATGCCATTATGATC
09PM72399.TXT    AGAACTATCTAATCAAATAATGATTATAATTCCAATCGTTCTTTTTATGCCATTATGATC

NIPPONBARE.TXT   TTCTGAAATTTCCTTCTTTGGACACTTATTCAGATGGATCCCTCTAGAAGAGCTCAACTT
R0146.TXT        TTCTGAAATTTCCTTCTTTGGACACTTATTCAGATGGATCCCTCTAGAAGAGCTCAACTT
09PM72399.TXT    TTCTGAAATTTCCTTCTTTGGACACTTATTCAGATGGATCCCTCTAGAAGAGCTCAACTT

NIPPONBARE.TXT   GTTGAAGAAATCAGGAAGGTCCTTGGTTGAATCATATGATG
R0146.TXT        GTTGAAGAAATCAGGAAGGTCCTTGGTTGAATCATATGATG
09PM72399.TXT    GTTGAAGAAATCAGGAAGGTCCTTGGTTGAATCATATGATG
```

FIG. 20 (cont.)

```
NIPP-PRO.TXT        MDRPAGLNDIGMVAWTLKMSTPEFPSGREIIVVANDITFRAGSFGPREDAFFEAVTNLAC
R0146-PRO.TXT       MDRPAGLNDIGMVAWTLKMSTPEFPSGREIIVVANDITFRAGSFGPREDAFFEAVTNLAC
09PM72399-PRO.TX    MDRPAGLNDIGMVAWTLKMSTPEFPSGREIIVVANDITFRAGSFGPREDAFFEAVTNLAC

NIPP-PRO.TXT        EKKLPLIYLAANSGARIGIADEVKSCFRVGWSDDGSPERGFQYIYLSEEDYARIGTSVIA
R0146-PRO.TXT       EKKLPLIYLAANSGARIGIADEVKSCFRVGWSDDGSPERGFQYIYLSEEDYARIGTSVIA
09PM72399-PRO.TX    EKKLPLIYLAANSGARIGIADEVKSCFRVGWSDDGSPERGFQYIYLSEEDYARIGTSVIA

NIPP-PRO.TXT        HKMQLDSGEIRWVIDSVVGKEDGLGVENIHGSAAIASAYSRAYKETFTLTFVTGRTVGIG
R0146-PRO.TXT       HKMQLDSGEIRWVIDSVVGKEDGLGVENIHGSAAIASAYSRAYKETFTLTFVTGRTVGIG
09PM72399-PRO.TX    HKMQLDSGEIRWVIDSVVGKEDGLGVENIHGSAAIASAYSRAYKETFTLTFVTGRTVGIG

NIPP-PRO.TXT        AYLARLGIRCIQRLDQPIILTGYSALNKLLGREVYSSHMQLGGPKIMATNGVVHLTVSDD
R0146-PRO.TXT       AYLARLGIRCIQRLDQPIILTGYSALNKLLGREVYSSHMQLGGPKIMATNGVVHLTVSDD
09PM72399-PRO.TX    AYLARLGIRCIQRLDQPIILTGYSALNKLLGREVYSSHMQLGGPKIMATNGVVHLTVSDD

NIPP-PRO.TXT        LEGVSNILRWLSYVPAYIGGPLPVTTPLDPPDRPVAYIPENSCDPRAAIRGVDDSQGKWL
R0146-PRO.TXT       LEGVSNILRWLSYVPAYIGGPLPVTTPLDPPDRPVAYIPENSCDPRAAIRGVDDSQGKWL
09PM72399-PRO.TX    LEGVSNILRWLSYVPAYIGGPLPVTTPLDPPDRPVAYIPENSCDPRAAIRGVDDSQGKWL

NIPP-PRO.TXT        GGMFDKDSFVETFEGWAKTVVTGRAKLGGIPVGVIAVETQTMMQTIPADPGQLDSREQSV
R0146-PRO.TXT       GGMFDKDSFVETFEGWAKTVVTGRAKLGGIPVGVIAVETQTMMQTIPADPGQLDSREQSV
09PM72399-PRO.TX    GGMFDKDSFVETFEGWAKTVVTGRAKLGGIPVGVIAVETQTMMQTIPADPGQLDSREQSV

NIPP-PRO.TXT        PRAGQVWFPDSATKTAQALLDFNREGLPLFILANWRGFSGGQRDLFEGILQAGSTIVENL
R0146-PRO.TXT       PRAGQVWFPDSATKTAQALLDFNREGLPLFILANWRGFSGGQRDLFEGILQAGSTIVENL
09PM72399-PRO.TX    PRAGQVWFPDSATKTAQALLDFNREGLPLFILANWRGFSGGQRDLFEGILQAGSTIVENL

NIPP-PRO.TXT        RTYNQPAFVYIPMAAELRGGAWVVDSKINPDRIECYAERTAKGNVLEPQGLIEIKFRSE
R0146-PRO.TXT       RTYNQPAFVYIPMAAELRGGAWVVDSKINPDRIECYAERTAKGNVLEPQGLIEIKFRSE
09PM72399-PRO.TX    RTYNQPAFVYIPMAAELRGGAWVVDSKINPDRIECYAERTAKSNVLEPQGLIEIKFRSE

NIPP-PRO.TXT        ELQDCMSRLDPTLIDLKAKLEVANKNGSADTKSLQENIEARTKQLMPLYTQIAIRFAELH
R0146-PRO.TXT       ELQDCMSRLDPTLIDLKAKLEVANKNGSADTKSLQENIEARTKQLMPLYTQIAIRFAELH
09PM72399-PRO.TX    ELQDCMSRLDPTLIDLKAKLEVANKNGSADTKSLQENIEARTKQLMPLYTQIAIRFAELH

NIPP-PRO.TXT        DTSLRMAAKGVIKKVVDWEESRSPFYKRLRRRISEDVLAKEIRAVAGEQFSHQPAIELIK
R0146-PRO.TXT       DTSLRMAAKGVIKKVVDWEESRSPFYKRLRRRISEDVLAKEIRAVAGEQFSHQPAIELIK
09PM72399-PRO.TX    DTSLRMAAKGVIKKVVDWEESRSPFYKRLRRRISEDVLAKEIRAVAGEQFSHQPAIELIK

NIPP-PRO.TXT        KWYSASHAAEWDDDDAFVAWMDNPENYKDYIQYLKAQRVSQSLSSLSDSSSDLQALPQGL
R0146-PRO.TXT       KWYSASHAAEWDDDDAFVAWMDNPENYKDYIQYLKAQRVSQSLSSLSDSSSDLQALPQGL
09PM72399-PRO.TX    KWYSASHAAEWDDDDAFVAWMDNPENYKDYIQYLKAQRVSQSLSSLSDSSSDLQALPQGL

NIPP-PRO.TXT        SMLLDKVISLLMLI
R0146-PRO.TXT       SMLLDKVISLLMLI
09PM72399-PRO.TX    SMLLDKVISLLMLI
```

RICE RESISTANT TO HPPD AND ACCASE INHIBITING HERBICIDES

CROSS-REFERENCE TO RELATED PATENT APPLICATIONS

This application is a Continuation of U.S. application Ser. No. 14/465,242, filed Aug. 21, 2014, now U.S. Pat. No. 9,303,270 which claims the benefit of priority under 35 U.S.C. § 119(e) to U.S. Provisional Patent Application No. 61/869,608, filed Aug. 23, 2013, and is a Continuation-in-Part of U.S. patent application Ser. No. 13/975,034, filed Aug. 23, 2013, which claims the benefit of priority under 35 U.S.C. § 119(e) to U.S. Provisional Patent Application No. 61/692,861 filed Aug. 24, 2012; application Ser. No. 14/465, 242 is also a Continuation-in-Part of U.S. patent application Ser. No. 13/554,675, filed Jul. 20, 2012, now U.S. Pat. No. 9,370,149 which claims the benefit of priority under 35 U.S.C. § 119(e) to U.S. Provisional Patent Application No. 61/510,585, filed Jul. 22, 2011, and 61/541,832, filed Sep. 30, 2011. The disclosures set forth in the referenced applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 13, 2014, is named 706191_SEQ_US.txt and is 79 KB in size.

BACKGROUND

Mutant rice is disclosed that is (1) resistant/tolerant to both HPPD and ACCase inhibiting herbicides; or (2) resistant/tolerant only to 4-hydroxyphenylpyruvate dioxygenase (HPPD) inhibiting herbicides. Methods of weed control are disclosed using rice with these herbicide resistant/tolerant crops in fields. Methods to produce herbicide resistant/ tolerant rice are also disclosed.

Value of Rice Crops

Rice is an ancient agricultural crop and today is one of the principal food crops of the world. There are two cultivated species of rice: *Oryza sativa* L., the Asian rice, and *Oryza glaberrima* Steud., the African rice. The Asian species constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valley of California. Other countries, in particular in South America and the East, are major rice producers.

Rice is one of the few crops that can be grown in a shallow flood as it has a unique structure allowing gas exchange through the stems between the roots and the atmosphere. Growth in a shallow flood results in the best yields and is the reason that rice is usually gown in heavy clay soils, or soils with an impermeable hard pan layer just below the soil surface. These soil types are usually either not suitable for other crops or at best, the crops yield poorly.

The constant improvement of rice is imperative to provide necessary nutrition for a growing world population. A large portion of the world population consumes rice as their primary source of nutrition and crops must thrive in various environmental conditions including competing with weeds and attacks by unfavorable agents. Rice improvement is carried out through conventional breeding practices and also by recombinant genetic techniques. Though appearing straightforward to those outside this discipline, crop improvement requires keen scientific and artistic skill and results are generally unpredictable.

Although specific breeding objectives vary somewhat in the different rice producing regions of the world, increasing yield is a primary objective in all programs.

Plant breeding begins with the analysis and definition of strengths and weaknesses of cultivars in existence, followed by the establishment of program goals, to improve areas of weakness to produce new cultivars. Specific breeding objectives include combining in a single cultivar an improved combination of desirable traits from the parental sources. Desirable traits may be introduced due to spontaneous or induced mutations. Desirable traits include higher yield, resistance to environmental stress, diseases and insects, better stems and roots, tolerance to low temperatures, better agronomic characteristics, nutritional value and grain quality.

For example, the breeder initially selects and crosses two or more parental lines, followed by selection for desired traits among the many new genetic combinations. The breeder can theoretically generate billions of new and different genetic combinations via crossing. Breeding by using crossing and selfing, does not imply direct control at the cellular level. However, that type of control may be achieved in part using recombinant genetic techniques.

Pedigree breeding is used commonly for the improvement of self-pollinating crops such as rice. For example, two parents which possess favorable, complementary traits are crossed to produce an $F_1$ generation. One or both parents may themselves represent an $F_1$ from a previous cross. Subsequently a segregating population is produced, by growing the seeds resulting from selfing one or several $F_1$s if the two parents are pure lines, or by directly growing the seed resulting from the initial cross if at least one of the parents is an $F_1$. Selection of the best individual genomes may begin in the first segregating population or $F_2$; then, beginning in the $F_3$, the best individuals in the best families are selected. "Best" is defined according to the goals of a particular breeding program e.g., to increase yield, resist diseases. Overall a multifactorial approach is used to define "best" because of genetic interactions. A desirable gene in one genetic background may differ in a different background. In addition, introduction of the gene may disrupt other favorable genetic characteristics. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new parental lines.

Backcross breeding has been used to transfer genes for a highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The process is used to recover all of the beneficial characteristics of the recurrent parent with the addition of the new trait provided by the donor parent.

Promising advanced breeding lines are thoroughly tested and compared to appropriate standards in environments representative of the commercial target area(s) for at least three or more years. The best lines are candidates for new commercial varieties or parents of hybrids; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is not only a time-consuming process, but requires precise forward planning, efficient use of resources, and a minimum of changes in direction. The results include novel genetic combinations not found in nature.

Some improvement of rice through breeding may be restricted to the natural genetic variation in rice and hybridizing species, such as wild rice. The introduction of new variation in a breeding program is usually through the crossing program as described, such as pedigree or backcross breeding. However, occasionally natural mutations are found that result in the introduction of new traits such as disease resistance or height changes. Breeders have also developed new traits by inducing mutations (small changes in the DNA sequence) into a rice genome. Some of these mutations or combination of genes are not found in nature. Commonly, EMS or sodium azide plus MNU are used as mutagenic agents. These chemicals randomly induce single base changes in DNA, usually of G and C changed to A and T. Overall effects are unpredictable. Most of these changes have no effect on the crop as they fall either outside the gene coding regions or don't change the amino acid sequence of the gene product. However, some produce new traits or incorporate new DNA changes into previous lines.

The breeder has no direct control of mutation sites in the DNA sequence. The identification of useful changes is due to the random possibility that an effective mutation will be induced and that the breeder will recognize the phenotypic effects of the change and will be able to select rice having that mutation. Seeds are treated with the mutagenic chemical and immediately planted to grow and produce M2 seed. The M2 seed will carry numerous new variations; therefore, no two experiments will produce the same combinations. Among these variations new traits previously not existing in rice and unavailable for selection by a plant breeder may be found and used for rice improvement.

To find new traits the breeder must use efficient and strategic selection strategies as the process is completely random and has an extremely low frequency of useful new combinations. Among thousands of induced new genetic variants there may be only one with a desirable new trait. An optimal selection system will screen through thousands of new variants and allow detection of a few or even a single plant that might carry a new trait. After identifying or finding a possible new trait the breeder must develop a new cultivar by pedigree or backcross breeding and extensive testing to verify the new trait and cultivar exhibits stable and heritable value to rice producers.

Using recombinant genetic techniques, nucleic acid molecules with mutations that encode improved characteristics in rice, may be introduced into rice with commercially suitable genomes. After a mutation is identified by whatever course, it may be transferred into rice by recombinant techniques.

Applications of Herbicide Resistance Patents in Rice

Weeds and other competitors for resources in crop fields compete for resources and greatly reduce the yield and quality of the crop. Weeds have been controlled in crops through the application of selective herbicides that kill the weeds, but do not harm the crop. Usually selectivity of the herbicides is based on biochemical variations or differences between the crop and the weeds. Some herbicides are non-selective, meaning they kill all or almost all plants. Non-selective or broad spectrum herbicides can be used in crops if new genes are inserted that express specific proteins that convey tolerance or resistance to the herbicide. Resistance to herbicides has also been achieved in crops through genetic mutations that alter proteins and biochemical processes. These mutations may arise in nature, but mostly they have been induced in crops or in vitro in tissue cultures or by inducing mutations in vivo. Unfortunately in some instances, especially with repeated use of a particular herbicide, weeds have developed resistance through the unintended selection of natural mutations that provide resistance. When weeds become resistant to a particular herbicide, that herbicide is no longer useful for weed control. The development of resistance in weeds is best delayed through alternating the use of different modes of action to control weeds, interrupting development of resistant weeds.

Rice production is plagued by broad leaf plants and a particularly hard to control weed called red rice. One difficulty arises because red rice is so genetically similar to cultivated rice (they occasionally cross pollinate) that there are no selective herbicides available that target red rice, yet do not harm the cultivated rice. Control is currently provided in commercial rice production through the development of mutations found in rice that render rice resistant to broad spectrum herbicides e.g. imidazolinone and sulfonylurea herbicides. Rice resistant to herbicides that inhibit other deleterious plants, such as broad leaf plants, are needed.

Finding new mutations in rice that makes it resistant to a variety of herbicides, and to combinations of herbicides with alternative modes of action, would greatly benefit rice production. Obtaining and incorporating genes for herbicide resistance into rice genomes with additional favorable characteristics and alternative resistances is challenging, unpredictable, time consuming and expensive, but necessary to meet the world's increasing food needs.

SUMMARY

Described and disclosed herein are novel and distinctive rice lines with unique resistances to herbicides in particular HPPD and ACCase inhibiting herbicides and combinations thereof. For example, a mutant rice line designated ML0831266-03093 is disclosed that is resistant/tolerant to HPPD inhibiting herbicides (ATCC deposit PTA-13620). The HPPD inhibiting herbicides include mesotrione, benzobicyclon, and combinations thereof. An embodiment of a mutant rice line designated ML0831265-01493 (ATCC deposit PTA-12933, mutation G2096S) is resistant/tolerant to ACCase inhibitors.

Embodiments of rice resistant to both HPPD and ACCase inhibitors, include rice designated PL121448M2-80048 (ATCC deposit PTA-121362) and PL 1214418M2-73009 (ATCC deposit PTA-121398).

A method to control weeds in a rice field, wherein the rice in the field includes plants resistant to a plurality of herbicides, includes:
  a. using herbicide resistant/tolerant rice in the field; and
  b. contacting the rice field with a plurality of herbicides, for example, one of which is an HPPD inhibiting herbicide, another an ACCase inhibitor.

Rice lines either singly or multiply resistant/tolerant extend the useful life of several herbicides due to being able to rotate the kinds of herbicides applied in grower's fields thus slowing the development of weed resistance. Several methods are possible to deploy these resistances into hybrids or varieties for weed control, as well as options for hybrid seed production. The rice lines described herein represent new methods for weed control in rice and can be deployed in any of many possible strategies to control weeds and provide for long-term use of these and other weed control methods. In particular, mutant rice tolerant to HPPD inhibiting herbicides and to both HPPD and ACCase inhibitors are disclosed.

Rice production for good yields requires specific weed control practices. Some herbicides are applied at the time of planting and others are applied before a permanent flood is applied, few weeds can grow in a full flood.

Through developing sources of resistance to multiple herbicides, more options are available for weed control in rice. The rice lines claimed provide the ability to use herbicides with a new mode of action for weed control. The ability to use an HPPD inhibiting herbicide in combination with an ACCase inhibitor, represents a mode of action not previously reported in rice. The use of these rice lines including combining lines with resistance to herbicide with other modes of action provides new options for weed control in grower's fields thus slowing the development of weed resistance. Several methods are possible to deploy this resistance in hybrids for weed control as well as options for hybrid seed production.

Cells derived from herbicide resistant seeds, plants grown from such seeds and cells derived from such plants, progeny of plants grown from such seed and cells derived from such progeny are within the scope of this disclosure. The growth of plants produced from deposited seeds, and progeny of such plants will typically be resistant/tolerant to HPPD inhibiting and ACCase inhibiting herbicides at levels of herbicide that would normally inhibit the growth of a corresponding wild-type plant.

A method for controlling growth of weeds in the vicinity of herbicide resistant/tolerant rice plants is also within the scope of the disclosure. One example of such methods is applying one or more herbicides to the fields of rice plants at levels of herbicide that would normally inhibit the growth of a rice plant. For example, at least one herbicide inhibits HPPD activity. A plurality includes, for example, HPPD and ACCase inhibitors. Surprisingly, some mixtures of herbicide increased the activity of all components. Such methods may be practiced with any herbicide that inhibits HPPD and/or ACCase activity and any resistant rice mutation, e.g., the embodiments disclosed herein.

Unexpectedly, using a mixture of HPPD and ACCase inhibiting herbicides, provided better results than when each herbicide was applied separately.

A method for growing herbicide resistant/tolerant rice plants includes (a) planting resistant rice seeds; (b) allowing the rice seeds to sprout; (c) applying one or more herbicides to the rice sprouts at levels of herbicide that would normally inhibit the growth of a rice plant. For example, at least one of the herbicides inhibits HPPD, other herbicides include ACCase inhibitors.

Methods of producing herbicide-tolerant rice plants may also use a transgenes or plurality of transgenes. One embodiment of such a method is transforming a cell of a rice plant with transgenes, wherein the transgenes encode an HPPD and an ACCase enzyme that confers tolerance in resulting rice plants to one or more herbicides. Any suitable cell may be used in the practice of these methods, for example, the cell may be in the form of a callus.

BRIEF DESCRIPTION OF DRAWINGS

FIG. 16A and FIG. 16B are a tabular representation of sergeants identified in a F4 population; the F4 population was derived from F2 selections carrying both HPPD and ACCase tolerance from a cross between the HPPD tolerant line ML0831266-03093 and the ACCase tolerant line ML0831265-01493; each row represents a different line and each column is a molecular marker within the QTL for the HPPD tolerant mutation on chromosome 1. FIG. 16B is a continuation of FIG. 16A black lines (boundaries) represent results of the genotype of the HPPD tolerant line ML0831266-03093 (20) and the genotype of the ACCase tolerant line ML0831265-01493 (10); observing the tolerance level of these lines to the HPPD herbicide mesotrione allows the tolerance mutation to be mapped to a specific gene.

FIG. 17 is a tabular representation of sergeants identified in a F4 population; the F4 population was derived from F2 selections carrying both HPPD and ACCase tolerance from a cross between the HPPD tolerant line ML0831266-03093 and the ACCase tolerant line ML0831265-01493; each row represents a different line and each column is a molecular marker within the QTL for the HPPD non-induced tolerance on chromosome two; black lines (boundaries) represent results of the genotype of the HPPD tolerant line ML0831266-03093 (20) and the unshaded represents the genotype of the ACCase tolerant line ML0831265-01493 (10); observing the tolerance level of these lines to the HPPD herbicide mesotrione allows the resistance/tolerance to be mapped to a specific gene.

FIG. 18A the mutant line ML0831266-03093 shows little damage from the spray application, while FIG. 18B the unmutated type P1003 is severely injured (damaged) and FIG. 18C the other type of rice, R0146, used to make ACCase mutant line ML0831265-01493 is completely killed.

FIG. 19A=initial results and FIG. 19B=subsequent results.

FIG. 20 shows a DNA sequence for the carboxyl transferase coding region in the ACCase coding gene; a single nucleotide change (box) that encodes a mutation from G2096S is identified in the mutant line ML0831265-01493 which is designated as 09PM72399. (SEQ ID NO: 202) [NIPPONBARE (SEQ ID NO: 200) is a control; R0146 (SEQ ID NO: 201) is the original line treated with a mitogen to produce a mutation population.

FIG. 21 shows comparison of protein sequences for the carboxyl transferase region of the ACCase gene; the line with code 09PM72399 (SEQ ID NO: 204) is the line ML0831265-01493; this line shows a change of a single amino acid (box) at position 2096, relative to Black-Grass; R0146 (SEQ ID NO: 204) is the original line treated with a mutagen to produce a mutation population. [NIPPONBARE is SEQ ID NO: 203]

DETAILED DESCRIPTION

Mutation Population and Establishment

Figure 1:
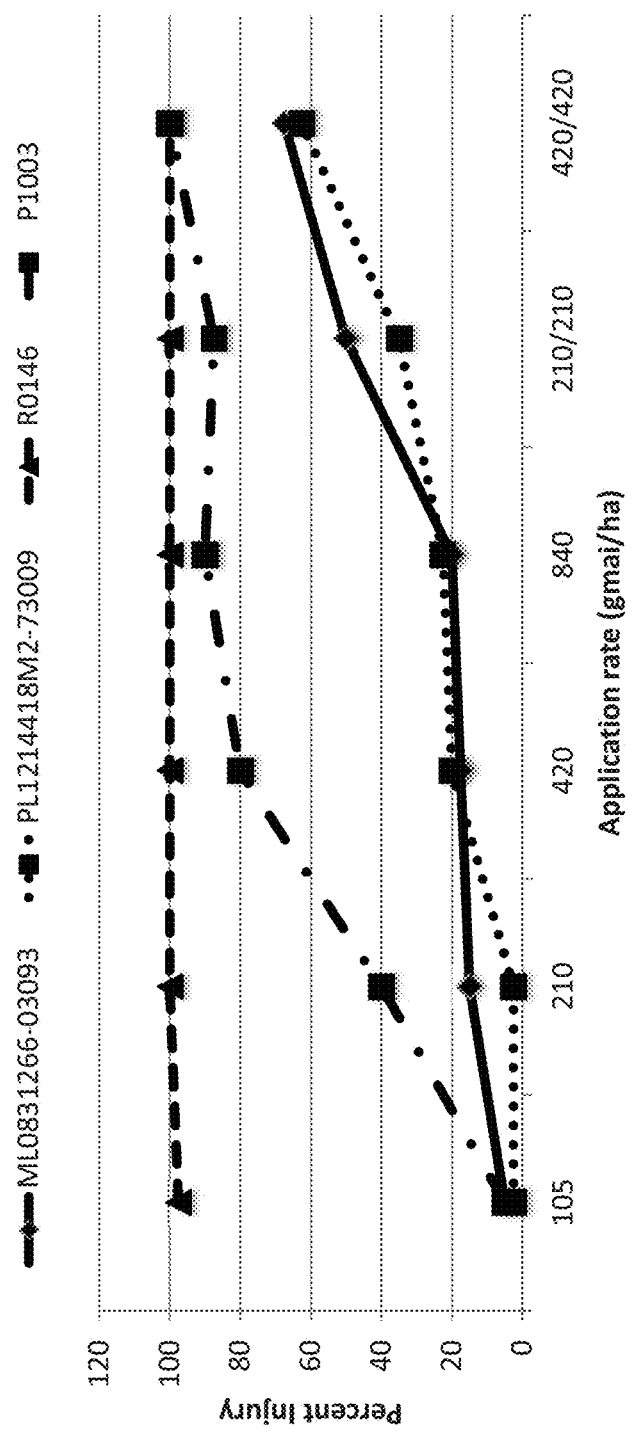
FIG. 1 is a graphical representation of a trait tolerance trial; the trial was planted, mesotrione was applied at the indicated rates about 1 month later (3-4 leaf stage), and a second application was applied on the two indicated treatments about 1 week later; the rice was evaluated for the percent of injury or damage as compared to unsprayed rice twenty-one days after the first herbicide application; line ML0831266-03093 is the HPPD resistant line and R0146 and P1003 are control lines with no induced mutation; the line PL1214418M2-73009 was selected out of a cross between the HPPD tolerant line ML0831266-03093 (parent is P1003) and the ACCase resistant line ML0831265-01493 (parent is R0146). The newly developed line PL1214418M2-73009 shows equivalent tolerance as the original HPPD tolerant line ML0831266-03093.

A mutation breeding program was initiated to develop proprietary herbicide resistant/tolerant lines. A permanent mutant population was created by exposing approximately 10,000 seeds (estimated by the average weight of a kernel) of three rice lines including P1003, R0146, and P1062 to both mutagens sodium azide (AZ) and methyl-nitrosourea (MNU). The treated seeds were planted. Individual plants were harvested creating 8,281 potentially mutation lines. The lines have been maintained as a permanent mutant population for trait screening.
Development of Tolerance to HPPD and ACCase Inhibiting Herbicides by Combining the Tolerances in Lines ML0831266-03093 and ML0831265-01493

Herbicides that target the HPPD enzyme, primarily control broad leaf weeds. However trials in rice show prevalent control of grass weeds in rice, including red weedy rice especially with mesotrione herbicide.

On the other hand, the primary weed target of ACCase herbicides is monocot plants including rice, grass weeds, and red rice. However, some ACCase herbicides have lower activity on rice. This weakness is likely transferred to red rice as the plants are very closely related. Combining the HPPD tolerance and the ACCase tolerance into a single rice line allows a broad spectrum weed control strategy for rice. The HPPD herbicide controls broad leaf weeds and enhances the effect of ACCase herbicides for control of monocot weeds including red rice.

Combining the HPPD tolerance with the ACCase tolerance into a single rice line was initiated with the HPPD tolerance mapping project by crossing the HPPD tolerant line ML0831266-03093 to the ACCase tolerant line ML0831265-01493. In mapping the F2 population plants were selected for HPPD tolerance by applying mesotrione first at a low rate (105 gmai/ha) followed by a high rate (630 gmai/ha). In this process molecular markers were also developed allowing future selection of HPPD tolerance by either markers or herbicide tolerance screening or both.

After identifying plants that were tolerant to the HPPD herbicide mesotrione, they were also tested with the ACCase tolerance functional marker for the G2096S mutation in the ACCase donor parent line ML0831265-01493. Information to develop ACCase G2096S markers are in FIGS. 20, 21.

After this process, a set of 25 F2 plants with the ACCase mutation to herbicide resistance, and the HPPD genetic herbicide resistance on chromosome 1 and chromosome 2, in at least the heterozygous condition, were identified. The plants were transplanted to another field for harvesting at maturity. Out of the 25 plants, eight were homozygous for the ACCase mutation and one plant was homozygous for the ACCase mutation, the HPPD tolerance mutation, and the non-induced tolerance gene. The 25 plants were bagged at flowering and the seed harvested at maturity from each plant individually.

An early maturing group of plants was harvested as early as possible and the seeds planted in the greenhouse to help quickly advance to the F4 generation. Selections on the F3 plants were made by molecular markers flanking the HPPD tolerance mutation and native tolerance the ACCase functional mutation. Homozygous plants for all the selected genomic regions were advanced to the F5 generation. The F5 seed was confirmed to carry tolerance to ACCase herbicides and the HPPD herbicide mesotrione. Among the F5 lines PL1214418M2-80048 was selected due to a high seed yield and being homozygous for the ACCase tolerance mutation at position G2096S, the HPPD tolerance mutation, and the HPPD tolerance native gene. Seed from the line PL1214418M2-80048 was deposited at the ATCC and given a deposit number PTA-121362 (see Table 8).

A second line was developed by planting F3 seed in rows. The plants were sprayed with the HPPD herbicide mesotrione and selected for little or no injury as compared to unsprayed controls. Leaf tissue was also collected and the plants were tested for inheritance of the ACCase tolerance mutation G2096S, the HPPD mutation tolerance, and the HPPD non-induced tolerance. Plants homozygous for all three tolerance genes or QTLs were identified and harvested. The F4 seed (PL1214418M2-73009) was bulked together from plants carrying all three tolerance genes or QTLs and used for testing or as a new donor line for tolerance to both ACCase and HPPD herbicides. Seed of the source PL1214418M2-73009 was deposited at the ATCC and given a deposit number PTA-121398 (see Table 8).

Tolerance of New Lines Combining HPPD and ACCase is Equivalent and Selectable in Breeding Populations The seed source PL1214418M2-73009 was developed from a cross between the HPPD resistant line ML0831266-03093 and the ACCase resistant line ML0831265-01493 and was sufficient to allow testing to verify equivalent tolerance to HPPD and ACCase inhibitors in new lines. Two trials were conducted to measure recovery of tolerance to both ACCase and HPPD herbicides in the new line PL1214418M2-73009. Recovery of tolerance in the line combining the two traits will illustrate that the traits are heritable and can be used to produce new varieties and hybrids carrying herbicide resistance. These trials are important as often times it is difficult to recover complex QTLs for quantitative traits or in some cases a traits response is dependent upon the genetic background. In the first trail the lines resistance to mesotrione (HPPD herbicide) was evaluated by planting line PL1214418M2-73009, the HPPD resistant line ML0831266-03093 and wild-type rice line P1003 and R0146 in plots (5 feet×10 feet). Mesotrione was applied at 0.5×, 1×, 2×, and 4× multiples of the labeled application rate (210 gmai/ha). Two additional treatments were included with a 1× and 2× rate followed by a second application 14 days afterward with the same rates. Full recovery of the HPPD resistance from line ML0831266-03093 was achieved in the line PL1214418M2-73009 as it and the original trait line had the same response to the herbicide applications (FIG. 1). These results show that the HPPD resistant trait can be bred and selected to develop commercial products.

Figure 2:
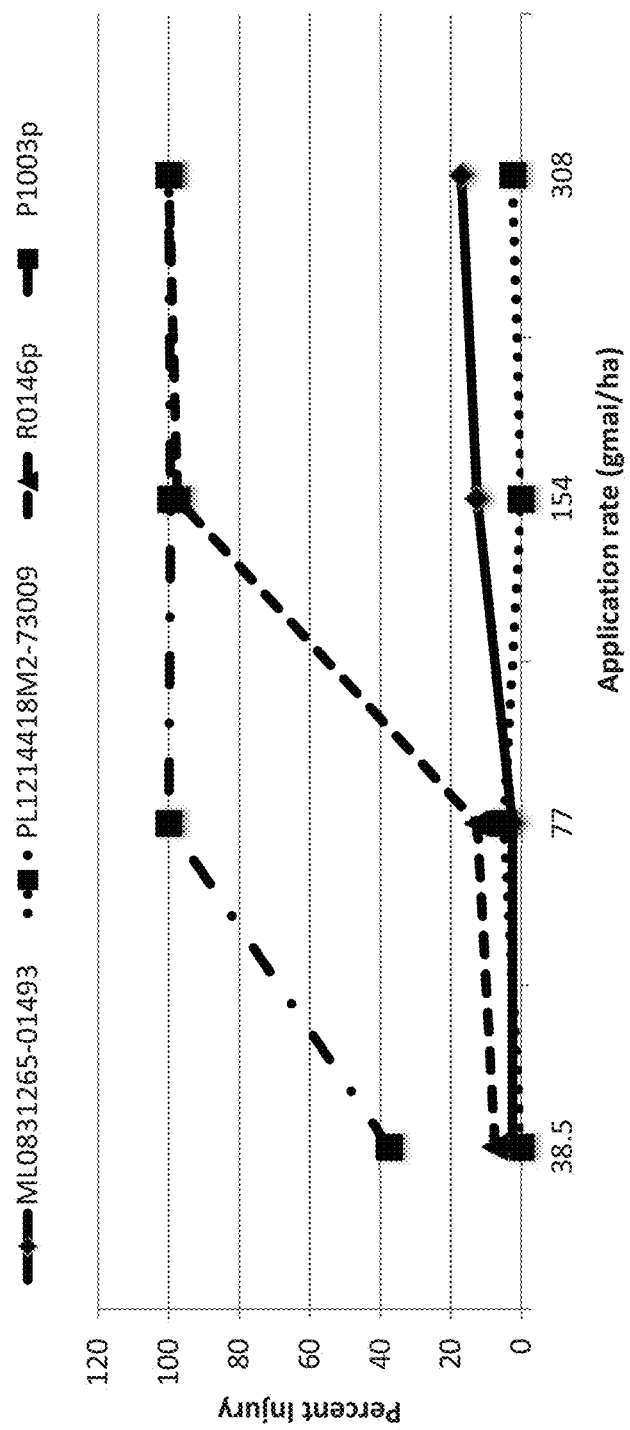
FIG. 2 is a graphical representation of a trait tolerance trial; the trial rice were planted, quizalofop was applied at the indicated rates about 5 weeks later (initiating tillering); the rice was evaluated for the percent of injury or damage as compared to unsprayed rice four weeks after herbicide application; line ML0831265-01493 is the ACCase resistant line and R0146 and P1003 are control lines; the line PL1214418M2-73009 was selected out of a cross between the HPPD tolerant line ML0831266-03093 (parent is P1003) and the ACCase tolerant line ML0831265-01493 (parent is R0146). The newly developed line PL1214418M2-73009 which has combined resistance shows equivalent or better as the original ACCase resistant line ML0831265-01493.

Another trial was conducted to confirm recovery of the ACCase inhibitor resistance from the G2096S mutation as in the line ML0831265-01493. In this trial the new line PL1214418-73009 with combined HPPD and ACCase tolerance was planted in a row along with other various lines including the original donor line ML0831265-01493 (planted in a plot), ML0831266-03093, P1003, R0146 parent line for ACCase tolerance. The lines were all tested with the ACCase herbicides fluazifop at 0.5×, 1×, 2×, and 4× multiples of the label application rate (210 gmai/ha) and quizalofop at 0.5×, 1×, 2×, and 4× multiples of the label application rate (77 gmai/ha). In these trials the three new lines that inherited the ACCase tolerance all showed equivalent tolerance to the ACCase herbicides as did the donor line ML0831265-01493 (FIG. 2).

The tolerance to HPPD herbicides is more complex than the ACCase tolerance because it requires two genes that are different from the gene targeted by the herbicide. In spite of this greater complexity, the equivalent tolerance was recovered through selection of both the native tolerance gene and the mutation tolerance. The ACCase parent line ML0831265-01493 in this cross was highly sensitive to the HPPD herbicide mesotrione and thus was not expected to contribute any towards HPPD tolerance. Resistance/tolerance to HPPD herbicides is mostly likely caused by these two genes alone as they were the focus of the selection process, and the new line PL1214418M2-73009 shows equivalent resistance. These results show that the resistance for both ACCase and HPPD inhibitors is inherited and can be bred into any rice for commercial development of both HPPD and ACCase inhibitor resistance in rice.

Figure 3A:
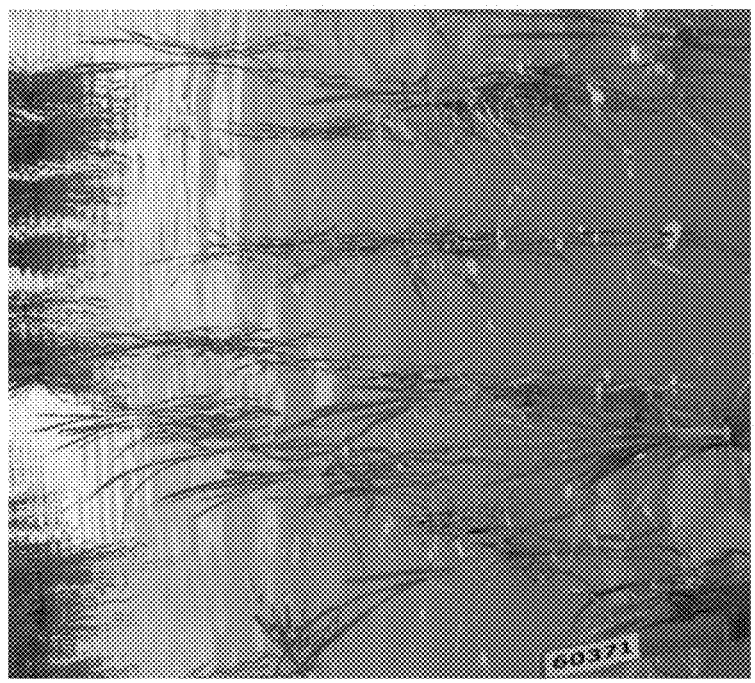
FIG. 3A-3B is a photograph of line ML0831266-03093 that in addition to resistance to HPPD herbicides also has enhanced resistance to ACCase herbicides. Enhanced resistance is demonstrated by plants from the HPPD resistant line ML0831266-03093 (FIG. 3A) surviving an application of quizalofop (77 gm ai/ha) whereas the wild-type parent line P1003 (FIG. 3B) does not survive. Picture taken four weeks after herbicide application.
Figure 3B:

Identification of Unexpected Increased Tolerance to ACCase Herbicides by the HPPD Tolerance Mutation During the process of showing equivalent resistance of the ACCase tolerance in the new line PL1214418M2-73009, the HPPD tolerant line ML0831266-03093 was also evaluated for response to ACCase tolerance by application of the ACCase herbicides fluazifop at 0.5×, 1×, 2×, and 4× multiples of the label application rate (210 gmai/ha) and quizalofop at 0.5×, 1×, 2×, and 4× multiples of the label application rate (77 gmai/ha). In the field trials the resistant HPPD line ML0831266-03093 was planted in a row adjacent to the parent line P1003. During observations it became clear that the line ML0831266-03093 (FIG. 3A) had more resistance to the ACCase inhibiting herbicides than did line P1003 (FIG. 3B). These results suggest that the HPPD tolerance mutation has activity against ACCase inhibiting herbicides in addition to HPPD inhibiting herbicides. By combining the HPPD tolerance with the ACCase tolerance the newly developed line PL1214418M2-73009, or any other new line and other derived lines because resistance is heritable and can be bred into lines e.g. progeny may carry a higher tolerance to ACCase inhibiting herbicides than lines developed from only the ACCase inhibitor resistant line ML0831265-01493.

Identification of the Tolerance Contribution from the HPPD Tolerance Mutation and the Non-Induced Tolerance Gene from P1003

During the breeding process to develop new lines (PL1214418M2-80048 and PL1214418M2-73009) with resistance/tolerance to HPPD and ACCase herbicides, two other lines were also investigated to determine the contribution of the HPPD tolerance mutation and the HPPD tolerance native gene. The line PL1214418M2-73001 carries ACCase tolerance and only the HPPD tolerance, whereas mutation PL1214418M2-73013 carries ACCase tolerance and only the HPPD native tolerance gene. These selections allow the estimation of the tolerance effect of each of the two genes required for tolerance to HPPD herbicides. The tolerance effect of each gene was measured by growing the lines in single rows including the newly developed line PL1214418M2-73009 that carries both the HPPD tolerance from the mutation and the non-induced tolerance, the HPPD tolerant line ML0831266-0309, and the non-induced parent line P1003. The field plots were sprayed at the 4 leaf stage with the HPPD herbicide mesotrione at 0.5×, 1×, 2×, and 4× multiples of the labeled application rate of 210 gmai/ha.

Figure 4:
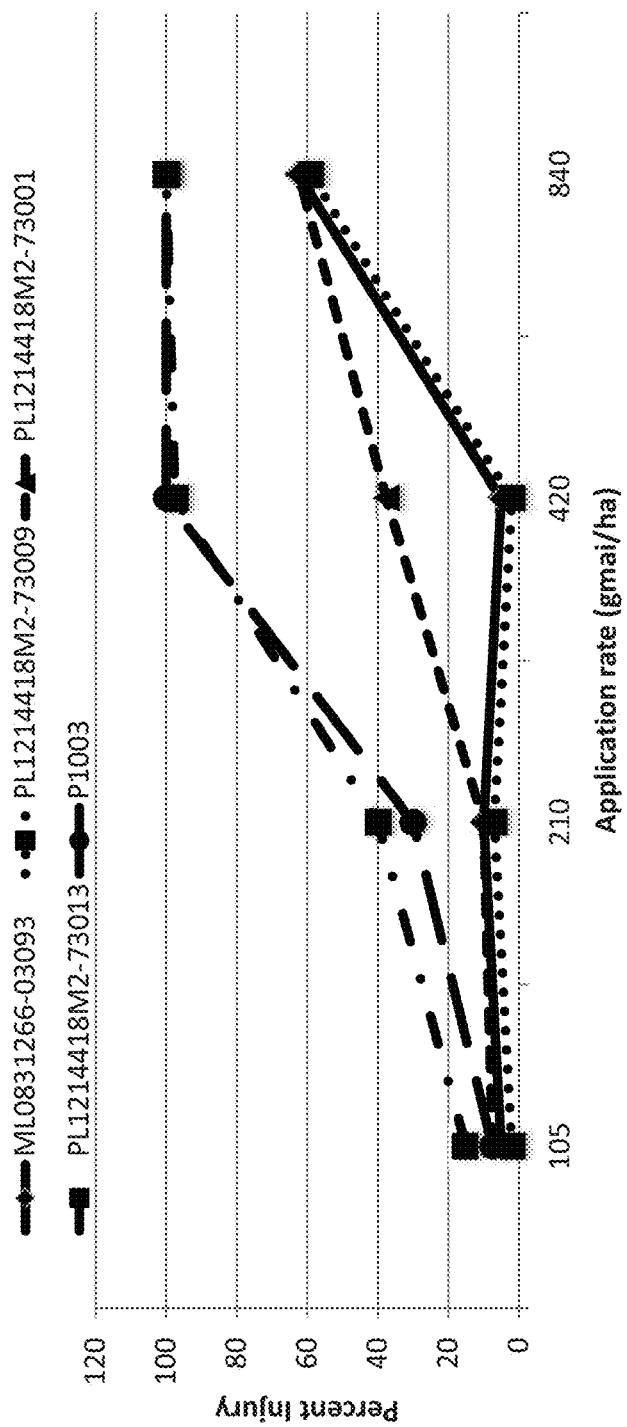
FIG. 4 is a graphical representation of results of a trait tolerance trial wherein mesotrione was applied at the indicated rates about 34 days after planting. (initiating tillering) the rice was evaluated for the percent of injury or damage as compared to unsprayed rice four weeks after herbicide application; the HPPD tolerant line ML0831266-03093 and the line with combined HPPD and ACCase tolerance PL1214418M2-73009 show a similar response indicating the full HPPD tolerance was recovered in the new line; the line PL1214418M2-73001 was selected to only carry the HPPD tolerant mutation from the HPPD line ML0831266-03093 and the line PL1214418M2-73013 was selected to only carry the HPPD non-induced tolerance from the HPPD line ML0831266-03093; P1003 is the non-mutant parent line for the HPPD tolerant line ML0831266-03093; note that over 420 gmai/ha, even the lines with genetic resistance may be injured.

The plots were evaluated 4 weeks after the herbicide was applied. The results showed that the native tolerance gene alone (PL1214418M2-73013) gave tolerance levels similar to the parent line P1003 (FIG. 4). This result would be expected if the native tolerance gene located on chromosome 2 located within the QTL flanking markers is the only causative source of tolerance in the non-mutant line P1003. The line PL1214418M2-73001 that carries only the HPPD mutation located on chromosome 1 within the QTL flanking markers, shows intermediate tolerance between the non-mutant line P1003 and the HPPD mutant line ML0831266-0309. This result shows that the HPPD mutation provides not only enhanced tolerance but also a greater level of tolerance than the native tolerance gene. In addition it also suggests that the HPPD mutation functions independently of the HPPD native tolerance gene. The two genes also appear to function in an additive manner as only by combining the two in the new line PL1214418M2-73009 does the tolerance level become equivalent to the original mutant line ML0831266-0309.

Controlling Weeds and Red Rice in Rice Crops with ACCase Inhibitors and Mesotrione Herbicides (HPPD Inhibitors)

The herbicide activity or ability to control non-mutant rice, such as line R0146 and P1003, is a good predictor of how well the herbicides will control red rice or wild weedy rice in a rice crop. Red rice and wild weedy rice are very similar to rice, even with the ability to cross with rice. This similarity is the reason these weeds are so difficult to control in a rice crop. The mutant lines (ML0831265-01493, ML0831265-02283, ML0831266-03093, PL1214418M2-80048, and PL1214418M2-73009) disclosed offer a new weed control strategy for red rice, wild weedy rice, and other weeds common in rice crops. These lines give rice tolerance to herbicides that will normally kill or cause yield reducing injury to the rice crop.

While testing the tolerant lines, the parent lines were also tested to serve as controls and as an indication of commercial potential as a red rice/wild weedy rice control strategy. These trials showed that select treatments of the herbicides applied alone or in various combinations and application timings offer a new weed control strategy in rice crops.

Figure 5:
FIG. 5 illustrates grass weed control by the ACCase inhibitor quizalofop; control is shown by the prevalent grass weed (dead plants) being killed by quizalofop (77 gm ai/ha) while the resistant line ML0831265-01493 (live plants) were not injured.
Figure 6A:
FIG. 6A-6B is a photograph of results of trait tolerance trials; weed control by mesotrione herbicide applied pre-planting was evaluated; the plots were planted with a hybrid of the HPPD tolerant line ML0831266-03093; just before planting, the plot on the right FIG. 6B received an application of mesotrione at 210 gmai/ha; the plot on the left FIG. 6A had no herbicide applied either pre-plant or post-emergence; pictures were taken four weeks after planting showing differences in weed appearance.
Figure 6B:
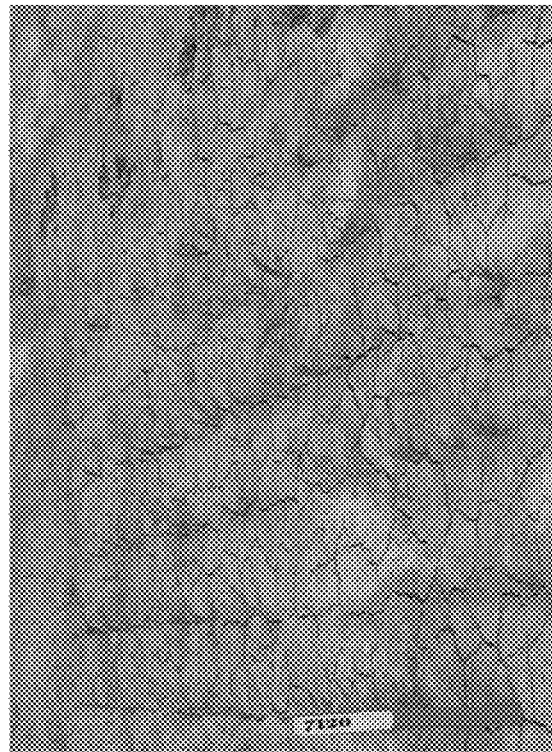

Rice is tolerant to certain ACCase inhibitor herbicides, for example cyhalofop is registered for use in rice. However other ACCase herbicides kill or severely injure rice to varying degrees. After testing, several of these other herbicides including fluazifop and quizalofop were found to offer good control of common grass weeds, such as barnyard grass, in rice (FIG. 5). Control of common weeds in rice was also achieved with mesotrione alone, especially when applied pre-plant or at higher rates (2× the labeled rate of 210 gmai/ha) (FIG. 6A and FIG. 6B). The applied rates of both types of herbicides giving the weed control are well within the tolerance level of the respective ACCase and HPPD tolerant lines including the combined lines carrying tolerance to both HPPD and ACCase herbicides.

Figure 7A:
FIG. 7A-7B is a photograph of rice growth versus stunted growth in a trait tolerance trial; both plots have rice line P1003 (carries some non-induced tolerance to HPPD herbicides); the herbicide treatments were applied at the initiation of tillering; the pictures were taken four weeks after herbicide application; only the ACCase herbicide fluazifop was applied to the plot on the left FIG. 7A (210 gmai/ha); at this rate fluazifop was not as active, no killing of the rice plants was observed; the right plot FIG. 7B was sprayed with a tank mixture of the ACCase herbicide fluazifop (210 gmai/ha) and the HPPD herbicide mesotrione (210 gmai/ha); combining herbicides improves activity.
Figure 7B:
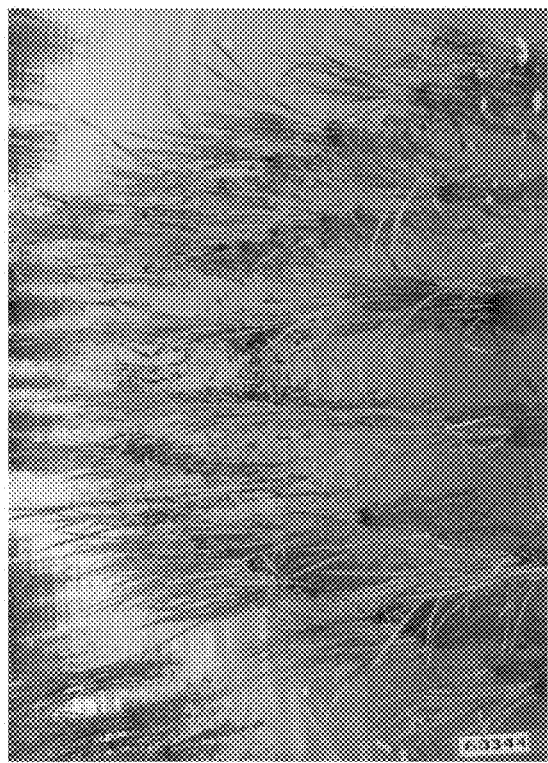

Development of the HPPD and ACCase tolerance into single lines (PL1214418M2-80048 and PL1214418M2-73009) gives the opportunity for an additional weed control strategy involving applications of ACCase and HPPD herbicides in a tank mix or individually at different times. The very effective pre-plant application of the HPPD herbicide mesotrione can now be followed with ACCase herbicides applied alone or in in combination with HPPD herbicides. This strategy provides full spectrum weed control in a rice crop by broad leaf weed control provided by the HPPD herbicide, and grass weed control by the ACCase herbicide. In addition the control of grasses and red rice/weedy rice by ACCase herbicides is greatly enhanced by the activity provided by the HPPD inhibiting herbicide. This strategy is anticipated as being especially effective for control of red rice when an ACCase inhibiting herbicides are used that have lower activity on rice (FIG. 7A and FIG. 7B).

This particular weed control system is highly useful in rice crops due to some weeds, including red rice, developing tolerance to currently used herbicides. Use of this weed control strategy allows rotation of different modes of action herbicides in rice crops. By rotating different modes of herbicide action the development of resistant weeds is slowed or prevented allowing for longer term use of all available weed control methods.

Figure 8:
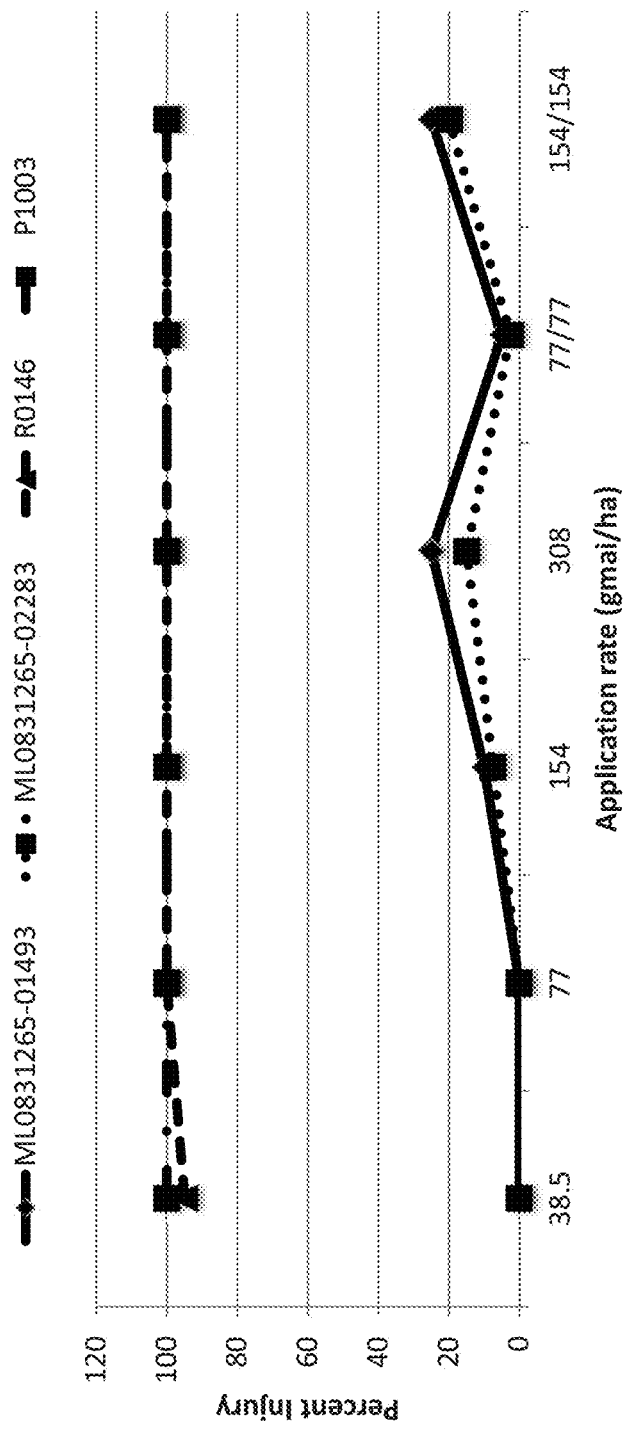
FIG. 8 is a graphical representation of results of a trait tolerance trial quizalofop was applied at the indicated rates about 30 days after planting (3-4 leaf stage), and a second application was applied on the two indicated treatments. The rice was evaluated for the percent of injury or damage as compared to unsprayed rice twenty-one days after the first herbicide application; line ML0831265-01493 is the ACCase tolerant line with the G2096S mutation; line ML0831265-02283 is also tolerant to ACCase herbicides however the tolerance is not from a mutation in the ACCase coding gene, R0146 is the parent line for both of the ACCase tolerant lines; P1003 is a control line.

Tolerance/Resistance to ACCase Inhibitors
1. Validation of the Mutant Line ML0831265-02283 for Tolerance to ACCase Herbicides After screening a large mutant population, the line ML0831265-02283 also survived application of the ACCase herbicide quizalofop. The line was increased to obtain sufficient seed for larger trials to evaluate its tolerance to ACCase herbicides. The tolerance to ACCase herbicides in line ML0831265-02283 was validated by planting in the field plots (5 feet by 10 feet) of the line, the non-mutant parent line R0146, a second non-mutant line P1003, and the ACCase tolerant line ML0831265-01493. The ACCase herbicide quizalofop was applied at the four leaf stage at 0.5×, 1×, 2×, and 4× multiples of the labeled rate (77 gmai/ha). Twenty one days after the herbicide was applied the plots were evaluated for percent injury caused to the rice based on control plots that had no herbicide application (FIG. 8). The data confirms the tolerance of line ML0831265-02283 and it may even carry more tolerance than line ML0831265-01493 as shown by less injury at the 2× and 4× rates of quizalofop.

2. Identification of the Causal Mutation for Tolerance to ACCase Herbicides in Line ML0831265-02283

Often tolerance to ACCase herbicides is derived from a mutation in the carboxyl transferase region of the ACCase gene, as is the case in tolerant line ML0831265-01493 (mutation at G2096S). However after sequencing the carboxyl transferase region of the ACCase gene in line ML0831265-02283 no mutation was found. This result indicates that the tolerance in line ML0831265-02283 is derived from a non-target site process.

Finding the causal mutation for tolerance in line ML0831265-02283 involved linkage mapping and mutation mapping as ("mut mapping") described for finding the causal mutation and native tolerance for HPPD tolerance in line ML0831266-0309. (Wright et al., 2011)

Figure 9:
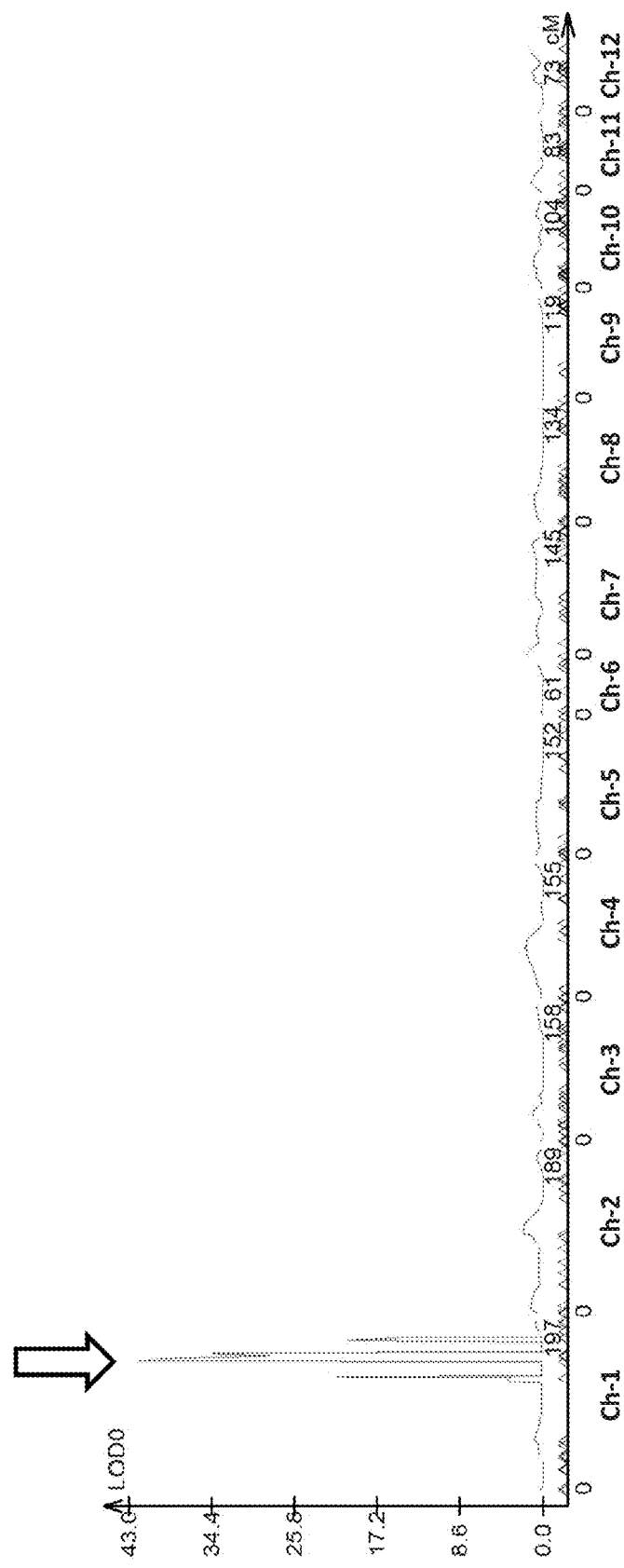
FIG. 9 shows results of a trait mapping experiment; an F2 population was derived from a cross between a cytoplasmic male sterile line A0109 and the ACCase tolerant line ML0831265-02283; the F2 individuals in the population were genotyped, sprayed with quizalofop (116 gmai/ha) twenty-six days after planting, and evaluated for tolerance to quizalofop nineteen days after herbicide application; using QTL mapping software, a major QTL for tolerance was identified on chromosome one (indicated by the arrow).

Linkage mapping to find the chromosomal region or QTL causing the tolerance in line ML0831265-02283 requires a population segregating for the trait. This population was made by crossing the tolerant line with the male sterile cytoplasm line A0109. The F1 collected from this cross was grown and allowed to self-pollinate to make a F2 population. The F2 population will segregate for ACCase tolerance. Eight hundred F2 seeds were planted and leaf tissue was collected from the seedlings to allow genotyping of each plant. When the seedlings where three weeks old the whole F2 population was sprayed with quizalfop (116 gmai/ha). The seedlings were evaluated for tolerance nineteen days after the herbicide application. Standard QTL mapping software was used to analyze the genotypes of each F2 individual and the associated tolerance response to identify molecular markers linked to the herbicide tolerance. After this analysis a genomic region (QTL) was identified for the tolerance on chromosome one (FIG. 9). Linked markers flanking the QTL and markers inside the QTL flanking the peak of the QTL were identified as being suitable to select the herbicide tolerance derived from line ML0831265-02283 (TABLE 5). Approximately 250 genes are between the flanking markers.

The mutation mapping strategy to find the causal mutation was employed in the same manner as used to find the QTL for HPPD mutation tolerance. A mutation mapping population was created to find the causal tolerance mutation through genomic sequencing by next-generation sequencing. The mutant line ML0831265-02283 was crossed back to the original non-mutant parent R0146. The F1 progeny of the cross were selfed to produce a F2 population that is segregating for the tolerance causing mutation. Only mutations are segregating in this population because the mutations are the only genomic difference between ML0831265-02283 and R0146.

The F2 population was planted as individuals, and leaf tissue was collected and DNA extracted from each individual to use for genotyping after the population was phenotyped. The ACCase herbicide quizalofop was applied to the F2 population at the 3-4 leaf stage and a concentration of 116 gmai/ha. Individuals that survived the herbicide application were scored as tolerant and those that died were scored as susceptible.

The DNA derived from a set of twenty surviving F2 individuals and twenty that were killed was each respectively bulked together and sequenced along with both the mutant line ML0831265-02283 and the non-mutant parent line R0146. Mapping the causal mutation was based on an index accessing the frequency of all mutations in the bulk representing the surviving individuals. The index was derived from the proportion of sequencing reads that carried a variation different from the non-mutant parent line R0146. The more sequencing reads with the variation the closer the index was to one and if all sequencing reads had the variation the index equaled one.

Figure 10:
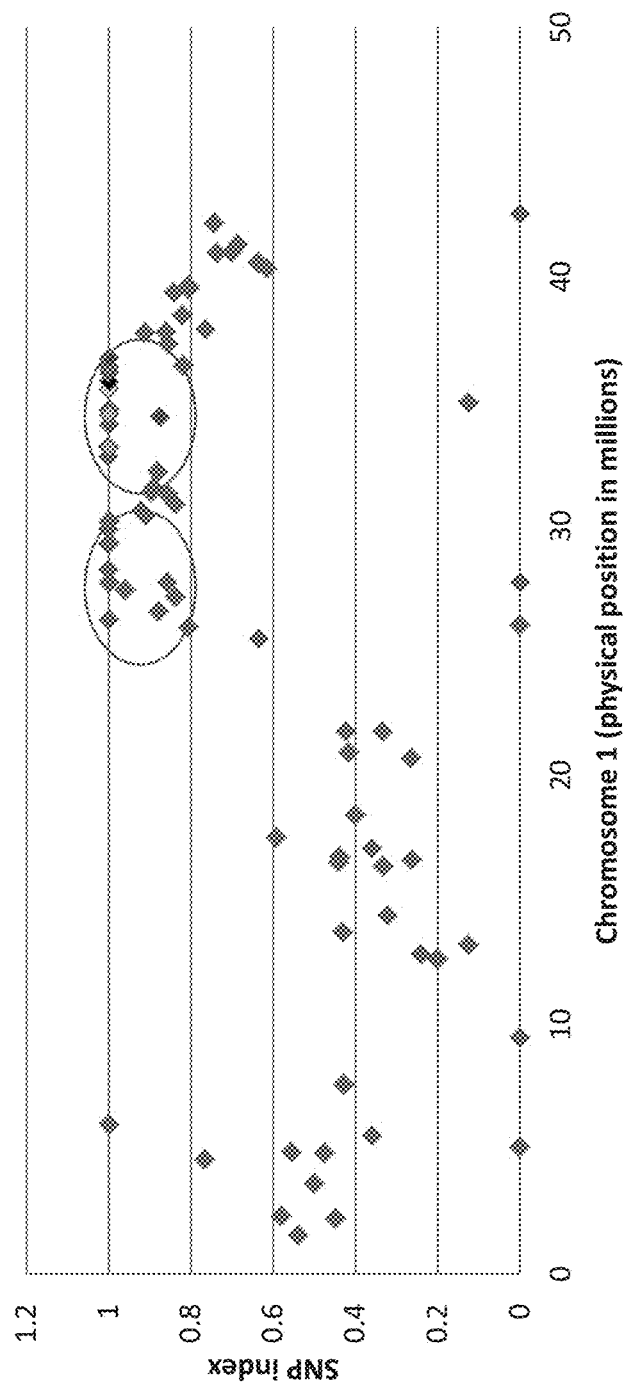
FIG. 10 is a scattergram showing results of a mutation mapping experiment; an F2 population was derived from a cross between the ACCase tolerant line ML0831265-02283 and the parent line R0146; the F2 population was genotyped, sprayed with quizalofop (116 gmai/ha), and evaluated for resistance to quizalofop; only mutations including ACCase resistant mutations will be segregating in the population; the SNP index is a measure of the proportion of sequencing reads that carry a variation from the non-mutant line R0146; a score of one indicates that all sequencing reads had the variation; 19 variations (mutations) had an index of one and grouped together on chromosome one (circled) indicating the probable location of the tolerance causing mutations. (SEQ ID NOs: 208-226)

The analysis of these results showed two groups including 19 mutations of eleven mutations on chromosome one with an index score of one (FIG. 10). This result confirms the QTL linkage mapping results as the mutations identified here all are located within the QTL region identified on chromosome one by linkage mapping. Molecular markers (SNP) were made for each of the mutations (TABLE 6). These markers are used in fine mapping to find the causal mutation and for breeding the ACCase tolerance derived from line ML0831265-02283 into commercial rice lines.

Tolerance/Resistance to HPPD Inhibitors: Herbicide Screening

Mesotrione (Callisto®), is an herbicide that inhibits the plant enzyme 4-hydroxyphenylpyruvate dioxygenase (HPPD). Callisto® is a postemergent and preemergent herbicide used to control annual broadleaf weeds in corn and certain other crops. The herbicide only damages some rice at lower rates but kills other types of rice. All rice appears to be at least damaged by higher herbicide rates. Finding resistance to Callisto® herbicide in rice results in a new mode of action for controlling broadleaf weeds and some grasses, in rice.

Resistance to mesotrione herbicide was found by screening the permanent mutant population. All lines in the permanent mutant population were planted into a dry seed bed. Within twelve hours after planting mesotrione (Callisto®) was applied at a rate of 255.1 gm ai per acre. The field was immediately flushed with water and kept moist through periodic flushing. The seedlings grew, many were bleached white and all lines derived from R0146 died whereas plants lived from 21 lines derived from the P1003 and 2 derived from P1062 mutation populations. The HPPD gene was sequenced, and no genetic mutation was identified causing any amino acid substitutions (SEQ ID NOs: 1, 2, 3).

Figure 19A:
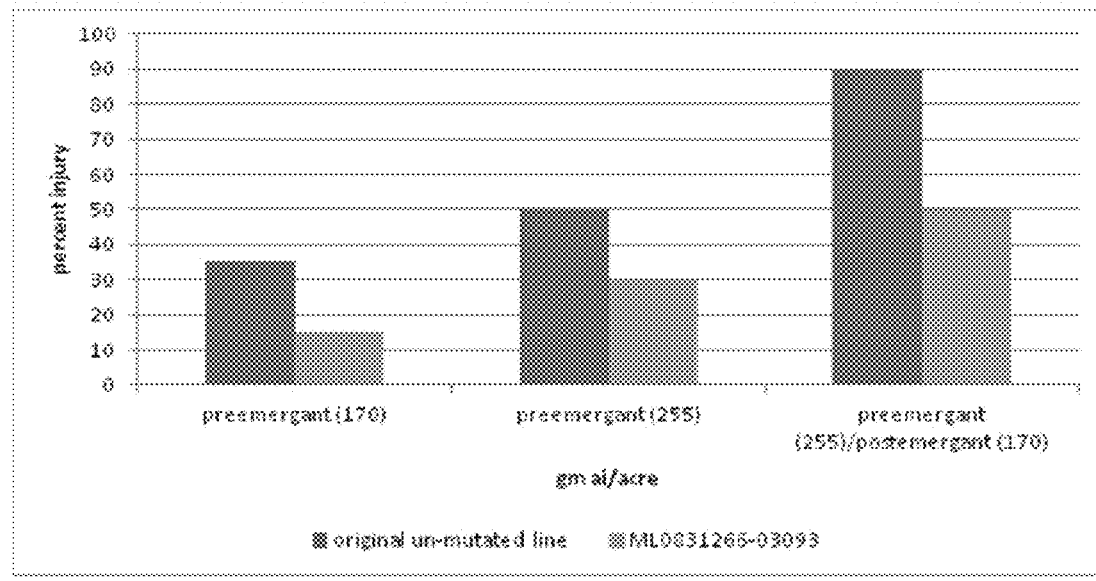
FIG. 19A and FIG. 19B illustrate rate response of the mutant line ML0831266-03093, the unmutated original (parental) line P1003, and a different type of rice R0146; mesotrione was applied across all plots immediately following planting at a rate of 210 gai/ha; the response rates were applied at the 2-3 leaf stage; response was recorded twenty-one days following the foliar application.
Figure 19B:
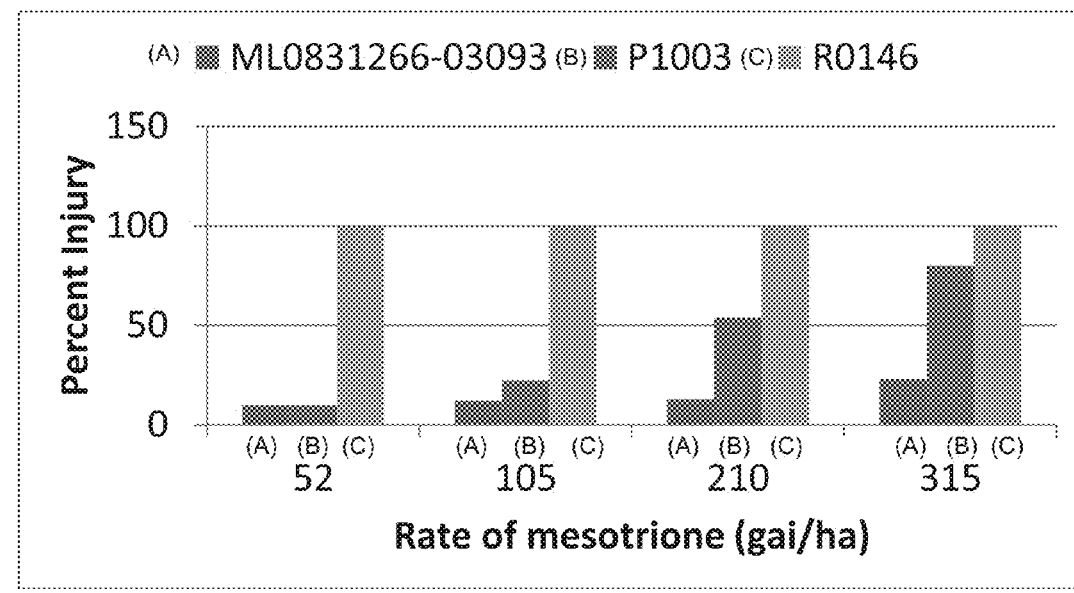

Validating the Mutant Line ML0831266-03093 for Tolerance to HPPD Inhibiting Herbicides After the initial screening of the "mutation population," the lines with no damage were selected and tested in additional experiments using different rates of the herbicide. In particular, a rate response experiment was conducted in which two different rates of mesotrione were applied pre-emergence, plus an additional foliar application was also applied. This experiment differentiated one mutant line as having superior resistance (less injury) to the mesotrione herbicide as compared to the control (FIG. 19A and FIG. 19B, Table 1). Progeny of this designated ML0831266-03093 are maintained as a new line carrying resistance to mesotrione herbicide. Seeds are deposited under ATCC PTA-13620. The line (ML0831266-03093) is a source of resistance that is backcrossed into proprietary rice lines or used directly in breeding to develop new proprietary rice lines. The developed lines are a source of herbicide resistance for use in development of new hybrids that offer an alternative mode of action to control weeds in rice. Affording this opportunity to growers is of great value both in providing high yields and in extending the useful life of available weed control technologies. These herbicide resistant traits can be tracked through the simple application of herbicides to growing plants.

The mutant line ML0831266-03093 was found to carry tolerance to mesotrione (a common HPPD inhibiting herbicide) through screening the line with different rates of the herbicide. The tolerance level of ML0831266-03093 was found to be much greater than the original non-mutant (native) line P1003.

Figure 11:
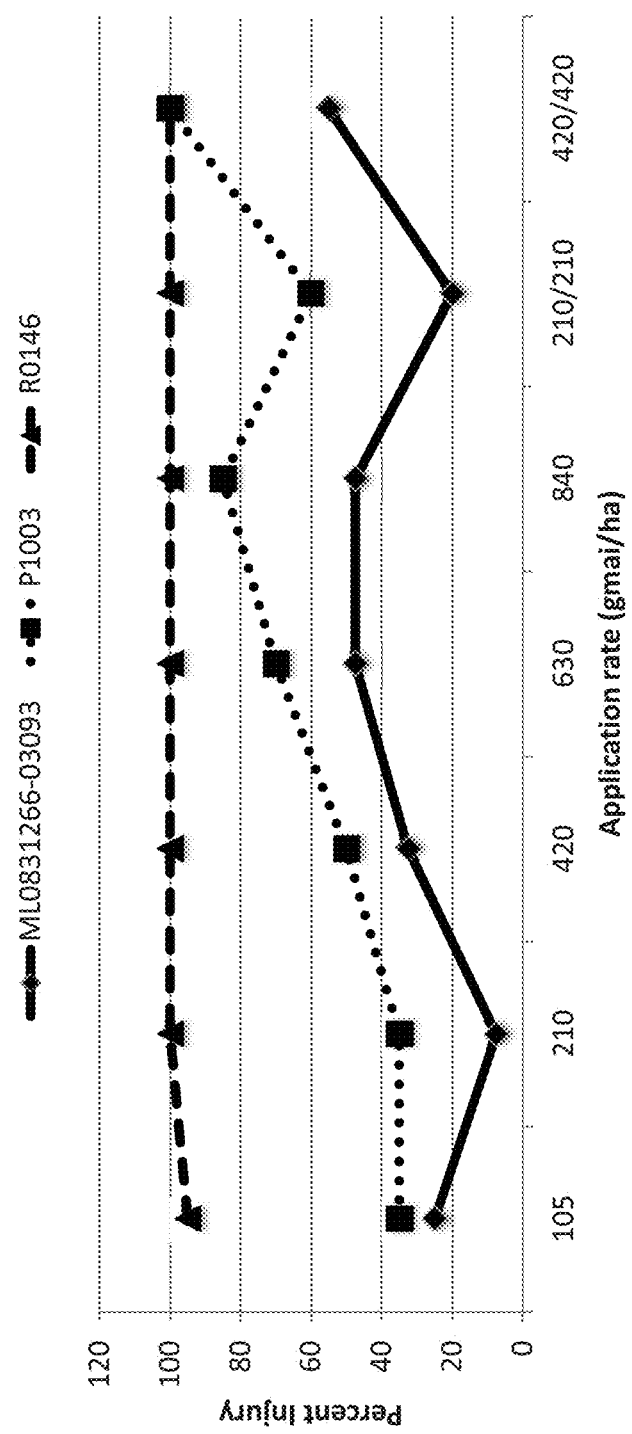
FIG. 11 shows graphical results of HPPD trait tolerance trials; mesotrione was applied at the 3-4 leaf stage of rice (ML0831266-03093; P1003 and R0146) and evaluated twenty-one days after application for response to the herbicide; the rice was evaluated for the percent of injury or damage [see DEFINITIONS] as compared to unsprayed rice; the last two treatments included a sequential application two weeks after the first application.

The original line P1003, carries natural tolerance to mesotrione. This non-induced resistance of the original line sometimes masked the resistance of the mutant line making the enhanced resistance of the mutant line ML0831266-03093 not obvious. Finding the value of the mutant line ML0831266-03093 was only achieved with careful testing over two years, in different locations, and using different rates and timings of herbicide application. The high tolerance of the mutant line ML0831266-03093 is now apparent and documented through a rate response trial measuring the response of line ML0831266-03093 and non-mutant control lines to different rates of mesotrione (FIG. 11).

Figure 12:
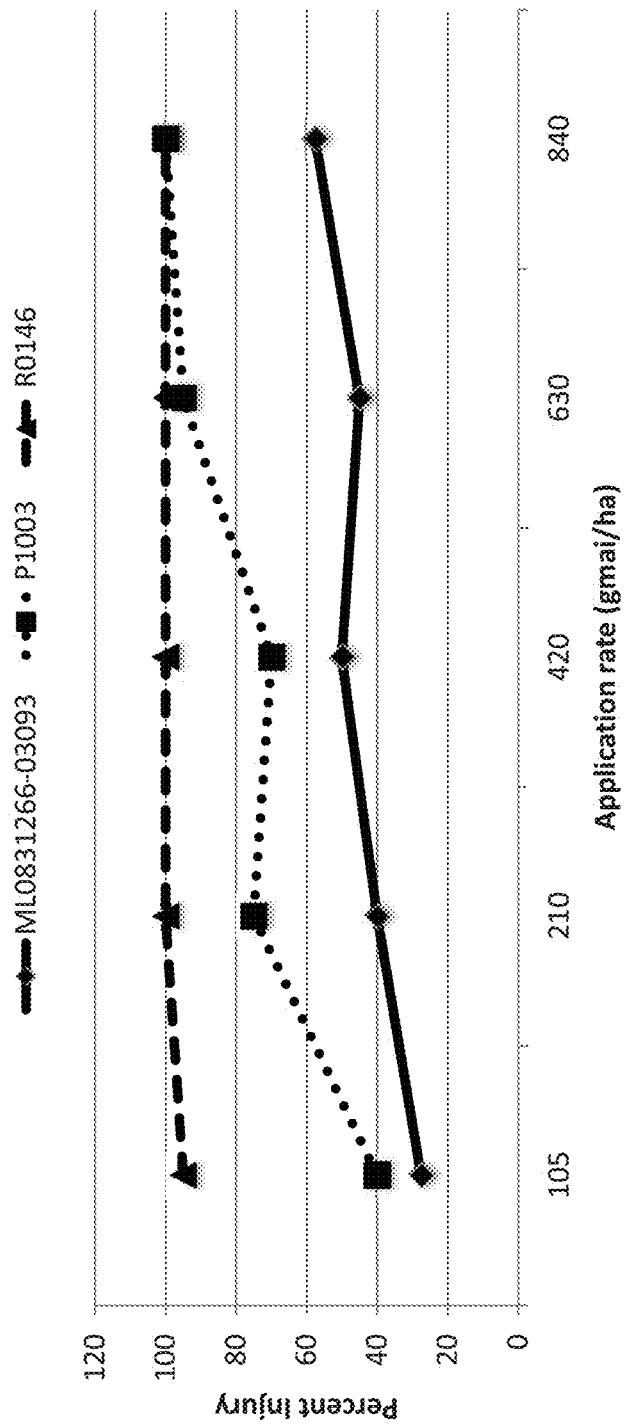
FIG. 12 shows graphical results of HPPD trait tolerance trial; a pre-plant application of mesotrione was applied (ML0831266-03093; P1003 and R0146) at 210 gmai/ha followed by post-emergent mesotrione applications at the 3-4 leaf stage at the indicated rates; the rice was evaluated for the percent of injury or damage as compared to unsprayed rice twenty-one days after the post-emergent application.

The validating trials included testing applications of mesotrione applied just before planting (pre-plant applications), after planting at various stages of rice growth (post applications), and combinations of both pre-plant and post applications. The discovered tolerance to HPPD inhibiting chemicals was apparent for both pre-plant and post-emergent applications (FIG. 12). The mutant line ML0831266-03093 shows tolerance greater than natural rice has to HPPD herbicides in all application regimes.

Further validation of the trait involved testing the mutant line ML0831266-03093 in the presence of common rice weeds. The mutant line was completely tolerant to the applied rates of mesotrione whereas the prevalent weed population was well controlled by the herbicide (FIG. 6A and FIG. 6B). This level of grass weed control was completely unexpected as mesotrione is labeled for controlling broadleaf weeds in monocot crops. This result indicates that mesotrione and other HPPD inhibiting herbicides in combination with line ML0831266-03093 and derived lines, represent a new weed control system in rice. The high activity of the mesotrione on grass weeds and certain types of rice indicates that the system could be used to control red rice in a rice crop.

Mesotrione and other HPPD inhibiting herbicides target the HPPD gene. An increase in herbicide tolerance could be achieved through a mutation in the HPPD gene. A mutation within the gene sequence can alter the enzyme structure sufficiently to prevent it from being inhibited by the herbicide, but still allow it to carry-out its normal physiological function. Assuming this as a plausible tolerance mechanism, the HPPD gene was sequenced by Sanger sequencing in both the mutant line ML0831266-03093 and the original line P1003. Surprisingly, no mutation was found in the HPPD gene (SEQ ID NO: 1). The herbicide tolerance in line ML0831266-03093 appears to be derived from a non-target site process.

Two different methods were used to find the tolerance causing mutation. The first method involved using a QTL mapping strategy only employing a unique phenotyping process to find both the tolerance causing mutation and the gene causing the natural tolerance. The second method involved sequencing the entire genome of F2 plants derived from a cross to the non-mutant parent. [P1003]

1. QTL Mapping to Find the Causal Mutation and the Natural Tolerance Causing Gene The mutant line ML0831266-03093 contains high tolerance to mesotrione and possibly other HPPD inhibiting herbicides, due to both a new mutation and a native tolerance gene present in the original non-mutant line P1003. The mesotrione tolerant line ML0831266-03093 was crossed to another mutant line ML0831265-01493. This second mutant line ML0831265-01493 lacks the native tolerance gene and is highly susceptible to mesotrione. However line ML0831265-01493 does have tolerance to ACCase herbicides due to a mutation in the ACCase gene that changes amino acid 2096 from glycine to serine. This mutation alters the enzyme making it unaffected by certain ACCase herbicides, however it still retains its normal physiological function. The mutation site for change the amino acid 2096 most commonly arises in weeds as a change to alanine rather than the only rarely found serine change. (FIGS. 20, 21) A molecular marker was developed based on the sequencing information, to test for inheritance of the mutation G2096S.

The F1 progeny from the cross of line ML0831266-03093 to ML0831265-01493 was selfed to produce a large population of F2 individuals. Each F2 individual was genotype with a set of 192 SNP markers (Table 3) that were polymorphic between the parents, to fully cover the genome with molecular markers.

Figure 13:
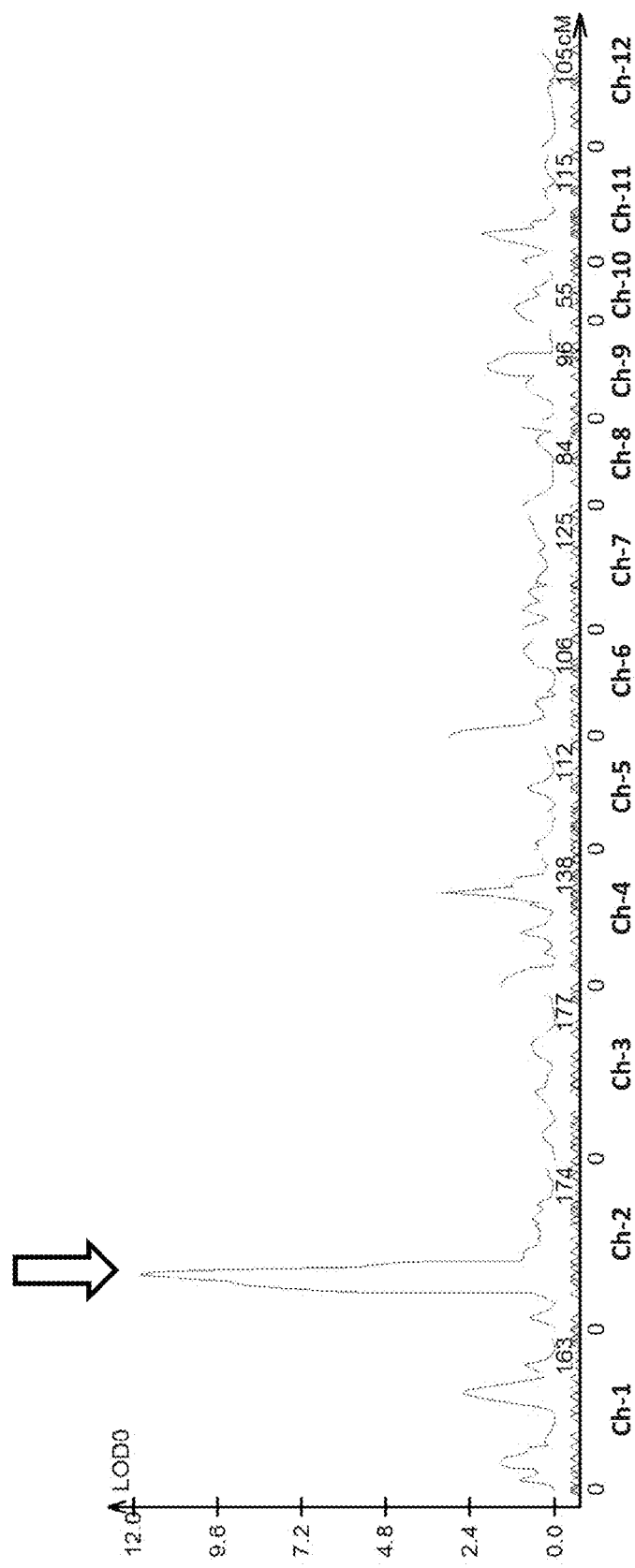
FIG. 13 graphically represents results of trait mapping experiments; an F2 population was derived from a cross between the HPPD tolerant line ML0831266-03093 and the ACCase tolerant line ML0831265-01493; the population was genotyped, sprayed with mesotrione at 105 gmai/ha, and evaluated for tolerance to mesotrione; plants inheriting either the non-induced tolerance or the mutation tolerance from parent line ML0831266-03093 were expected to live; using QTL mapping software, a major QTL for tolerance was identified on chromosome two (indicated by the bold arrow). (X axis=chromosome number in the genome; Y axis=score, correlation with phenotype (resistance)).
Figure 14:
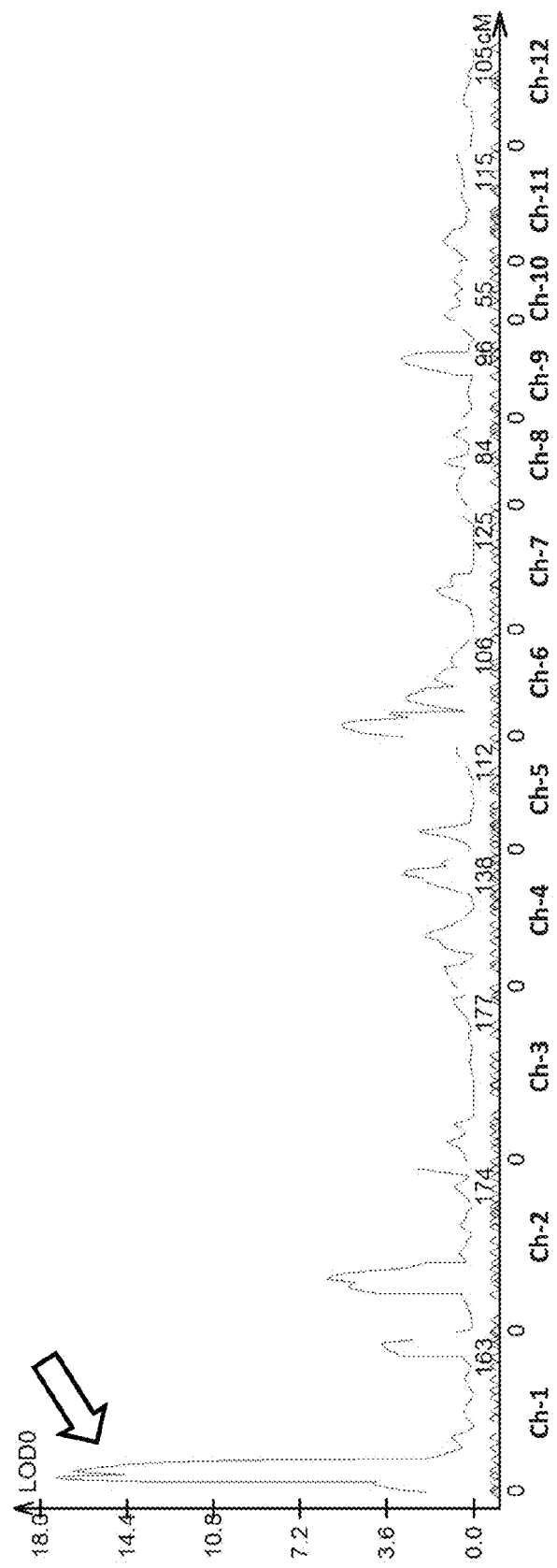
FIG. 14 graphically represents results of trait mapping experiments; an F2 population was derived from a cross between the HPPD tolerant line ML0831266-03093 and the ACCase tolerant line ML0831265-01493; the population was genotyped, sprayed with mesotrione at 105 gmai/ha, evaluated for tolerance to mesotrione, and sprayed again with mesotrione at 630 gmai/ha, and evaluated for tolerance to mesotrione; only plants inheriting the mutation for tolerance from parent line ML0831266-03093 were expected to live; using QTL mapping software a major QTL for tolerance was identified on chromosome one (indicated by the arrow) (X axis—chromosome number in the genome; Y-axis=score, correlation with phenotype).

Next in a QTL mapping strategy was to spray the herbicide on the F2 individuals and observe those that survive. However, this strategy could introduce complications due to both the native tolerance gene and the tolerance mutation segregating. A different strategy was used in which first mesotrione was applied at a low rate (105 gmai/ha). At this rate all plants inheriting the tolerance causing mutation, the native tolerance, or both, survived, whereas plants inheriting the corresponding genomic regions from the line ML0831265-01493 died as they are highly sensitive to the herbicide. QTL analysis based on this phenotyping method identified one QTL located on chromosome 2 (FIG. 13). After phenotyping the F2 plants with a low application rate of mesotrione a second high rate (630 gmai/ha) was applied, and the plants were again phenotyped. After analysis, a second QTL was found on chromosome 1 representing the higher tolerance achieved from the tolerance mutation (FIG. 14). With this strategy the two genes were resolved, one of which is the mutation (chromosome 1) and the other the native tolerance (chromosome 2).

Based on the QTL positions and linked markers a set of markers was identified that flank the mutation and native tolerance QTLs (TABLE 4). These markers define the region containing the HPPD tolerance causing genes. In addition this set of markers can be used for breeding purposes to develop new lines carrying tolerance to HPPD herbicides. The use of these markers allows selection without having to apply the herbicide to breeding populations.

2. Mutation Mapping to Find the Tolerance Causal Mutation

A mutation mapping population was created to find the tolerance causal mutation through genomic sequencing by next-generation sequencing. The mutant line ML0831266-03093 was crossed back to the original non-mutant parent P1003. The F1 progeny of the cross was selfed to produce a F2 population that will be segregating for the tolerance causing mutation. Only mutations will be segregating in this population because the mutations are the only genomic difference between ML0831266-03093 and P1003.

The F2 population was planted as individuals and leaf tissue collected and DNA extracted from each individual to use for genotyping after the population was phenotyped. In this method all of the population will carry the native tolerance gene rendering the population tolerant to a certain level to mesotrione herbicide. To differentiate the native tolerance from the tolerance causal mutation mesotrione was applied to the population with a high rate (840 gmai/ha) so that all individuals without the tolerance causal mutation died.

The DNA derived from a set of twenty surviving F2 individuals and twenty that were killed was each respectively bulked together and sequenced along with both the mutant line ML0831266-03093 and the non-mutant parent line P1003. Mapping the causal mutation was based on an index accessing the frequency of all mutations in the bulk representing the surviving individuals. The index was derived from the proportion of sequencing reads that carried a variation different from the non-mutant parent line P1003. The more sequencing reads with the variation the closer the index was to one and if all sequencing reads had the variation the index equaled one.

Figure 15:
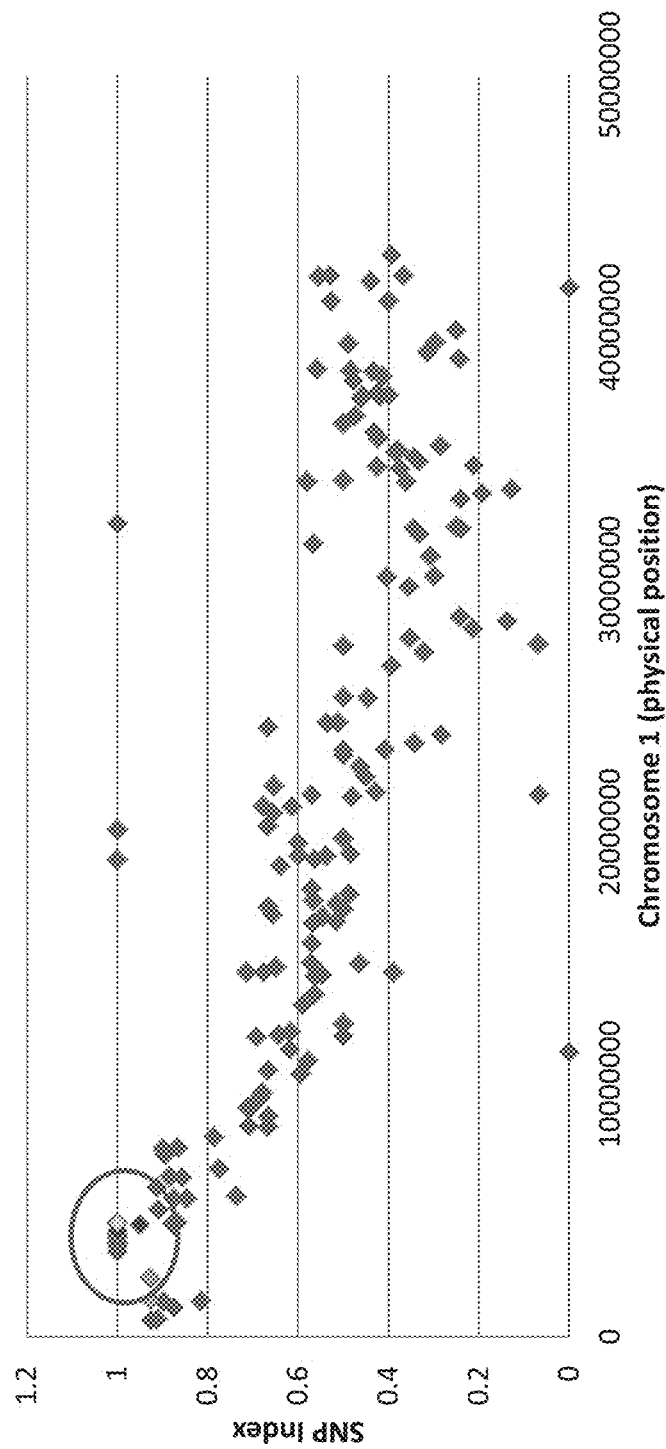
FIG. 15 shows results of mutation mapping experiments; an F2 population was derived from a cross between the HPPD tolerant line ML0831266-03093 and the parent line P1003; the population was genotyped, sprayed with mesotrione at 840 gmai/ha and evaluated for tolerance to mesotrione; only mutations including the HPPD tolerant mutation segregate in the population; the SNP index is a measure of the proportion of sequencing reads that carry a variation from the line P1003; a score of one indicates that all sequencing reads had the variation; ten variations (mutations) had an index of one and grouped together on chromosome one (circled) indicating the probable location of the tolerance causing mutation. (SEQ ID NOS: 227-236)

A single mutation causing the high tolerance to mesotrione was predicted. Instead the data showed a peak of mutations carrying a score of 1 introducing another level of difficulty in finding the causal mutation. The result did confirm that the QTL on chromosome 1 found through linkage mapping is the genomic location of the tolerance casual mutation (FIG. 15). Within the peak of mutations we found seven mutations with an index of one, none of which are an obvious cause for tolerance to mesotrione herbicide. (TABLE 7) Markers were developed for the mutations to facilitate finding the casual resistance mutation(s).

Figures 16A, 16B:
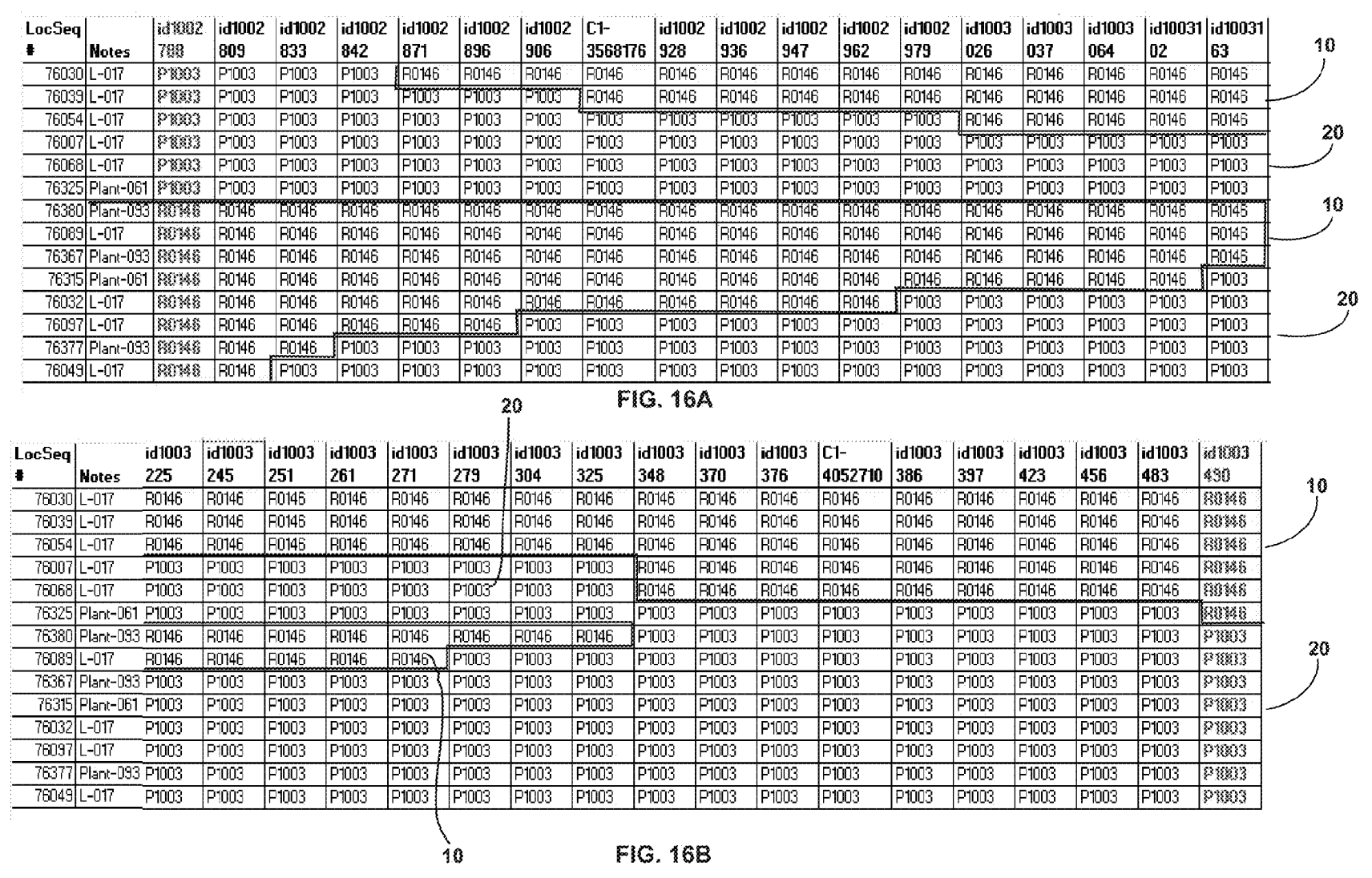

A set of lines was identified with recombination points evenly distributed within the identified QTLs and mutations (FIG. 16A, 16B, FIG. 17). These lines were recovered in a homozygous condition for each recombination allowing phenotyping for herbicide tolerance on multiple individuals (full plots). Analysis of these lines allowed the tolerance mutation and native gene to be narrowed to a small region of the chromosome.

Through the described strategy the specific genomic regions containing the tolerance causal mutation and the native tolerance gene are now known and useful for developing commercial products. The commercial products are useful in rice production as they survive application of mesotrione herbicide at rates that will control prevalent weeds including red rice without harming the rice crop. The specific genomic location allows the use of molecular markers on the flanking regions of each QTL to select for the HPPD tolerant trait in the development of commercial products.

Genetic mapping of the three groups of F2 individuals including the set of individuals sprayed with mesotrione at only 105 gm ai/ha, the set followed by a sequential application of 630 gm ai/ha, and the final group sprayed with 420 gm ai/ha shows two genes controlling resistance to mesotrione. In the population sprayed with 105 gm ai/ha a single QTL found on chromosome 2 with strong linkage to SNP marker BG-id2004662 acted in a mostly dominate manner. This marker and QTL identifies the inherent tolerance in line P1003. The marker is useful for breeding and selection of new mesotrione tolerant lines. The discovery of this QTL facilitates commercial development of new rice varieties with a new method for controlling weeds through the use of mesotrione herbicide. The finding of the linked marker BG-id2004662 is a novel finding and selection strategy for breeding and selecting the tolerance to mesotrione and other herbicides derived from line P1003.

Figure 24:
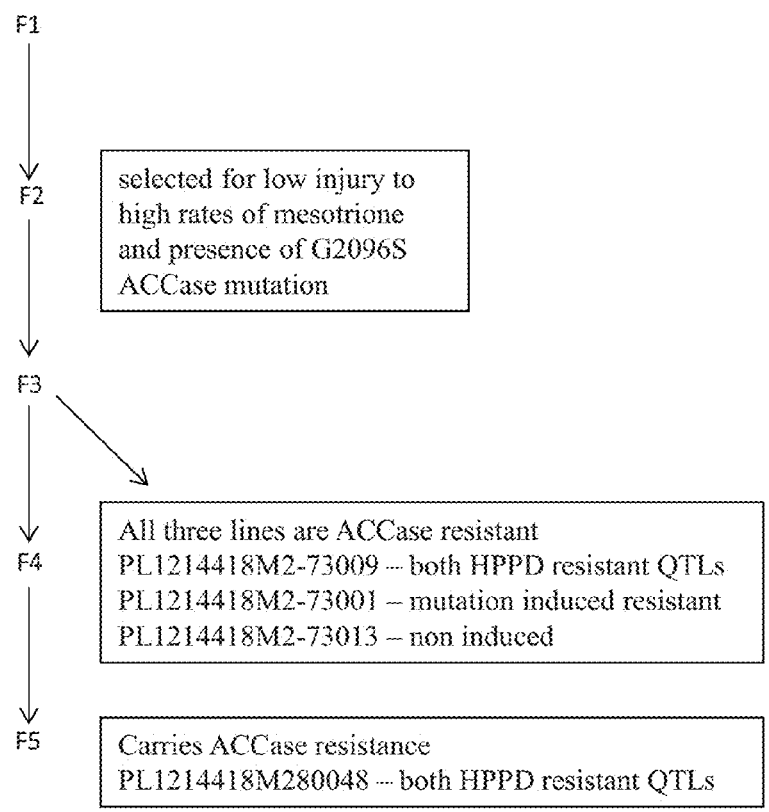
FIG. 24 is a flow chart of a type of cross used in some embodiments disclosed herein.

In the two groups of F2 individuals sprayed with the higher rates of mesotrione (420 and 630 gm ai/ha) a second QTL was found with strong linkage to SNP marker WG-id1002788. This QTL is the demonstrated genetic position of the causal mutation for high tolerance to mesotrione. The combined tolerance of the QTL developed through mutation breeding on chromosome 1 and the QTL discovered in line P1003 provides a novel tolerance to mesotrione and combined with the linked molecular markers facilitates quick and efficient breeding of new rice varieties (FIG. 24).

Genetic mapping for the genomic location for resistance in line ML0831266-03093 is carried out by common QTL mapping strategies. The resistant line ML0831266-03093 may be crossed with a highly sensitive line and the resulting F1 seeds grown and plants selfed to produce a F2 mapping population segregating for the resistance trait. Finding trait linked markers is done by genotyping each F2 plant, spraying the plants with an appropriate concentration of the herbicide, and associating the molecular genotypes with the phenotype of each individual. This process will identify a genomic region between markers for the causal mutation for resistance.

Identifying the mutation causing the herbicide resistance is possible through a variety of processes. The mutant line and the original non-mutant line sequences are prepared and compared to identify mutations within the region of the QTL found through common trait mapping methods. Then markers are developed to the sequence differences, they are testing on a phenotyped segregating population such as the one used for QTL identification or make a new similar population. In another method, next generation sequencing is used to sequence and compare a bulk of individuals that are resistant to either a bulk of susceptible individuals or to the original non-mutant line. In this method the causal mutation is found through the resistant bulk having the highest portion of the mutation or sequence difference as compared to the susceptible bulk or non-mutant original line.

A recent publication for these methods includes Akira Abe, et al.; Nature Biotechnology 30, 174-178(2012) doi: 10.1038/nbt.2095, Published online 22 Jan. 2012.

EXAMPLES

Example 1: Production of Hybrid Rice Resistant to One HPPD Inhibiting Herbicide

The HPPD inhibiting herbicide resistance provided by ML0831266-03093 is deployed individually into hybrids through either the male or female parent resulting in the hybrid seed being resistant to the herbicide. If the resistance is deployed in only the male parent, then in addition to its use for weed control, the herbicide when applied to hybrid seed kills contaminating female selfed seed. On the other hand if the resistance is deployed only through the female parent, growers may eliminate contaminating male selfed seed.

Growers may alternate the type of resistance they purchase and apply in their fields to reduce the chance that weeds develop resistance to the herbicide. The HPPD inhibiting herbicide, though primarily for control of broad leaf weeds, also allows for some enhanced control of red rice. At higher rates it will kill certain types of rice. If resistance arose in red rice from cross pollination, it could still be controlled with a different herbicide class in the next season.

Example 2: Production of Hybrid Rice with High Level of Resistant to HPPD Inhibiting Herbicides The HPPD inhibiting herbicide resistance provided by ML0831266-03093 is deployed into both the male and female parents of a hybrid. The resulting hybrid seed may carry resistance to mesotrione and other HPPD inhibiting herbicides. Resistance provided in this manner is stronger and offers better weed control through the possibility of being able to apply higher rates of herbicide.

Example 3: Production of Hybrid Rice Resistant to Multiple Herbicides

The herbicide resistance for at least 2 herbicides is deployed in a single hybrid through making both the female and male parent resistant to both herbicides. Deployment in this manner results in hybrid seed being homozygous for both resistances. By providing resistance in homozygous condition in the hybrid for both herbicide classes the hybrid seed shows maximum level of resistance. In addition by deploying both resistances together, the grower has the option to select either herbicide to apply in a given season, alternatively, both herbicides could be applied within the same season. The ability to rotate herbicides provides the opportunity to extend the life of the herbicides through delaying the development of weed resistance. This method also allows for the use of both herbicide classes for weed control during hybrid seed production.

Example 4: Production of Hybrid Rice Resistant to Mesotrione and at Least One Other Herbicide Class 1. Resistance to mesotrione and at least one other herbicide class is deployed in a single hybrid by using a male parent that carries resistance to the mesotrione (or the other herbicide) and a female that carries the other resistance. The method allows the grower to make a single purchase but to be able to choose which herbicide to apply. A single class of herbicide may be used in any one season and rotated between seasons, or alternatively both herbicides could be applied within a single season. In addition, deployment by this method, elements contaminating selfed seed of both parents in the hybrid seed through application of both herbicides, or one type or the other, are eliminated through application of only one herbicide.

2. In another method of deployment the mesotrione resistance and any other herbicide resistance is deployed through making a hybrid with a male parent that carries both resistances. The grower then has the option to choose which herbicide class to apply or to apply both within a single season. In addition, through the application of either herbicide contaminating selfed female seed would be eliminated. Alternatively both herbicide class resistances are provided in the female parent, giving the grower the same options for weed control.

3. Another embodiment is to deploy the mesotrione resistance to both parents, and another herbicide resistance into only one parent, such as the male parent. The hybrid seed are then homozygous for the mesotrione resistance but not the other. A scheme like this is used to make an early application with the herbicide put into only the male parent, providing weed control and elimination of contaminating female selfs. Later in the season mesotrione may be applied or another HPPD inhibitor herbicide. The useful life of both herbicides is extended through limiting or eliminating the development of weed resistance. In another application this method allows the use of mesotrione or other HPPD inhibitor herbicide to control weeds in seed production fields, allowing for cleaner seed.

4. Alternatively a different herbicide could be deployed in both of the hybrid parents and the mesotrione/HPPD inhibitor is deployed in only the male parent.

5. Other embodiments for deploying herbicide resistant lines include other traits such as resistance to other classes of herbicides, or other traits of importance.

Example 5: Seed Production

The herbicide resistance is also used for seed production. As an example, if it is deployed into the female parent, making it resistant, the herbicide is applied to the seed production field to kill the male plants before setting seed so that a seed production field is harvested as a bulk. In addition the purity of the seed may also be verified through deploying two herbicide resistances with only one in each parent. Selfed seed is detected and eliminated by applying herbicide put into the other parent.

Example 6: Control of Broadleaf Weeds and Limited Control of Grasses

The resistance when deployed in a hybrid, by any combination, provides resistance to mesotrione or other HPPD inhibiting herbicides. This deployment results in a new mode of action in rice to control broadleaf weeds with some limited control of grasses such as red rice. Further options or broad spectrum control of weeds is provided by deployment in the same hybrid another resistance to herbicides providing grass weed control, such as ACCase inhibiting herbicides. Through deployment with other modes of action development of weed resistance is more likely to be prevented through the use of multiple modes of action.

Example 7: Selection of Herbicide Resistant Rice Using a Herbicide Bioassay

Figures 18A, 18B, 18C:
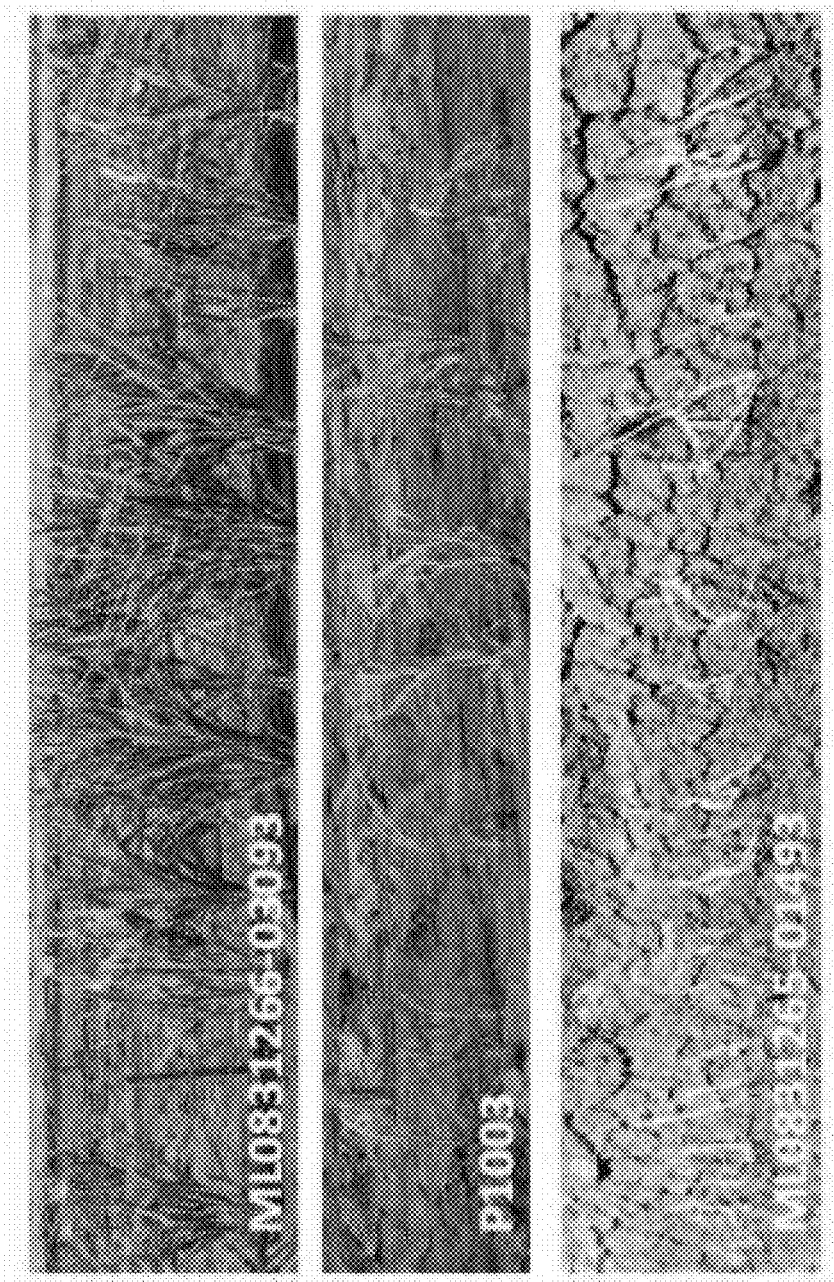
FIG. 18A, FIG. 18B, FIG. 18C are photographs of controls used in the mesotrione herbicide bioassay after spraying one application of mesotrione at 105 gai/ha followed by a second application of 630 gai/ha.

Selection of material inheriting mesotrione tolerance is accomplished by a simple herbicide bioassay. A high rate of mesotrione (at least 420 gm ai/ha) is applied allowing differentiation of heterozygous individuals from homozygous individuals and the tolerance level of the mutation line from the inherent tolerance level in the background of some types of rice. In one example a rate of 105 gm ai/ha is applied followed three weeks later by a second application of 630 gm ai/ha. In another example a rate of 420 gm ai/ha is applied in a single application. Yet another example entails applying the herbicide at a rate of 630 gm ai/ha. Herbicide applications are done at the three to four leaf stage of seedling growth. The ideal situation is to have also planted near or within the plants to be selected a set of plants from the original mutant mesotrione tolerant donor line ML0831266-03093, (FIG. 18A) a row of plants of the wild-type of the mutation line, P1003 (FIG. 18B), and a row of the line involved as the other parent in the cross (FIG. 18C). These control lines allow easy differentiation for inheritance of the tolerance provided by the ML0831266-03093 mutant line through comparison of the response in the plants to be selected with the control lines. Only plants that live and are relatively healthy will have inherited and be homozygous for the tolerance level provided by the ML0831266-03093 mutant line (FIG. 18A).

Example 8: Production of Rice Resistant to Both HPPD and ACCase Inhibiting Herbicides The mutant line ML0831266-03093 that is tolerant to mesotrione and likely other herbicides including HPPD inhibitors, was crossed with mutant line ML0831265-01493 having tolerance to ACCase herbicides and more specifically "fop" type of ACCase herbicides. In one example the ML0831266-03093 plants are the female parent and pollination is by a plant from line ML0831265-01493. In another embodiment the parents are reversed so that ML0831266-03093 serves as the pollinating parent. The resulting F1 seed are harvested having inherited both mesotrione and ACCase herbicide tolerance. The F1 individual carries tolerance to both herbicides at a partially dominant level so they show some tolerance but not to the same level as the tolerant parent lines.

The F1 seeds are planted and the resulting plants are allowed to self-pollinate to produce F2 seed making a population segregating for tolerance to both mesotrione and ACCase herbicides. This population is screened by an herbicide bioassay to identify individuals that have inherited tolerance from the original mutant line ML0831266-03093 and are homozygous for the resistance. A high rate of mesotrione is applied allowing differentiation of heterozygous individuals from homozygous individuals and the tolerance level of the mutation line from the tolerance level in the background of some types of rice including the original line used for mutation to create the ML0831266-03093 line, which was P1003 (FIG. 3A and FIG. 3B).

In one example a rate of 105 gm ai/ha is applied followed three weeks later by a second application of 630 gm ai/ha. In another example a rate of 420 gm ai/ha is applied in a single application. Yet another example entails applying the herbicide at a rate of 630 gm ai/ha. Herbicide applications are done at the three to four leaf stage of seedling growth. The ideal situation is to have also planted near or within the F2 population a set of plants from the original mutant mesotrione donor line ML0831266-03093, a row of plants of the wild-type of the mutation line, P1003, and a row of the line involved as the other parent ML0831265-01493. These control lines will allow easy differentiation for inheritance of the tolerance provided by the ML0831266-03093 mutant line through comparison of the response in the F2 plants to these control lines. Only plants that live and are relatively healthy will have inherited and be homozygous for the tolerance level provided by the ML0831266-03093 mutant line.

Example 9: A Co-Dominant Marker Assay to Select and Develop ACCase and HPPD Tolerant Rice Lines A simple co-dominant marker assay is available to select for inheritance to ACCase herbicides derived from line ML0831265-01493. The marker is developed as a single nucleotide polymorphic marker and detects the causal mutation at position G2096S (blackgrass number) for ACCase tolerance in line ML0831265-01493. All of the surviving plants following the mesotrione bioassay as employed in Example 8 are sampled for tissue collection, the DNA is extracted by known methods and the samples are tested with the SNP assay. A subset of the surviving plants are then also identified as carrying homozygous tolerance to ACCase herbicides through marker assisted selection.

Individuals with tolerance to both mesotrione and ACCase herbicides are selfed to produce F3 families and further selected for other important agronomic characters. The F3 lines are selfed and purified to derive a new line or variety with dual resistance to mesotrione and ACCase herbicides. Such lines are highly valuable as the use of both herbicides provides more complete and broad-spectrum weed control.

In another embodiment the individuals with tolerance to both mesotrione and ACCase are used as trait donors in a backcross (BC) breeding program. After selecting one individual or a few individuals they are used either as the pollinating parent or the female parent. Another more elite and desirable line serves as the recurrent parent to which the traits are transferred.

Following the first cross the F1 plants are crossed again to the recurrent parent. The resulting backcross seed from this cross and ongoing crosses to the recurrent parent are tested with either markers or through herbicide bioassays for inheritance of the herbicide tolerance or a combination of markers and bioassays. In the best situation markers for the functional mutations are used. Alternatively an herbicide bioassay for mesotrione is applied to the BC seed or possibly the BC seed is progeny tested to verify inheritance of the tolerance. Furthermore an herbicide bioassay is used to identify individuals that also inherited tolerance to ACCase herbicides. This process is repeated until the recurrent parent genome is recovered along with the two new traits for tolerance to mesotrione and ACCase herbicides. After the last backcross individuals are selfed to recover the dual herbicide tolerances in a homozygous resistant level in at least one plant.

In yet another embodiment the individuals with resistance to both mesotrione and ACCase herbicides are crossed to a third line and subsequently selfed or even crossed with other lines. The resulting new lines and germplasm is tested and evaluated for other agronomic important traits. Finally new varieties or male and female lines are developed with tolerance to both mesotrione or other HPPD herbicides and ACCase herbicides a combination novel to rice.

Example 10: Mutant Rice ML0831266-03093

The mutant line ML0831266-03093 is demonstrated to carry a high tolerance level to mesotrione herbicide beyond the tolerance found naturally in some rice types including the original mutation treated line P1003. The mutant line is planted in rows or alternatively whole plots are planted and rows of the unmutated line (P1003) and other types of rice or whole plots are planted. Mesotrione is applied pre-emergence or alternatively it is applied post-emergence at the three to four leaf stage of the rice plants. Various rates of mesotrione are applied pre-emergence, pre-emergence followed by post-emergent, or post-emergent with a single or sequential application. Post-emergent applications are applied at the 3-4 leaf stage of the rice.

Figure 22:
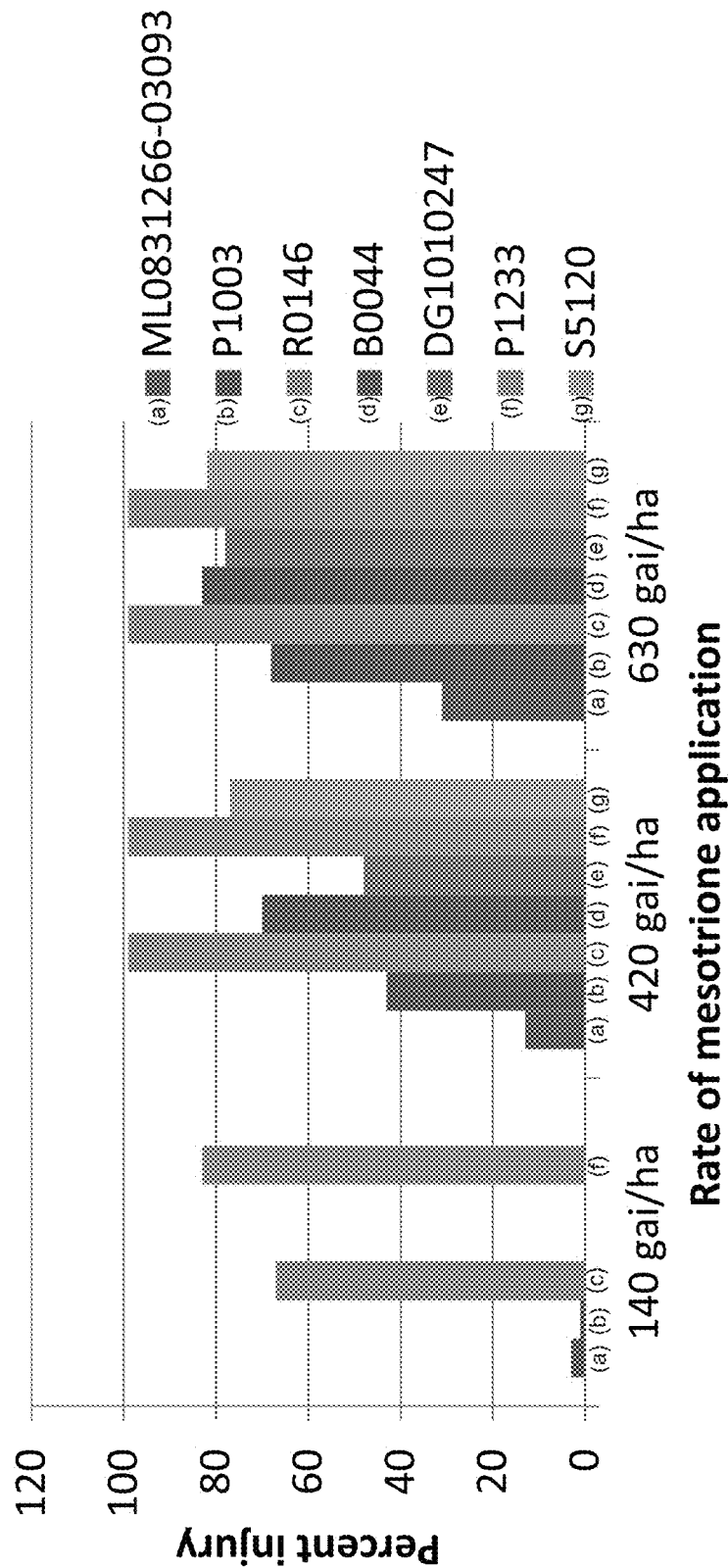
FIG. 22 illustrates a response of different germplasms (genotypes) of rice with different genetic backgrounds to mesotrione applied at the 2-3 leaf stage; wherein different rates of mesotrione are applied.

With low rates (105 gm ai/ha) of mesotrione applied both the mutant line as well as the original unmutated line survive. However, other types of rice, such as the mutant line with ACCase tolerance ML0831265-01493 and the associated unmutated line R0146 are killed at these rates of mesotrione. Applying mesotrione herbicide at higher rates clearly shows new and novel tolerance level as only the mutant line ML0831266-03093 survives while the original unmutated line P1003 and all other tested lines are killed or severally injured. The higher tolerance to mesotrione makes the line ML0831266-03093 of commercial value as both the tolerance can be controlled or bred into new varieties and it is of a high enough level to allow commercial weed control in rice with the application of mesotrione herbicide and possibly other HPPD inhibiting herbicides (FIG. 19A initial results, FIG. 19B new results after 1 year, and FIG. 22—trial results on various rice lines).

Example 11: Chromosomal Locations of Mutations Related to HPPD Inhibiting Resistance The mesotrione tolerant line ML0831266-03093 is tolerant to rates of 420 gm ai/ha and even a dual application of mesotrione first at a rate of 105 gm ai/ha followed three weeks later by an application of 630 gm ai/ha. The line ML0831266-03093 with this high level of tolerance is crossed with a line highly sensitive to mesotrione one being line ML0831265-01493, which has tolerance to ACCase herbicides. The cross is made and the resulting F1 seeds are harvested, planted, and allowed to self to produce a F2 population. The F2 population is grown and tissue is collected from individual plants. Each F2 plant and parental lines are tested with a set of 192 SNP markers identified as being polymorphic between the two mutant lines ML0831266-03093 and ML0831265-01493. The set of polymorphic markers was identified as evenly spaced across the rice genome after testing both parental lines with a set of 796 SNP markers. All 192 markers including two found with linkage to target traits were selected from the 44 k SNP set described by Zhao et al. 2011.

Figure 23:
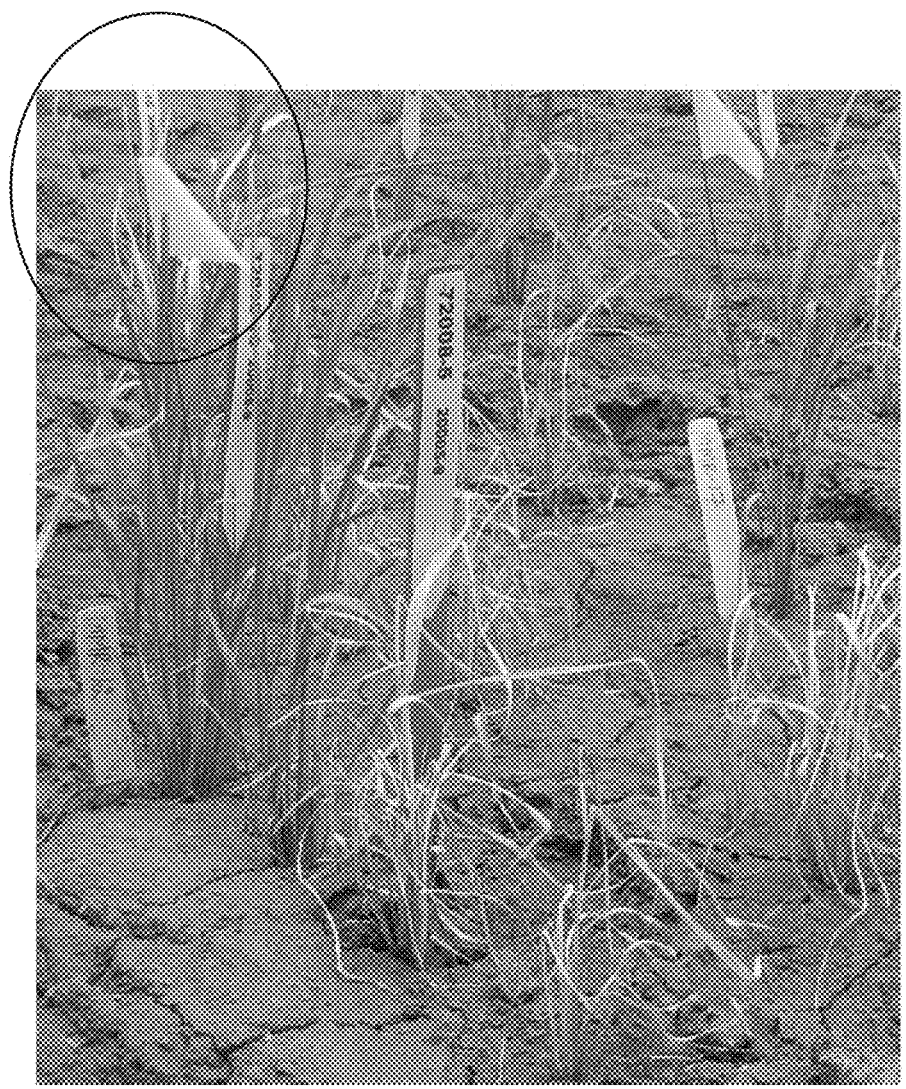
FIG. 23 is a photograph showing phenotypic differences (resistance) of an F2 population derived from the cross of ML0831266-03093 with tolerance to mesotrione and ML0831265-01493 with tolerance to ACCase herbicides; mesotrione was applied with one application of 105 gai/ha followed by a second application of 630 gai/ha; individuals (circled) are selected as inheriting the mesotrione tolerance, whereas the plants that did not inherit the tolerance are dead or severely injured.

Seedlings of size 3 to 4 leaves are sprayed with mesotrione herbicide. In one set of 89 plants mesotrione is first applied at 105 gm ai/ha killing 23 plants. Both the mutant line control ML0831266-03093 and the unmutated line P1003 survived the herbicide application while the unmutated line R0146 was killed. The surviving plants including some additional plants making a total of 95 are then sprayed with another treatment of mesotrione at a rate of 630 gm ai/ha killing or injuring 67 while 28 survived. (FIG. 23) The surviving ratio of plants to those killed or injured fits a one quarter ratio with a chi squared value of 1.03, well within the expected for a single recessive gene. Another set of F2 individuals of size 78 individuals are sprayed with a single application of mesotrione herbicide at a rate of 420 gm ai/ha resulting in 26 plants surviving also fitting in the expected one quarter ratio for a single recessive gene with a chi square value of 2.88 (Table 2).

Example 12: Crosses Between Mutant Lines Resistant to Different Herbicides

The cross between mutant line ML0831266-03093 (ATCC PTA-13620) carrying tolerance to mesotrione and possibly other HPPD inhibiting herbicides with mutant line ML0831265-01493 with (ATCC PTA-12933) tolerance to ACCase herbicides produced F1 seed inheriting both herbicide tolerances. Following selfing of the F1 plants F2, individuals are selected either through herbicide bioassays or alternatively with molecular markers. In the case of ACCase a functional molecular marker is described such that the mutation at position G2096S (based on the black grass numbering system) is selected. Furthermore using either markers linked to the QTLs on chromosome 1 and chromosome 2 or herbicide bioassays recovery of tolerance to mesotrione and ACCase including other HPPD herbicides or other herbicides.

Individuals selected for tolerance to mesotrione including other HPPD herbicides and possibly other herbicides may be used in a backcross conversion program or in breeding to develop new varieties and hybrids with a commercial level of tolerance to mesotrione and other herbicides. Selection with either bioassays or the chromosome 1 and chromosome 2 QTLs leads to the recovery of the inherent tolerance in P1003 along with the mutant tolerance for development of a novel variety or hybrid with herbicide tolerance and representing new weed control options in rice. The tolerance level of the mutant line is superior to other lines and allows for various commercial application methods.

The individual plants with tolerance to both herbicides are used in breeding to develop new varieties and hybrids with tolerance to both ACCase inhibiting herbicides, mesotrione, other HPPD inhibiting herbicides, and other herbicides. The new varieties and hybrids are commercial products. The commercial products are used commercially for rice production. In the production process both ACCase and mesotrione or other herbicides may be applied to the rice crop to control weeds. In one example mesotrione or other herbicides are applied preplant to control germinating weeds and provide residual weed control. Following germination of the rice crop ACCase herbicides are applied for controlling grass weeds. In another example both mesotrione or the equivalent is applied preplant and a second application is made post emergent along with an ACCase herbicide with one or two applications. In another example both mesotrione and an ACCase herbicide or other herbicides including other HPPD herbicides are applied post emergent with one or two applications. In this manner a new and novel strategy is implemented to provide full spectrum weed control in rice. In addition these herbicides have new not previously used in rice modes of action. This strategy therefore has commercial application not only for weed control but as a method to extend the useful life of this strategy and others through the application of multiple modes of action for weed control.

Example 13: Identification of the Causal Mutation for Tolerance to Mesotrione and Other HPPD Herbicides The mutant line ML0831266-03093 is crossed back to the original line, P1003, used for induction of mutations. The F1 seed is grown and the plants selfed to produce an F2 population segregating for tolerance to mesotrione. Each F2 plant is labeled and a leaf sample is collected for DNA extraction. The F2 plants are then sprayed with mesotrione herbicide at the 3-4 leaf stage at a rate of 630 gmai/ha. Among the surviving set of the least injured twenty are identified and used for DNA extraction to represent individuals that inherited the mesotrione tolerance and presumably the causal mutation for tolerance. Out of the plants killed by the herbicide application a set of twenty is also identified for DNA extraction to represent individuals that have the wild-type allele at the causal tolerance locus.

The leaf tissue from the identified individuals is used for DNA extraction and DNA is combined from each set to make a bulk of individuals carrying the tolerance and a bulk lacking the tolerance. In addition DNA is also extracted from leaf tissue derived from the original line, P1003, used for mutation treatment. These samples are used in next generations sequencing at 30× coverage and compared to the rice reference sequence, NIPPONBARE, to the original line used for mutation treatment, P1003, and to each other. Using these comparisons it is possible to identify among the group with tolerance a single mutation being present across all individuals and thus highly likely to be the causal mutation for tolerance to mesotrione.

The genome regions suspected to carry the causal mutation are sequenced by Sanger sequencing technology in both the mutant line ML0831266-03093 and the original non-mutant line P1003. Following the identification of real SNP markers or some other suitable marker is developed and the whole F2 phenotyped segregating population is tested to identify linkage of the suspected causal mutation to the phenotype.

Other characterizations and processes are also applicable to verify the function of the causal mutation. For example the gene containing the mutation is identified through comparison to the published full rice sequence and related databases. Furthermore the gene product or enzyme can be isolated and characterized to describe its normal function and function with the new mutation especially in relation to its function in the presence of mesotrione.

Example 14: Double Mutant Resistant to HPPD and ACCase Herbicides

A simple co-dominant marker assay is available to select for inheritance to ACCase herbicides derived from line ML0831265-01493. The marker is developed as a single nucleotide polymorphic marker and detects the causal mutation at position G2096S (blackgrass number) for ACCase tolerance in line ML0831265-01493. All of the surviving plants following the mesotrione bioassay as employed in example 11 are sampled for tissue collection, the DNA is extracted by known methods and the samples are tested with the SNP assay. A subset of the surviving plants are then also identified as carrying homozygous tolerance to ACCase herbicides through marker assisted selection.

Individuals with tolerance to both mesotrione and ACCase herbicides were selfed to produce F3 families and further selected for other important agronomic characters. The F3 lines were selfed and purified to derive a new line or variety with dual resistance to mesotrione and ACCase herbicides. Such lines are highly valuable as the use of both herbicides provides more complete and broad-spectrum weed control. For example line PL1214418M2-73009 (ATCC deposit PTA-121398) and PL1214418M2-80048 (ATCC deposit PTA-121362) contains tolerance to both HPPD inhibiting herbicide mesotrione and the ACCase inhibiting herbicide fluazifop (see Table 8). Other related lines have also been developed and are highly useful for use as a new weed control system in rice employing both ACCase and HPPD types of herbicide.

In another embodiment the individuals with tolerance to both mesotrione and ACCase are used as trait donors in a backcross breeding program. After selecting one individual or a few individuals they will be used either as the pollinating parent or the female parent. Another more elite and desirable line serves as the recurrent parent to which the traits are transferred. Following the first cross the F1 plants are crossed again to the recurrent parent. The resulting backcross seed from this cross and ongoing crosses to the recurrent parent are tested with either markers or through herbicide bioassays for inheritance of the herbicide tolerance or a combination of markers and bioassays. In the best situation markers for the functional mutations are used. Alternatively an herbicide bioassay for mesotrione is applied to the BC seed or possibly the BC seed is progeny tested to verify inheritance of the tolerance. Furthermore an herbicide bioassay is used to identify individuals that also inherited tolerance to ACCase herbicides. This process is repeated until the recurrent parent genome is recovered along with the two new traits for tolerance to mesotrione and ACCase herbicides. After the last backcross individuals are selfed to recover the dual herbicide tolerances in a homozygous resistant level in at least one plant.

In yet another embodiment the individuals with resistance to both mesotrione and ACCase herbicides are crossed to a third line and subsequently selfed or even crossed with other lines. The resulting new lines and germplasm is tested and evaluated for other agronomic important traits. Finally new varieties or male and female lines are developed with tolerance to both mesotrione or other HPPD herbicides and ACCase herbicides a combination novel to rice.

Example 15: Full Spectrum Weed Control in Rice Based on Dual Resistance to Both ACCase and HPPD Herbicides In the production process both ACCase and mesotrione or other herbicides may be applied to the rice crop to control weeds. In one example mesotrione or other herbicides are applied preplant to control germinating weeds and provide residual weed control. Following germination of the rice crop ACCase herbicides are applied for controlling grass weeds. In another example both mesotrione is applied pre-plant and a second application is made post emergent along with an ACCase herbicide with one or two applications. In another example both mesotrione and an ACCase herbicide or other herbicides including other HPPD herbicides are applied post emergent with one or two application. In this manner a new and novel strategy is implemented to provide full spectrum weed control in rice. In addition these herbicides have not previously been used in rice modes of action. This strategy therefore has commercial application not only for weed control but as a method to extend the useful life of this strategy and others through the application of multiple modes of action for weed control.

SEED DEPOSITS UNDER BUDAPEST TREATY

Seed deposits by Ricetec AKTIENGESELLSCHAFT were made with the American Type Culture Collection (ATCC), 10801 University Boulevard, Manassas, Va. 20110, United States of America. The dates of deposit and the ATCC Accession Numbers are: ML0831266-03093 (PTA-13620, Mar. 19, 2013); ML0831265-01493 (PTA-12933, May 31, 2012); ML0831265-02283 (PTA-13619, Mar. 19, 2013); PL1214418M2-73009 (PTA-121398, Jul. 18, 2014); PL1214418M2-80048 (PTA-121632, Jun. 30, 2014) (see also Table 8). All restrictions will be removed upon granting of a patent, and the deposits are intended to meet all of the requirements of 37 C.F.R. § § 1.801-1.809, and satisfy the Budapest Treaty requirements. The deposit will be maintained in the depository for a period of thirty years, or five years after the last request, or for the enforceable life of the patent, whichever is longer, and will be replaced as necessary during that period.

Definitions

In the description and tables which follow, a number of terms are used. In order to provide a clear and consistent understanding of the specification and claims, including the scope to be given such terms, the following definitions are provided:

Acetyl-Coenzyme. A carboxylase (ACCase; EC 6.4.1.2) enzymes synthesize malonyl-CoA as the start of the de novo fatty acid synthesis pathway in plant chloroplasts. ACCase in grass chloroplasts is a multifunctional, nuclear-genome-encoded, very large, single polypeptide, transported into the plastid via an N-terminal transit peptide. The active form in grass chloroplasts is a homodimeric protein.

ACCase enzymes in grasses are inhibited by three classes of herbicidal active ingredients. The two most prevalent classes are aryloxyphenoxypropanoates ("FOPs") and cyclohexanediones ("DIMs"). In addition to these two classes, a third class phenylpyrazolines ("DENs") has been described.

Certain mutations in the carboxyl transferase region of the ACCase enzyme results in grasses becoming resistant to ACCase herbicides. In the weed Black-Grass at least five mutations have been described which provide resistance to FOP or DIM class of ACCase herbicides. Some mutations rendering ACCase enzymes resistant to these herbicides may be associated with decreased fitness.

Allele. Allele is any one of many alternative forms of a gene, all of which generally relate to one trait or characteristic. In a diploid cell or organism, the two alleles of a given gene occupy corresponding loci on a pair of homologous chromosomes.

Backcrossing. Process of crossing a hybrid progeny to one of the parents, for example, a first generation hybrid F1 with one of the parental genotypes of the F1 hybrid.

Blend. Physically mixing rice seeds of a rice hybrid with seeds of one, two, three, four or more of another rice hybrid, rice variety or rice inbred to produce a crop containing the characteristics of all of the rice seeds and plants in this blend.

Cell. Cell as used herein includes a plant cell, whether isolated, in tissue culture or incorporated in a plant or plant part.

Cultivar. Variety or strain persisting under cultivation.

Embryo. The embryo is the small plant contained within a mature seed.

Essentially all the physiological and morphological characteristics. A plant having essentially all the physiological and morphological characteristics of the hybrid or cultivar, except for the characteristics derived from the converted gene.

Grain Yield. Weight of grain harvested from a given area. Grain yield could also be determined indirectly by multiplying the number of panicles per area, by the number of grains per panicle, and by grain weight.

Injury to Plant. Is defined by comparing a test plant to controls and finding the test plant is not same height; an abnormal color, e.g. yellow not green; a usual leaf shape, curled, fewer tillers.

Locus. A locus is a position on a chromosome occupied by a DNA sequence; it confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Induced. As used herein, the term induced means genetic resistance appeared after treatment with mutagen.

Non-induced. As used herein, the term non-induced means genetic resistance not known to be induced; is at different location in the genome, than induced resistance.

Plant. As used herein, the term "plant" includes reference to an immature or mature whole plant, including a plant from which seed or grain or anthers have been removed. Seed or embryo that will produce the plant is also considered to be the plant.

Plant Part. As used herein, the term "plant part" (or a rice plant, or a part thereof) includes protoplasts, leaves, stems, roots, root tips, anthers, seed, grain, embryo, pollen, ovules, cotyledon, hypocotyl, glumes, panicles, flower, shoot, tissue, cells, meristematic cells and the like.

Quantitative Trait Loci (QTL). Genetic loci that controls to some degree numerically measurable traits that are usually continuously distributed.

Regeneration. Regeneration refers to the development of a plant from tissue culture.

Resistance/Resistant[1]. The inherited ability of a plant to survive and reproduce following exposure to a dose of herbicide normally lethal to the wild type resistance may be naturally occurring or induced by such techniques as genetic engineering or selection of variants produced by tissue culture or mutagenesis.

[1]Weed Science Society of America, Weed Technology, vol. 12, issue 4 (October-December, 1998, p. 789)

Single Gene Converted (Conversion). Single gene converted (conversion) includes plants developed by a plant breeding technique called backcrossing wherein essentially all of the desired morphological and physiological characteristics of an inbred are recovered, while retaining a single gene transferred into the inbred via crossing and backcrossing. The term can also refer to the introduction of a single gene through genetic engineering techniques known in the art.

Tolerance/Tolerant. The inherent ability of a species to survive and reproduce after herbicide treatment implies that there was no selection or generic manipulation to make the plant tolerant.

Resistance/tolerance are used somewhat interchangeably herein; for a specific rice plant genotype information is provided on the herbicide applied, the strength of the herbicide, and the response of the plant.

Sequence listing of HPPD gene and protein LOC_Os02g07160 sequence information

| | |
|---|---|
| Genomic sequence length: | 2760 nucleotides |
| CDS length: | 1341 nucleotides |
| Protein length: | 446 amino acids |
| Putative Function: | glyoxalase family protein, putative, expressed |

```
Genomic Sequence
>LOC_Os02g07160
                                                      (SEQ ID NO: 1)
ACGCCGCCACTGTCATCCACTCCCCCACACCCCACGACGCGCCACGCCACGCCGCGCCGC

GCCGCGCCATGCCTCCCACTCCCACCCCCACCGCCACCACCGGCGCCGTCTCGGCCGCTG

CGGCGGCGGGGGAGAACGCGGGGTTCCGCCTCGTCGGGCACCGCCGCTTCGTCCGCGCCA

ACCCGCGGAGCGACCGGTTCCAGGCGCTCGCGTTCCACCACGTCGAGCTCTGGTGCGCCG

ACGCCGCGTCCGCCGCGGGCCGGTTCGCCTTCGCCCTGGGCGCGCCGCTCGCCGCCAGGT

CCGACCTCTCCACGGGGAACTCCGCGCACGCCTCCCTCCTCCTCCGCTCCGCCTCCGTCG

CGTTCCTCTTCACCGCCCCCTACGGCGGCGACCACGGCGTCGGCGCGGACGCGGCCACCA

CCGCCTCCATCCCTTCCTTCTCCCCAGGCGCCGCGCGGAGGTTCGCCGCGGACCACGGCC

TCGCGGTGCACGCCGTGGCGCTGCGCGTCGCCGACGCGGCCGACGCCTTCCGCGCCAGCG

TCGCGGCCGGTGCGCGCCCGGCGTTCCAGCCCGCCGACCTCGGCGGTGGCTTCGGCCTCG

CGGAGGTGGAGCTCTACGGCGACGTCGTGCTCCGCTTCGTCAGCCACCCGGACGGCGCCG

ACGCGCCCTTCCTCCCGGGTTTCGAGGGCGTCAGCAACCCGGGCGCCGTGGACTACGGCC

TCCGCCGGTTCGACCACGTCGTCGGCAACGTGCCGGAGCTCGCTCCGGTAGCCGCGTACA

TCTCCGGGTTCACCGGGTTCCACGAGTTCGCCGAGTTCACCGCCGAGGACGTGGGCACCG

CCGAGAGCGGCCTCAACTCGGTGGTGCTCGCCAACAACGCGGAGACCGTGCTGCTGCCGC

TCAACGAGCCGGTGCACGGCACCAAGCGGCGGAGCCAGATACAGACGTACCTGGACCACC

ACGGCGGCCCGGGGGTGCAGCACATCGCGCTGGCCAGCGACGACGTGCTCGGGACGCTGA

GGGAGATGCGGGCGCGCTCCGCCATGGGCGGCTTCGAGTTCTTGGCGCCGCCGCCGCCCA

ACTACTACGACGGCGTGCGGCGGCGCGCCGGGGACGTGCTCTCGGAGGAGCAGATCAACG

AGTGCCAGGAGCTCGGGGTGCTCGTGGACAGGGATGACCAGGGGGTGTTGCTCCAGATCT

TCACCAAGCCAGTAGGAGACAGGTAAAATCCTCACCTCTTTCATGATGAAAATGGCTTAT

GAATTCAGATTTGCAGTTATTTGTTGGCACATAGCATCGATTAGGCGCAGAAAGGTGTCA

AGCATTATGAAATTAATCCAGAATGCTIGAATAATACAGTATAATATATGATAGTGAGCT

CTGTGATACTCCATGGATACTCTTTATGTGTCTCCATGAATCCATGATGCGCCTTTCTGA
```

-continued

```
AGATTGTGACACTAGAAAGGGAATAAAGCTGAATGTGCATAGGAAAAAAATGAAAAGCCA

ATGTGTGTCTGTTTATGCCITCTTGCAAGCATATCCCAGTICCTTTTTGCCGGCATGTTG

TAATGCAGATAGCCAGCCACATATAGCTACTTAATTAGTGAGTACTCCCTCTCACAATGT

AAGTCATTCTAGTATTTTCCACATTCATATTGATGCTAATCTATCTAGATTCATTAGCAT

CAATATGAATATGGGAAATACTAGAATGACTTACATTGTGAAACGGAGGAAGTATTACTT

ACTACATCTAAGGTCCATGGATTCCTTTTTTTACAAAAGAAAGAAAGAATCTTATGGCAA

CTCCATCAGCATAAACCAGCAATGCTGCTGGGAACAACTTAAACTTTAGGTTCAGGAGGT

TGTAATTGTCTTTAAGCTTAATAGTCTGATTCAGTCAGTATTCTAATTTCTGCTGCATCT

TTGCTATTGTTATTTCCTCTCTGTGACTCCAAATCTAACTGGATCAGCTATTTCACTCAG

GCCAACCTTTTTCTTGGAGATGATACAAAGGATTGGGTGCATGGAGAAGGATGAGAGTGG

GCAGGAGTACCAGAAGGGCGGCTGCGGCGGGTTTGGGAAGGGCAACTTCTCGGAGCTGTT

CAAGTCCATTGAGGAGTATGAGAAATCCCTTGAAGCCAAGCAAGCCCCTACAGTTCAAGG

ATCCTAGGTAGGAACTGGAGGCCTGGAGCAACAGATGTAACCAGTGTATTTGTATTATGG

AGCAGAAGAAAAAGATGTGCTTTCACTGCTTTGTGATATGTGTCATGCAAGTTGATGTT

GTAATTTGTGGAAGCTGAAGACAAATGATGGTACAATCACTGTAATAGATAATAGACATG

GATCACATACAAGAATGTAACCTAGTGTTGGCATTGCTGCTGTACAATCTTGCTTGGAAA

TAAAATAATAATCAACCTGGAGAAAGAATGTAACCTACTGTTGGCATTGCTGATGTACAA

TCTTGCTTGGAAATAAAATAAGAATCAACCAAGAGAATCTGTCCTTGTGATGCTTGTGAT

CTTCTGGTGTCTTTTTATTTAACAGAATGTAGTGGTCCTCTGCTGCCTCCAACCGTCCAG

GGTAAAAGTGTAAACCGTGGGCTGAGTTACAGCGAATTGCAGTTAGCAATCTGCAAGAGA

CAGGGGATGAACAGAGTAAGGTCAATAGTTCAGTGTATGACATGATCATCTTGTTTCGTG

GCCTTAAATGGCAAGAAAATGGGCTTGTCAGATCTCAAAGAACTCCTATATGTTAAAAGG

CDS
                                                (SEQ ID NO: 2)
>LOC_Os02g07160.1 (SEQ ID NO: 2)
ATGCCTCCCACTCCCACCCCCACCGCCACCACCGGCGCCGTCTCGGCCGCTGCGGCGGCG

GGGGAGAACGCGGGGTTCCGCCTCGTCGGGCACCGCCGCTTCGTCCGCGCCAACCCGCGG

AGCGACCGGTTCCAGGCGCTCGCGTTCCACCACGTCGAGCTCTGGTGCGCCGACGCCGCG

TCCGCCGCGGGCCGGTTCGCCTTCGCCCTGGGCGCGCCGCTCGCCGCCAGGTCCGACCTC

TCCACGGGGAACTCCGCGCACGCCTCCCTCCTCCTCCGCTCCGCCTCCGTCGCGTTCCTC

TTCACCGCCCCTACGGCGGCGACCACGGCGTCGGCGCGGACGCGGCCACCACCGCCTCC

ATCCCTTCCTTCTCCCCAGGCGCCGCGCGGAGGTTCGCCGCGGACCACGGCCTCGCGGTG

CACGCCGTGGCGCTGCGCGTCGCCGACGCGGCCGACGCCTTCCGCGCCAGCGTCGCGGCC

GGTGCGCGCCCGGCGTTCCAGCCCGCCGACCTCGGCGGTGGCTTCGGCCTCGCGGAGGTG

GAGCTCTACGGCGACGTCGTGCTCCGCTTCGTCAGCCACCCGGACGGCGCCGACGCGCCC

TTCCTCCCGGGTTTCGAGGGCGTCAGCAACCCGGGCGCCGTGGACTACGGCCTCCGCCGG

TTCGACCACGTCGTCGGCAACGTGCCGGAGCTCGCTCCGGTAGCCGCGTACATCTCCGGG

TTCACCGGGTTCCACGAGTTCGCCGAGTTCACCGCCGAGGACGTGGGCACCGCCGAGAGC

GGCCTCAACTCGGTGGTGCTCGCCAACAACGCGGAGACCGTGCTGCTGCCGCTCAACGAG

CCGGTGCACGGCACCAAGCGGCGGAGCCAGATACAGACGTACCTGGACCACCACGGCGGC

CCGGGGGTGCAGCACATCGCGCTGGCCAGCGACGACGTGCTCGGGACGCTGAGGGAGATG

CGGGCGCGCTCCGCCATGGGCGGCTTCGAGTTCTTGGCGCCGCCGCCGCCCAACTACTAC
```

-continued

```
GACGGCGTGCGGCGGCGCGCCGGGGACGTGCTCTCGGAGGAGCAGATCAACGAGTGCCAG

GAGCTCGGGGTGCTCGTGGACAGGGATGACCAGGGGGTGTTGCTCCAGATCTTCACCAAG

CCAGTAGGAGACAGGCCAACCTTTTTCTTGGAGATGATACAAAGGATTGGGTGCATGGAG

AAGGATGAGAGTGGGCAGGAGTACCAGAAGGGCGGCTGCGGCGGGTTTGGGAAGGGCAAC

TTCTCGGAGCTGTTCAAGTCCATTGAGGAGTATGAGAAATCCCTTGAAGCCAAGCAAGCC

CCTACAGTTCAAGGATCCTAG

Protein
                                                      (SEQ ID NO: 3)
>LOC_Os02g07160.1
MPPTPTPTATTGAVSAAAAAGENAGFRLVGHRRFVRANPRSDRFQALAFHHVELWCADAA

SAAGRFAFALGAPLAARSDLSTGNSAHASLLLRSASVAFLFTAPYGGDHGVGADAATTAS

IPSFSPGAARRFAADHGLAVHAVALRVADAADAFRASVAAGARPAFQPADLGGGFGLAEV

ELYGDVVLRFVSHPDGADAPFLPGFEGVSNPGAVDYGLRRFDHVVGNVPELAPVAAYISG

FTGFHEFAEFTAEDVGTAESGLNSVVLANNAETVLLPLNEPVHGTKRRSQIQTYLDHHGG

PGVQHIALASDDVLGTLREMRARSAMGGFEFLAPPPPNYYDGVRRRAGDVLSEEQINECQ

ELGVLVDRDDQGVLLQIFTKPVGDRPTFFLEMIQRIGCMEKDESGQEYQKGGCGGFGKGN

FSELFKSIEEYEKSLEAKQAPTVQGS*
```

TABLE 1

Phenotypic characteristics of a mutant rice line showing resistance to mesotrione, with comparison to the original unmutated parent line.

| Designation | Days to 50% Heading | Plant Height | Plant Type | Pubesence | Sheath Color | Awns | TKW, g | yield/plant |
|---|---|---|---|---|---|---|---|---|
| Unmutated parent line | 85 | 96.5 | erect | glaborous | purple inside sheath | None | 23.15 | N/A |
| ML0831266-03093F2 | 82 | 94 | erect | glaborous | purple inside sheath | None | 24.55 | 4.5 |

TABLE 2

Numbers of tolerant plants after three different herbicide bioassays applied to an F2 individuals derived from a cross of ML0831266-03093 with tolerance to mesotrione and ML0831265-01493 with tolerance to ACCase herbicides.

| Parameters | Single application of mesotrione at 105 gai/ha | | Single application of mesotrione at 420 gai/ha | | One application of mesotrione at 105 gai/ha followed by second application of 630 gai/ha | |
|---|---|---|---|---|---|---|
| | Tolerant | Susceptible | Tolerant | Susceptible | Tolerant | Susceptible |
| Observed (o) | 64 | 23 | 26 | 52 | 28 | 67 |
| Expected (e) | 21.75 | 65.25 | 19.5 | 58.5 | 23.75 | 71.25 |
| Deviation (o − e) | 42.25 | −42.25 | 6.5 | −6.5 | 4.25 | −4.25 |
| Deviation (o − e)$^2$ | 1785.06 | 1785.06 | 42.25 | 42.25 | 18.06 | 18.06 |
| (o − e)$^2$/e | 82 | 27.35 | 2.166 | 0.722 | 0.76 | 0.253 |
| Chi-Square Value | 109.35 | | 2.88 | | 1.013 | |
| Degrees of freedom (df) | 1 | | 1 | | 1 | |
| Probability value | | | 0.08919242 | | 0.31393809 | |
| Critical Chi-Square value at p = 0.05 | 3.84 | | 3.84 | | 3.84 | |

TABLE 3

Markers used in QTL analysis

| MARKER | SEQ ID NO: |
|---|---|
| WG-id11001864 | 8 |
| WG-id11002275 | 9 |
| WG-id11003701 | 10 |
| WG-id11007323 | 11 |
| WG-wd10001341 | 12 |
| WG-wd11001701 | 13 |
| WG-wd2002275 | 14 |
| WG-wd7000143 | 15 |
| BG-id10001133 | 16 |
| BG-id10003147 | 17 |
| BG-id10004614 | 18 |
| BG-id1001716 | 19 |
| BG-id1012406 | 20 |
| BG-id1015060 | 21 |
| BG-id1020809 | 22 |
| BG-id1026723 | 23 |
| BG-id11000280 | 24 |
| BG-id11000643 | 25 |
| BG-id11001000 | 26 |
| BG-id11003263 | 27 |
| BG-id11005541 | 28 |
| BG-id11011578 | 29 |
| BG-id12001413 | 30 |
| BG-id12003453 | 31 |
| BG-id12006669 | 32 |
| BG-id12010130 | 33 |
| BG-id2000100 | 34 |
| BG-id2001406 | 35 |
| BG-id2002159 | 36 |
| BG-id2004662 | 37 |
| BG-id2006793 | 38 |
| BG-id2008132 | 39 |
| BG-id2009032 | 40 |
| BG-id2010498 | 41 |
| BG-id2012278 | 42 |
| BG-id2013398 | 43 |
| BG-id3002278 | 44 |
| BG-id3006415 | 45 |
| BG-id3007343 | 46 |
| BG-id3008063 | 47 |
| BG-id3008702 | 48 |
| BG-id3011050 | 49 |
| BG-id3011406 | 50 |
| BG-id3015075 | 51 |
| BG-id4001244 | 52 |
| BG-id4002084 | 53 |
| BG-id4004010 | 54 |
| BG-id4010543 | 55 |
| BG-id4012206 | 56 |
| BG-id5003430 | 57 |
| BG-id5004121 | 58 |
| BG-id5011704 | 59 |
| BG-id5014703 | 60 |
| BG-id6007975 | 61 |
| BG-id6011524 | 62 |
| BG-id6016683 | 63 |
| BG-id6016941 | 64 |
| BG-id7006069 | 65 |
| BG-id8000032 | 66 |
| BG-id8004971 | 67 |
| BG-id8006271 | 68 |
| BG-id9003596 | 69 |
| BG-ud11001609 | 70 |
| BG-ud7000168 | 71 |
| BG-ud7000468 | 72 |
| BG-ud7001467 | 73 |
| BG-ud9000404 | 74 |
| BG-ud9000939 | 75 |
| BG-wd12000096 | 76 |
| BG-wd5002107 | 77 |
| BG-wd7000537 | 78 |
| BG-wd8000300 | 79 |
| WG-id10000057 | 80 |
| WG-id1000027 | 81 |
| WG-id10000678 | 82 |
| WG-id10005716 | 83 |
| WG-id10006397 | 84 |
| WG-id10006890 | 85 |
| WG-id10007362 | 86 |
| WG-id1000987 | 87 |
| WG-id1002788 | 88 |
| WG-id1003490 | 89 |
| WG-id1004858 | 90 |
| WG-id1005915 | 91 |
| WG-id1006413 | 92 |
| WG-id1007758 | 93 |
| WG-id1008433 | 94 |
| WG-id1011077 | 95 |
| WG-id1013249 | 96 |
| WG-id1015747 | 97 |
| WG-id1019114 | 98 |
| WG-id1022207 | 99 |
| WG-id1023338 | 100 |
| WG-id12004473 | 101 |
| WG-id12005677 | 102 |
| WG-id12007189 | 103 |
| WG-id12008113 | 104 |
| WG-id12009381 | 105 |
| WG-id2000711 | 106 |
| WG-id2003035 | 107 |
| WG-id2003988 | 108 |
| WG-id2005453 | 109 |
| WG-id2005879 | 110 |
| WG-id2007502 | 111 |
| WG-id2011561 | 112 |
| WG-id2011986 | 113 |
| WG-id2014452 | 114 |
| WG-id2015344 | 115 |
| WG-id2016104 | 116 |
| WG-id3000020 | 117 |
| WG-id3003557 | 118 |
| WG-id3003855 | 119 |
| WG-id3004338 | 120 |
| WG-id3005216 | 121 |
| WG-id3005783 | 122 |
| WG-id3009997 | 123 |
| WG-id3010769 | 124 |
| WG-id3013945 | 125 |
| WG-id3016222 | 126 |
| WG-id3017628 | 127 |
| WG-id3018382 | 128 |
| WG-id4000023 | 129 |
| WG-id4001471 | 130 |
| WG-id4002895 | 131 |
| WG-id4004798 | 132 |
| WG-id4005527 | 133 |
| WG-id4005882 | 134 |
| WG-id4006725 | 135 |
| WG-id4007645 | 136 |
| WG-id4008100 | 137 |
| WG-id4008430 | 138 |
| WG-id4008947 | 139 |
| WG-id4009312 | 140 |
| WG-id4009705 | 141 |
| WG-id4011039 | 142 |
| WG-id4011619 | 143 |
| WG-id4011820 | 144 |
| WG-id5001055 | 145 |
| WG-id5002055 | 146 |
| WG-id5002453 | 147 |
| WG-id5002782 | 148 |
| WG-id5004697 | 149 |
| WG-id5006824 | 150 |
| WG-id5007247 | 151 |
| WG-id5007583 | 152 |
| WG-id5008807 | 153 |
| WG-id5009334 | 154 |
| WG-id5010535 | 155 |
| WG-id6000075 | 156 |
| WG-id6001960 | 157 |
| WG-id6002888 | 158 |
| WG-id6003335 | 159 |

TABLE 3-continued

Markers used in QTL analysis

| MARKER | SEQ ID NO: |
| --- | --- |
| WG-id6004012 | 160 |
| WG-id6004657 | 161 |
| WG-id6005348 | 162 |
| WG-id6007016 | 163 |
| WG-id6010853 | 164 |
| WG-id6012703 | 165 |
| WG-id6014165 | 166 |
| WG-id6016119 | 167 |
| WG-id7000480 | 168 |
| WG-id7001929 | 169 |
| WG-id7002851 | 170 |
| WG-id7003936 | 171 |
| WG-id7004491 | 172 |
| WG-id8000555 | 173 |
| WG-id8001575 | 174 |
| WG-id8002235 | 175 |
| WG-id8005634 | 176 |
| WG-id8006703 | 177 |
| WG-id8007014 | 178 |
| WG-id8007344 | 179 |
| WG-id8007751 | 180 |

TABLE 3-continued

Markers used in QTL analysis

| MARKER | SEQ ID NO: |
| --- | --- |
| WG-id9000056 | 181 |
| WG-id9002563 | 182 |
| WG-id9002755 | 183 |
| WG-id9005502 | 184 |
| WG-id9006187 | 185 |
| WG-id9006850 | 186 |
| WG-id9007344 | 187 |
| WG-ud1001267 | 188 |
| WG-ud7000348 | 189 |
| WG-ud7001018 | 190 |
| WG-ud7002024 | 191 |
| WG-id1028225 | 192 |
| WG-id11000006 | 193 |
| WG-id11007850 | 194 |
| WG-id11008114 | 195 |
| WG-id11009132 | 196 |
| WG-id12002544 | 197 |
| WG-id11006215 | 198 |
| WG-id11002912 | 199 |

TABLE 4

SNP markers

| ID | Chromo-some | upstream sequence | Allele | downstream sequence | SEQ ID NO: |
| --- | --- | --- | --- | --- | --- |
| WG-id1002788 | 1 | ATGCCCACGGCGGCGGCGGAGGA GGAGGAGGAGGAGGAGCTAAGGAGCG GCGCGGTACGTCGCCGGTGCTGTTCTGC TTTGTAGCCGCTGCTGTCCT | C/T | GTCGGAAATGCCTGCCACGGGCTGTTCC CGCAGGTATTGAGAAATGAGCGCTGAG TTCCTGACGCGTTTAAATCCACTGATTA GCTGAGTTCCCTTCCAA | 4 |
| WG-id1003490 | 1 | GAGAGTGGAGGAGGAGGACGAGTGGA GGTGGAGGTGGCGCGCGGCTGCGCGG TGCGCTTCTTTTTTTTTTCTTTTTTTGTTC CCGCCGCAACCAAAGGAG | A/G | CAAGCAAAGGAAGCAAGCAAAAGAAA AAAAGCCCGGGAATTTACCTGGCGGGA ATGCCCTACTTGGCAGCGCCGCCCGTCT CTCTCCACAAACGCCCTGC | 5 |
| BG-id2004662 | 2 | TTCTATCTCAAGGCGGCAATAGAATCAT AGATGCTAGAGTCCAGAAGAAGGCCAA AGACTTGAAATTTTCAGTTGAGAATGAG CAATCCAAGGTGATGCT | C/T | GCCAAATGTCTGATGAATTGCTCTTGCT CTGATGTTGAGCCCGATGAAGTTGTTAG CTGCTGAGGACATGATCGGTACCACCTA TATTGACAACCCTGAT | 6 |
| WG-id2003988 | 2 | TCAGTGTTCACGGACCCTACATGGAGTT CTCCTAAGTTCAACTACAAGAGACATAG CCCATAGGGTAATGCCCTCACTTTCCAG CTCTTTAACTATGGAG | A/G | TATCAATCGATCAATCACCAATCGGATG GTACCAAATCCAAAACAACAGTTGGGG AAAACTGATCCTACCAACCCAGCTCAAC TAATTTTGCAGTGCTAC | 7 |

TABLE 5

Unknown ACCase mutation -QTL start and end SNP marker sequences

| ID | Chromo-some | Upstream sequence | Allele | Downstream sequence | SEQ ID NO: |
| --- | --- | --- | --- | --- | --- |
| id1019752 | 1 | Ataaagatgaggtgtttgatgaattaaaggccgca gggttgaagaggccatgtagctttacagatatttc cagtgaaaatgctttgcttcttgaatttga | g/t | acagcaactgatgcagctgctgcgaaagcccatat taggcgccagcttcatccagatgtctgttcccagg acaagaatacttctggtcatgaacttttttg | 206 |
| id1025754 | 1 | tcacatgatctgcaactgtcaacagtcttaccgga attggattctgaaggtggatactccacctgtccac cataagtccttatttgtcagaggttacaat | t/c | gcatgatgtgtctatactctatactgcaaagatga atactaacaagttttcttgggcttaaaagaagaa aaactaggaacagcctcactagtttgctac | 207 |

TABLE 6

List of mutations identified in Quizalofop mutant. These mutations were identified using MutMap method (whole genome sequencing)

| ID | Chromo-some | Upstream sequence | Allele | Downstream sequence | SEQ ID NO: |
|---|---|---|---|---|---|
| Chr1Q MM327 85958 | 1 | tgtttcaagtttggttgctgaaaaacgtacggacaaa ccatgaactaacttgctattttgctccacatgggttt gtctcgaagcaaccaggaattgatca | g/a | cttcggtggttttgccaagaacatgaaacctggggataa ggatttttttcgactttgctaatgctggtcgtctggat taggaacagaacaggtattgctac | 208 |
| Chr1Q MM331 47227 | 1 | agtctaaatgggctgcactttgattgggctgggttca tatgagattagggggaaaaaaacacgaacattccagtaa aatggggagtgtgaactgtgaagaag | a/g | gggtaaacggtgtgcggacgtgagacgagaaaagcatg agagaaaacgatctgtgtgcatgcataggggctggacga aaagctcgtgactcgttagctcgc | 209 |
| Chr1Q MM332 01871 | 1 | tagggcttctgatagccctccatctgtccgtcctttg cccgttttgcttcttggcctaaaccaccgaaaaggtgg gtccgttttgctggacgcctggaata | t/c | tcttcaactcgattggaacagcaggctccgtgtatgtg taactatggctgtgtttagatctaaagtttagattcaa agtatagatttaaacttcagtcat | 210 |
| Chr1Q MM343 74172 | 1 | tgctgattctcaggctgattctacttggttggtagaa aatctactatccaggaacaagcgtagggtaacttttt cctttttttctcagctatgtgaaaag | a/g | gagaaaactcgctcacttttataggaaatgaactactc ttctaccgacggatatcctaaaggctatcctctggtac ctcggccttacgctaactcaaaac | 211 |
| Chr1Q MM344 82064 | 1 | cgatcccagggaggttgtggaagtgcttctcatgacc ttcgaggcactgcggcgtaggcatcttcaattggatg agacacaagagactagcaaacgtgca | a/g | acctgaaggctggtgccatcatgttggccagtaatctg agggctaacattgggaagaggattggagctgtccctgg agttgaagtaggggatattttcta | 212 |
| Chr1Q MM346 80949 | 1 | aattccaatttcatcccatttgtcccattccctcctg attactttgccaagaaaaataagcctgtggagaattc atcagatgcaggaatagtgccagaag | a/g | ccctccatcagctgaaaaattaccagaaacaaaatatt catctggaaatctgggaaatttttcagaacagctcacag gtgatgggcagtcaggcagcaaac | 213 |
| Chr1Q MM349 76760 | 1 | gttttggttgctattaatcgattgagcaagtagggga aatattcctatcatctatgcttcaaataaagtttttct cttaaattactcatccgatttacaat | t/c | cgattacaccgttgtgttcgtaataattaaatctttac aacaagatctcacatgattatattttgatgaaaaatca caaattacttttatgatatgtcta | 214 |
| Chr1Q MM354 98447 | 1 | gtcccgcctggtgacgatttccatgggcattgcgccg actgactgtgtcggcagcatgcatcgtctcgggcgtt caacgtgtggaggggacgacgtataa | a/g | agtacacgcgaagactgtaggtagaggtgcttttcccg cgaaaagtggcagtagcggcggttggacagtaaccttc gtgtatggttgtgtgttcatctca | 215 |
| Chr1Q MM357 79866 | 1 | tgcttgtgcgttcactgttcagagaagctggttatcc tccctgataagaacagccgggaggtcagtgtgctatg gttttgtttagttctggaatgatcca | a/g | tcacccagcacaattgactggctgagtgttgcattaag caaatctggaccggatttgagggaattttctcgcgcag tggagatctatgataaatctcgta | 216 |
| Chr1Q MM361 60202 | 1 | ctgcttcgccaacggcctcgaggcgaggctggcaggt actggtagtcaaatttacaagaactacacgataactc ggcttccatgcactgatgtgctgaaa | a/g | cgtaccagctttatttggcagcttgcccatttaagaag atctctcattactttgccaatcaaacaattttgaatgc tgtggagaaggccaagaaagttca | 217 |
| Chr1Q MM363 86713 | 1 | tcacattctggttgttgagggtccactgatacctta cctgttgcagtttattgttttaaataatccaatcaaa cttttgtttgagcttattgctgaata | a/g | cacagcagcagtacatgcaatgcaagatgcccagatga tgagaataaaggcaatggcaaaaatataagtgctagtt ctatttcaaaataacaaacagaca | 218 |
| Chr1Q MM364 47011 | 1 | tatgatgatgcttattatagcctaaggtatgtacttt taagatttagttcgaagtaatgcccatctggcaagtt aattccagcattaacgtgttctaaaa | a/g | ccactctacttatgagaagccgggccaccacattcata cattacagccagaaacaacaaatccaggaagttaatac gtgattaagaatgcatcaaacaag | 219 |
| Chr1Q MM367 47244 | 1 | tcgatatgttgggttttttctctttactagtagcatg ccatcagtgtgcatcttacgtagtggaatattatcg ggcacccaatattcggctcgcacaaa | a/g | ctccgaggacgaggaggaggacgactaatttggcagct cagctcacctgcacggctgcactgtgctgtgcccggtg ggcgaagccatttcacccgcgggc | 220 |
| Chr1Q MM282 57622 | 1 | tctgaaaacgcatggccgaaataagatgcaagaacac ctgcaaaataatctcaggatcagtccaggtacgcatt ctctactgttatctactgaaccagag | a/g | ggaaaaaaacaaaaactaggatgaatgcagtgtcactt tgctgcttgtaattctctgaatttctgaatgaaagaaa agaaaagaaaagaagcgaaactgg | 221 |
| Chr1Q MM292 78751 | 1 | cttaaattctcatgttttattcccgttgcaacgaacg gtcatttcttttagtgtccataaatagctataagagg catcgatcatcgcagcaagccgactg | a/g | gtgtggcgcctacgtgatcgttggtttgtttcgcttgt ttgggcatacagctatgagaacttgttgggggcccat actacttatcatcatgtgtctaat | 222 |
| Chr1Q MM293 40100 | 1 | gaactaaacacacccggaatgtgatggatccgaatct gctgtagttgatactgtgaatgtaacttgtaggcctc atttgattttctagaaaaaaatggag | a/g | aaaaacataggaataagaatcctatgtgaattggtact gttcatccctttgatttgtaggaattgaacaaaggaaa agcatgggaaaaaaatcctatga | 223 |
| Chr1Q MM298 75869 | 1 | agcgccacgccggccagcgccgtggtgttctccgg gtggcatcgcgcttgagctacatcaccaccgatggccac ttaaagtccgttgagctcgatccgca | a/g | atccggcggctccacagggccgtcggcaacgcggtcgt cgacgacaagtacttggtcttcgggaccggctccaccc acctgatcaacgcgctggtgtacg | 224 |
| Chr1Q MM301 73016 | 1 | acgggcggtaccagctacctgtcacagacatgtgggc ccagcttaacgctaacgcgctgatggcccccacatggc agcgacctgccccctctgtccctccg | c/t | tccacgggcgcaccgagcgtccaccgcccccccgcgata tccggggggtttaggcgatatttagccacgagaggggga ggggagagtaggagaccgacgctt | 225 |

TABLE 6-continued

List of mutations identified in Quizalofop mutant. These mutations were identified using MutMap method (whole genome sequencing)

| ID | Chromo-some | Upstream sequence | Allele | Downstream sequence | SEQ ID NO: |
|---|---|---|---|---|---|
| Chr1Q MM301 98493 | 1 | agaaagacttgctttagctttattgtttcttttccat attctatattcttgaaaaggactgcaaagctcttcta gtatatgcaattagctgctttggaag | a/g | cacttcaaaagggatgaaggaaagaaggctgtcatatc aattactcaatcatgaccagatcatcgatctgatgcag ttaaaaatttcattaattttgcca | 226 |

TABLE 7

List of mutations identified in Mesotrione mutant. Mutations were identified through MutMap method (whole genome sequencing).

| ID | Chromo-some | Upstream sequence | Allele | Downstream sequence | SEQ ID NO: |
|---|---|---|---|---|---|
| Chr1C MM334 9975 | 1 | atcgatgtaattagtgatgtcaatcaatggtccaga tggcatttggagtcttcgagccttatctttagtgtc acttgcatttttcagttccaaatgaacatctggaaga aggcttggatatctttggaatttcattgataggatg aaaatctcttgccgcatgaagcctgacggagtttcc gttagccaaagtggcatcag | a/g | Tacagcatattccaaggaatctgtgtgcttcctat caggttttgctggaatggaaaattgtgctggctca gttttgctgttcccctacttttcaataaatcagg ttcaccttcttttcgcagaccagttgaatttgta tattctctttacaagcagatgctgaagagtggcct aataaattatttggtgaaacctcta | 227 |
| Chr1C MM356 8176 | 1 | Taacctatagtgggacaaggactgaaaagcagttc ctcttgctttaacccagagagggtcaacattttttct ccctgtaagttccaatgctccacaatattttgtatca agtgttttgaggttccaggatatgcttcagaatcca ttgctccccatctcaatagaatgcataagctgaaaa ggcaagaaaagtggaataa | a/g | aaatagattttctacaagcacatgatcattggtgg gcactgcccacagataaaactagctagctctcggc agtcttacccatgggaaacagtaggatctatcgaa aaatcaagcagctgctttgatataaactttccaggc agtatagaaatctggcaaagagattagcagctcac ctcagaagtgaaatttggagggcaa | 228 |
| Chr1C MM405 2710 | 1 | ccaagcggagacatcgcttccatgagcaattcacgg ttttttcactagatctctcacc ctttctctgatccattctggaccagcctctaatgcg tagagcgccaggcgctgcccgatgatggaagcacag ataggtatgttatcttgcacttttgagcagctgtgca tgaagaccgtcagctctcgtttgggtgggcaat | a/c | tgcagcagtcagctcatcagttcttgtaagactca ctgatcaacacagattgtgcagccactaagttact tatactgcattgctatggtgataatttaagggaat gccctggtaaaagattcaagtggatgcgggaaatt catgaaactgaaagaactcaatattgactcttaca tcagcattttcaagcctaagcagag | 229 |
| Chr1C MM420 3161 | 1 | tttaaatcaaatcttaaaaatataaatcataaataa ctatcaagttgttgagtttaaaaatataaaaattat ataaatatatttgtcttgaaaaatactttcataaaa gtatacatatatcacttttttaataaatattttata aaaacaagaagtcaaagttatgtttttagagaccgcg tctctgttctaaacgacttc | t/c | tttataagtatggagggagtatccatttcacatat acttatgtgcttgtttacatcccaacaaatttttag ccaaaaacatcacatcaaatatttagccacatgta taggacattaaatataaaaaaacaattcacacagtt tgcatgtaaattgcgagacgaatcttttgagccta attacgccattatttgacaatgtgg | 230 |
| Chr1C MM438 8604 | 1 | cggaactatgactaactcctctccgtaagcttcttt gtaatatgtattgctgctgtacttggtctcattatc tccttacagatatatacattttttgcagggtata tccacttcatcttctccgtgacattgagactagggt ttggctcctggccgtggagtcagagagtcagtgtaa agctgacggagaatatgcac | t/c | ttccagtgttactcaaaatctagctactggaaaca ataccaatattatagaacaaacagctgatgttatc acaaaaatagacaatagtatgagttcaccacggat gagaataacagaaaggaatggtataagggacaaca ccacccccatcattccatcaacatttgcaactcttt gagtctaatggcgaaggcgtacata | 231 |
| Chr1C MM442 5961 | 1 | caactactgacaacaagtgccatgtctaaatttctg aacatgcacacaacacacaaatgatgaatatggtga aaccgcaattagcattagaaagttttaactctagaa atcaatttccaagttgtaatccccatactcccaacc cagaagggaaaaaaaacaactccaaaaccc | t/c | caacttttaaaaatgtgggaacaatcaaaccatat gcttgagatatacccacaaagccatcggcggccgc ttacagcagagtacaccctcatcttgcacgcctcc gaagaagcaggagccgtgatcaacacgagcatctt gtcctgctccacccccacacagtgacgagtctaggg cacgacgaaggcgcgctcctaaacc | 232 |
| Chr1C MM445 4432 | 1 | cttcctgtcgtgagtgactgggtggtgggctcaatc ggcctggcccgatacgatgcaagcgcgtggctgggc aggagatcggacggtgctgattgttgggcgacgtg gccgcgtgggcgaatgaatagtgaacagtaccacg tgaggtttataggattttatatgactagggtgaac gttggatagaagggaatgtg | t/c | tagtgctgttctgaacctcttgcgcatacattaac atgtttatctaatctaataaacatgattaaatttt agcgtttgcttttacagtagtagaaatatgaaatt gaacaatggttagtctgaggaatcataagcctatg atctagctggagtcttctccggtttaagctaccaa ttgaaacatattaattgatgcctga | 233 |
| Chr1C MM449 6531 | 1 | aatgtgctcaacttcatatatatgtgtgttgagcac atagctcatatataagatcaatggttagatcaatgg tttttgggttagatcagttgagcacatagcta tatatatgtgtgctcaacggctcacacacaacttca tatatatgtacccaaaaaagcactattagatcaatg gttataattgtttcaccacg | a/g | aatattcaactttactcaatgttttgtttaacaag ttccttttggtcacttgccaattttttctagatcat acagtacaatctattgatcacaattcacattgaat aactaggtcaagccattctgtacatgcccatgcat gaacttactgctactaatattatcttagattaattt atcctgaaacttatagtcatatgtg | 234 |

TABLE 7-continued

List of mutations identified in Mesotrione mutant. Mutations were identified through MutMap method (whole genome sequencing).

| ID | Chromosome | Upstream sequence | Allele | Downstream sequence | SEQ ID NO: |
|---|---|---|---|---|---|
| Chr1C MM371 4792_ CA-C | 1 | gcatgaaagctgagaccatcaccaggttgatcgttg ttgctgctattataagatgccaaaatcggcaaatcg gtcattcactcaaggattggacacaaga | c/ca | aaaaaaaagtaacaggtagcagactttcaactaac ctggcatgaaagcttggattgtcactggtttgatt gttgctgctgctgttatgaaagctgtata | 235 |
| Chr1C MM393 1650_ A-T | 1 | acgttgcttaggtagcaccttgatttaatcaaatgc tagctagttgatgccaggtggcacactgcggacgga tttgtttgtcagtttccctgcattacac | t/a | ttgtacaggagtgtactacatccacatacaatgaa cagtagtagtagcagcagctatatactccagttgc ctagtcgtacacaaagtataattaatcaca | 236 |

TABLE 8

| LINE | SOURCE DESIGNATION | TRAIT RESISTANCE/ TOLERANCE TO INHIBITORS | ATCC DEPOSIT |
|---|---|---|---|
| P1003 | | HPPD (NON-INDUCED) | |
| R0146 | | HPPD SENSITIVE | |
| ML0831266-03093 | | HPPD (INDUCED + NON-INDUCED) | PTA-13620 Mar. 19, 2013 |
| ML0831265-01493 | 09PM72399 | ACCASE G2096S MUTATION | PTA-12933 May 31, 2012 |
| ML0831265-02283 | | ACCASE (UNKNOWN MUTATION) | PTA-13619 Mar. 19, 2013 |
| PL1214418M2-73009 | | ACCASE G2096S MUTATION HPPD (INDUCED + NON-INDUCED) | PTA-121398 Jul. 18, 2014 |
| PL1214418M2-80048 | | ACCASE G2096S MUTATION HPPD (INDUCED + NON-INDUCED) | PTA-121362 Jun. 30, 2014 |
| PL1214418M2-73001 | | ACCASE-G2096S HPPD (INDUCED) | |
| PL1214418M2-73013 | | ACCASE-G2096S HPPD (NON-INDUCED) | |

TABLE 9

Agronomic characteristics of two lines carrying both HPPD and ACCase resistance/tolerance.

| Designation | Days to 50% Heading | Plant Height | Plant Type | Pubesence | Sheath Color | Awns | yield/plant |
|---|---|---|---|---|---|---|---|
| PL1214418M2-80048 | range 56-94 | range 57-80 cm | erect to intermediate | variation of glaborous and smooth | variation between green and purple | None | 13.39 gm |
| PL1214418M2-73009 | 85 | range 84-108 cm | erect to intermediate | variation of glaborous and smooth | variation between green and purple | None | NA |

PUBLICATIONS

All publications cited in this application are herein incorporated by reference

Akira, Abe et al., *Genome sequencing reveals agronomically important loci in rice using MutMap Nature Biotechnology* 30, 174-178 (2012), Published online 22 Jan. 2012.

Wright, Mark H. et al., *Genome-wide association mapping reveals a rich genetic architecture of complex traits in Oryza sativa. Nat. Comm* 2:467|DOI: 10.1038/ncomms1467, Published Online 13 Sep. 2011. The marker information can be accessed from The Rice Diversity Home Page and downloading the file "44K GWAS Data" (http://www.ricediversity.org/index.cfm).

Zhao, Keyan et al. (2011). *Genome-wide association mapping reveals a rich genetic architecture of complex traits in Oryza sativa. Nat Comm* 2:467|DOI: 10.1038/ncomms1467, Published Online 13 Sep. 2011

The invention claimed is:

1. A seed of a rice plant tolerant/resistant to ACCase inhibitors wherein representative seed of said rice plant has been deposited under ATCC accession number PTA-13619.

2. A rice plant tolerant/resistant to ACCase inhibitors grown from the seed of claim 1.

3. The rice plant of claim 2 wherein the tolerance/resistance is correlated with the presence of at least one nucleic acid sequence selected from the group consisting of SEQ ID NOs: 208-226 in the plant genome.

4. The rice plant of claim 3, wherein the nucleic acid sequence is further selected from the group consisting of SEQ ID NO: 202 combined with at least one of SEQ ID NOS: 208-226.

* * * * *

SEQUENCE LISTING

<160> NUMBER OF SEQ ID NOS: 236

<210> SEQ ID NO 1
<211> LENGTH: 2760
<212> TYPE: DNA
<213> ORGANISM: Oryza sativa

<400> SEQUENCE: 1

| | | | | | |
|---|---|---|---|---|---|
| acgccgccac | tgtcatccac | tcccccacac | cccacgacgc | gccacgccac | gccgcgccgc | 60 |
| gccgcgccat | gcctcccact | cccaccccca | ccgccaccac | cggcgccgtc | tcggccgctg | 120 |
| cggcggcggg | ggagaacgcg | gggttccgcc | tcgtcgggca | ccgccgcttc | gtccgcgcca | 180 |
| acccgcggag | cgaccggttc | caggcgctcg | cgttccacca | cgtcgagctc | tggtgcgccg | 240 |
| acgccgcgtc | cgccgcgggc | cggttcgcct | tcgccctggg | cgccgcgctc | gccgccaggt | 300 |
| ccgacctctc | cacggggaac | tccgcgcacg | cctccctcct | cctccgctcc | gcctccgtcg | 360 |
| cgttcctctt | caccgccccc | tacggcgcg | accacgcgt | cggcgcggac | gcggccacca | 420 |
| ccgcctccat | cccttccttc | tccccaggcg | ccgcgcggag | gttcgccgcg | gaccacggcc | 480 |
| tcgcggtgca | cgccgtggcg | ctgcgcgtcg | ccgacgcggc | cgacgccttc | cgcgccagcg | 540 |
| tcgcggccgg | tgcgcgcccg | gcgttccagc | ccgccgacct | cggcggtggc | ttcggcctcg | 600 |
| cggaggtgga | gctctacggc | gacgtcgtgc | tccgcttcgt | cagccacccg | gacggcgccg | 660 |
| acgcgccctt | cctccggggt | ttcgagggcg | tcagcaaccc | gggcgccgtg | gactacggcc | 720 |
| tccgccggtt | cgaccacgtc | gtcggcaacg | tgccggagct | cgctccggta | gccgcgtaca | 780 |
| tctccgggtt | caccgggttc | cacgagttcg | ccgagttcac | cgccgaggac | gtgggcaccg | 840 |
| ccgagagcgg | cctcaactcg | gtggtgctcg | ccaacaacgc | ggagaccgtg | ctgctgccgc | 900 |
| tcaacgagcc | ggtgcacggc | accaagcggc | ggagccagat | acagacgtac | ctggaccacc | 960 |
| acggcggccc | ggggtgcag | cacatcgcgc | tggccagcga | cgacgtgctc | gggacgctga | 1020 |
| gggagatgcg | ggcgcgctcc | gccatgggcg | gcttcgagtt | cttggcgccg | ccgccgccca | 1080 |
| actactacga | cggcgtgcgg | cggcgcgccg | gggacgtgct | ctcggaggag | cagatcaacg | 1140 |
| agtgccagga | gctcggggtg | ctcgtggaca | gggatgacca | gggggtgttg | ctccagatct | 1200 |
| tcaccaagcc | agtaggagac | aggtaaaatc | ctcacctctt | tcatgatgaa | aatggcttat | 1260 |
| gaattcagat | ttgcagttat | tgttggcac | atagcatcga | ttaggcgcag | aaaggtgtca | 1320 |
| agcattatga | aattaatcca | gaatgcttga | ataatacagt | ataatatatg | atagtgagct | 1380 |
| ctgtgatact | ccatggatac | tctttatgtg | tctccatgaa | tccatgatgc | gcctttctga | 1440 |
| agattgtgac | actagaaagg | gaataaagct | gaatgtgcat | aggaaaaaaa | tgaaaagcca | 1500 |
| atgtgtgtct | gtttatgcct | tcttgcaagc | atatcccagt | tcctttttgc | cggcatgttg | 1560 |
| taatgcagat | agccagccac | atatagctac | ttaattagtg | agtactccct | ctcacaatgt | 1620 |
| aagtcattct | agtattttcc | acattcatat | tgatgctaat | ctatctagat | tcattagcat | 1680 |
| caatatgaat | atgggaaata | ctagaatgac | ttacattgtg | aaacggagga | agtattactt | 1740 |
| actacatcta | aggtccatgg | attccttttt | ttacaaaaga | aagaaagaat | cttatggcaa | 1800 |
| ctccatcagc | ataaccagc | aatgctgctg | ggaacaactt | aaactttagg | ttcaggaggt | 1860 |
| tgtaattgtc | tttaagctta | atagtctgat | tcagtcagta | ttctaatttc | tgctgcatct | 1920 |
| ttgctattgt | tatttcctct | ctgtgactcc | aaatctaact | ggatcagcta | tttcactcag | 1980 |
| gccaaccttt | ttcttggaga | tgatacaaag | gattgggtgc | atggagaagg | atgagagtgg | 2040 |
| gcaggagtac | cagaagggcg | gctgcggcgg | gtttgggaag | ggcaacttct | cggagctgtt | 2100 |

-continued

```
caagtccatt gaggagtatg agaaatccct tgaagccaag caagccccta cagttcaagg      2160
atcctaggta ggaactggag gcctggagca acagatgtaa ccagtgtatt tgtattatgg      2220
agcagaagaa aaaagatgtg cttcactgc  tttgtgatat gtgtcatgca agttgatgtt      2280
gtaatttgtg aagctgaag  acaaatgatg gtacaatcac tgtaatagat aatagacatg      2340
gatcacatac aagaatgtaa cctagtgttg gcattgctgc tgtacaatct tgcttggaaa      2400
taaaataata atcaacctgg agaaagaatg taacctactg ttggcattgc tgatgtacaa      2460
tcttgcttgg aaataaaata agaatcaacc aagagaatct gtccttgtga tgcttgtgat      2520
cttctggtgt cttttattt  aacagaatgt agtggtcctc tgctgcctcc aaccgtccag      2580
ggtaaaagtg taaaccgtgg gctgagttac agcgaattgc agttagcaat ctgcaagaga      2640
caggggatga acagagtaag gtcaatagtt cagtgtatga catgatcatc ttgtttcgtg      2700
gccttaaatg gcaagaaaat gggcttgtca gatctcaaag aactcctata tgttaaaagg      2760
```

```
<210> SEQ ID NO 2
<211> LENGTH: 1341
<212> TYPE: DNA
<213> ORGANISM: Oryza sativa

<400> SEQUENCE: 2
```

```
atgcctccca ctcccacccc caccgccacc accggcgccg tctcggccgc tgcggcggcg       60
ggggagaacg cggggttccg cctcgtcggg caccgccgct tcgtccgcgc caacccgcgg      120
agcgaccggt tccaggcgct cgcgttccac cacgtcgagc tctggtgcgc cgacgccgcg      180
tccgccgcgg gccggttcgc cttcgccctg ggcgcgccgc tcgccgccag gtccgacctc      240
tccacgggga actccgcgca cgcctccctc ctcctccgct ccgcctccgt cgcgttcctc      300
ttcaccgccc cctacggcgg cgaccacggc gtcgcgcgcg acgcggccac caccgcctcc      360
atcccttcct tctccccagg cgccgcgcgg aggttcgccg cggaccacgg cctcgcggtg      420
cacgccgtgg cgctgcgcgt cgccgacgcg gccgacgcct tccgccagc  cgtcgcggcc      480 ggtgcgcgcc cggcgttcca gcccgccgac ctcggcggtg gcttcggcct cgcggaggtg      540
gagctctacg gcgacgtcgt gctccgcttc gtcagccacc cggacggcgc cgacgcgccc      600
ttcctcccgg gtttcgaggg cgtcagcaac ccgggcgccg tggactacgg cctccgccgg      660
ttcgaccacg tcgtcggcaa cgtgccggag ctcgctccgg tagccgcgta catctccggg      720
ttcaccgggt tccacgagtt cgccgagttc accgccgagg acgtgggcac cgccgagagc      780
ggcctcaact cggtggtgct cgccaacaac gcggagaccg tgctgctgcc gctcaacgag      840
ccggtgcacg gcaccaagcg gcggagccag atacagacgt acctggacca ccacggcggc      900 ccggggggtgc agcacatcgc gctggccagc gacgacgtgc tcgggacgct gagggagatg      960
cgggcgcgct ccgccatggg cggcttcgag ttcttggcgc cgccgccgcc caactactac     1020
gacggcgtgc ggcggcgcgc cggggacgtg ctctcggagg agcagatcaa cgagtgccag     1080
gagctcgggg tgctcgtgga cagggatgac caggggtgt  tgctccagat cttcaccaag     1140
ccagtaggag acaggccaac ctttttcttg gagatgatac aaaggattgg gtgcatggag     1200
aaggatgaga gtgggcagga gtaccagaag ggcggctgcg gcgggtttgg gaagggcaac     1260
ttctcggagc tgttcaagtc cattgaggag tatgagaaat cccttgaagc caagcaagcc     1320
cctacagttc aaggatccta g                                               1341
```

```
<210> SEQ ID NO 3
```

<211> LENGTH: 446
<212> TYPE: PRT
<213> ORGANISM: Oryza sativa

<400> SEQUENCE: 3

```
Met Pro Pro Thr Pro Thr Pro Thr Ala Thr Gly Ala Val Ser Ala
1               5                   10                  15

Ala Ala Ala Ala Gly Glu Asn Ala Gly Phe Arg Leu Val Gly His Arg
                20                  25                  30

Arg Phe Val Arg Ala Asn Pro Arg Ser Asp Arg Phe Gln Ala Leu Ala
            35                  40                  45

Phe His His Val Glu Leu Trp Cys Ala Asp Ala Ser Ala Ala Gly
    50                  55                  60

Arg Phe Ala Phe Ala Leu Gly Ala Pro Leu Ala Ala Arg Ser Asp Leu
65                  70                  75                  80

Ser Thr Gly Asn Ser Ala His Ala Ser Leu Leu Arg Ser Ala Ser
                85                  90                  95

Val Ala Phe Leu Phe Thr Ala Pro Tyr Gly Gly Asp His Gly Val Gly
            100                 105                 110

Ala Asp Ala Ala Thr Thr Ala Ser Ile Pro Ser Phe Ser Pro Gly Ala
        115                 120                 125

Ala Arg Arg Phe Ala Ala Asp His Gly Leu Ala Val His Ala Val Ala
130                 135                 140

Leu Arg Val Ala Asp Ala Asp Ala Phe Arg Ala Ser Val Ala Ala
145                 150                 155                 160

Gly Ala Arg Pro Ala Phe Gln Pro Ala Asp Leu Gly Gly Gly Phe Gly
                165                 170                 175

Leu Ala Glu Val Glu Leu Tyr Gly Asp Val Val Leu Arg Phe Val Ser
            180                 185                 190

His Pro Asp Gly Ala Asp Ala Pro Phe Leu Pro Gly Phe Glu Gly Val
        195                 200                 205

Ser Asn Pro Gly Ala Val Asp Tyr Gly Leu Arg Arg Phe Asp His Val
    210                 215                 220

Val Gly Asn Val Pro Glu Leu Ala Pro Val Ala Ala Tyr Ile Ser Gly
225                 230                 235                 240

Phe Thr Gly Phe His Glu Phe Ala Glu Phe Thr Ala Glu Asp Val Gly
                245                 250                 255

Thr Ala Glu Ser Gly Leu Asn Ser Val Val Leu Ala Asn Asn Ala Glu
            260                 265                 270

Thr Val Leu Leu Pro Leu Asn Glu Pro Val His Gly Thr Lys Arg Arg
        275                 280                 285

Ser Gln Ile Gln Thr Tyr Leu Asp His His Gly Gly Pro Gly Val Gln
    290                 295                 300

His Ile Ala Leu Ala Ser Asp Asp Val Leu Gly Thr Leu Arg Glu Met
305                 310                 315                 320

Arg Ala Arg Ser Ala Met Gly Gly Phe Glu Phe Leu Ala Pro Pro
                325                 330                 335

Pro Asn Tyr Tyr Asp Gly Val Arg Arg Arg Ala Gly Asp Val Leu Ser
            340                 345                 350

Glu Glu Gln Ile Asn Glu Cys Gln Glu Leu Gly Val Leu Val Asp Arg
        355                 360                 365

Asp Asp Gln Gly Val Leu Leu Gln Ile Phe Thr Lys Pro Val Gly Asp
370                 375                 380

Arg Pro Thr Phe Phe Leu Glu Met Ile Gln Arg Ile Gly Cys Met Glu
```

```
385                 390                 395                 400
Lys Asp Glu Ser Gly Gln Glu Tyr Gln Lys Gly Gly Cys Gly Phe
                405                 410                 415
Gly Lys Gly Asn Phe Ser Glu Leu Phe Lys Ser Ile Glu Glu Tyr Glu
                420                 425                 430
Lys Ser Leu Glu Ala Lys Gln Ala Pro Thr Val Gln Gly Ser
                435                 440                 445
```

<210> SEQ ID NO 4
<211> LENGTH: 201
<212> TYPE: DNA
<213> ORGANISM: Oryza sativa

<400> SEQUENCE: 4

```
atgcccacgg cggcggcggc ggaggaggag gaggaggagg agctaaggag cggcgcggta    60
cgtcgccggt gctgttctgc tttgtagccg ctgctgtcct ygtcggaaat gcctgccacg   120
ggctgttccc gcaggtattg agaaatgagc gctgagttcc tgacgcgttt aaatccactg   180
attagctgag ttcccttcca a                                             201
```

<210> SEQ ID NO 5
<211> LENGTH: 201
<212> TYPE: DNA
<213> ORGANISM: Oryza sativa

<400> SEQUENCE: 5

```
gagagtggag gaggaggacg agtggaggtg gaggtggcgc gcggctgcgc ggtgcgcttc    60
ttttttttt cttttttgt tcccgccgca accaaaggag rcaagcaaag gaagcaagca   120
aaagaaaaaa agcccgggaa tttacctggc gggaatgccc tacttggcag cgccgcccgt   180
ctctctccac aaacgccctg c                                             201
```

<210> SEQ ID NO 6
<211> LENGTH: 201
<212> TYPE: DNA
<213> ORGANISM: Oryza sativa

<400> SEQUENCE: 6

```
ttctatctca aggcggcaat agaatcatag atgctagagt ccagaagaag gccaaagact    60
tgaaattttc agttgagaat gagcaatcca aggtgatgct ygccaaatgt ctgatgaatt   120
gctcttgctc tgatgttgag cccgatgaag ttgttagctg ctgaggacat gatcggtacc   180
acctatattg acaaccctga t                                             201
```

<210> SEQ ID NO 7
<211> LENGTH: 201
<212> TYPE: DNA
<213> ORGANISM: Oryza sativa

<400> SEQUENCE: 7

```
tcagtgttca cggaccctac atggagttct cctaagttca actacaagag acatagccca    60
tagggtaatg ccctcacttt ccagctcttt aactatggag rtatcaatcg atcaatcacc   120
aatcggatgg taccaaatcc aaaacaacag ttggggaaaa ctgatcctac caacccagct   180
caactaattt tgcagtgcta c                                             201
```

<210> SEQ ID NO 8
<211> LENGTH: 33
<212> TYPE: DNA

<213> ORGANISM: Oryza sativa

<400> SEQUENCE: 8
gcacttcgca atcaacraat cattctgggc gta				33

<210> SEQ ID NO 9
<211> LENGTH: 33
<212> TYPE: DNA
<213> ORGANISM: Oryza sativa

<400> SEQUENCE: 9
ttccttacta acatatygcc tgagaattat aac				33

<210> SEQ ID NO 10
<211> LENGTH: 33
<212> TYPE: DNA
<213> ORGANISM: Oryza sativa

<400> SEQUENCE: 10
cggttttcat tccactkctt gttgacgagg ttt				33

<210> SEQ ID NO 11
<211> LENGTH: 33
<212> TYPE: DNA
<213> ORGANISM: Oryza sativa

<400> SEQUENCE: 11
acctaggcca ctaccaragg gacacatcgg cct				33

<210> SEQ ID NO 12
<211> LENGTH: 33
<212> TYPE: DNA
<213> ORGANISM: Oryza sativa

<400> SEQUENCE: 12
cgccgtgctc acagatwact acaacctcac cga				33

<210> SEQ ID NO 13
<211> LENGTH: 33
<212> TYPE: DNA
<213> ORGANISM: Oryza sativa

<400> SEQUENCE: 13
atcccgtagg acccatsaaa ggtgaccctc atc				33

<210> SEQ ID NO 14
<211> LENGTH: 33
<212> TYPE: DNA
<213> ORGANISM: Oryza sativa

<400> SEQUENCE: 14
aaaacttgag aaatgtwgct gtccataaca agg				33

<210> SEQ ID NO 15
<211> LENGTH: 33
<212> TYPE: DNA
<213> ORGANISM: Oryza sativa

<400> SEQUENCE: 15
tcatgccagc gacacawcaa gactagtttt gta				33

<210> SEQ ID NO 16
<211> LENGTH: 33

<212> TYPE: DNA
<213> ORGANISM: Oryza sativa

<400> SEQUENCE: 16
accaattcat tcgcatrgtt ggtaaattga tta                    33

<210> SEQ ID NO 17
<211> LENGTH: 33
<212> TYPE: DNA
<213> ORGANISM: Oryza sativa

<400> SEQUENCE: 17
agatatttct ttttcaytgt aaggcacttt gga                    33

<210> SEQ ID NO 18
<211> LENGTH: 33
<212> TYPE: DNA
<213> ORGANISM: Oryza sativa

<400> SEQUENCE: 18
agttgaatgt tgccaayggg tcagtcggtc aga                    33

<210> SEQ ID NO 19
<211> LENGTH: 33
<212> TYPE: DNA
<213> ORGANISM: Oryza sativa

<400> SEQUENCE: 19
ctgataactg tgtaacraag catccgtgac tga                    33

<210> SEQ ID NO 20
<211> LENGTH: 33
<212> TYPE: DNA
<213> ORGANISM: Oryza sativa

<400> SEQUENCE: 20
tgaatgagag cttcccraag tttgattgga aat                    33

<210> SEQ ID NO 21
<211> LENGTH: 33
<212> TYPE: DNA
<213> ORGANISM: Oryza sativa

<400> SEQUENCE: 21
gccactatat ctgtaarctg agtctgaatg gct                    33

<210> SEQ ID NO 22
<211> LENGTH: 33
<212> TYPE: DNA
<213> ORGANISM: Oryza sativa

<400> SEQUENCE: 22
tgttgcttta actgtgyaac ggaggctcga gaa                    33

<210> SEQ ID NO 23
<211> LENGTH: 33
<212> TYPE: DNA
<213> ORGANISM: Oryza sativa

<400> SEQUENCE: 23
gttctaacct gcaaacrtta gcaatcagaa gct                    33

<210> SEQ ID NO 24

```
<211> LENGTH: 33
<212> TYPE: DNA
<213> ORGANISM: Oryza sativa

<400> SEQUENCE: 24
taggaggaga tcaatckatt gcattgcaag ata                          33

<210> SEQ ID NO 25
<211> LENGTH: 33
<212> TYPE: DNA
<213> ORGANISM: Oryza sativa

<400> SEQUENCE: 25
taatttgtcg gcatttrgca tttctgtgaa act                          33

<210> SEQ ID NO 26
<211> LENGTH: 33
<212> TYPE: DNA
<213> ORGANISM: Oryza sativa

<400> SEQUENCE: 26
aattaaggat gcccagwact aattaactac acc                          33

<210> SEQ ID NO 27
<211> LENGTH: 33
<212> TYPE: DNA
<213> ORGANISM: Oryza sativa

<400> SEQUENCE: 27
caccgcagcc gctgctrtcg aacggtcagc cac                          33

<210> SEQ ID NO 28
<211> LENGTH: 33
<212> TYPE: DNA
<213> ORGANISM: Oryza sativa

<400> SEQUENCE: 28
aaaagacacc tgattamgcg gcagtccttg gaa                          33

<210> SEQ ID NO 29
<211> LENGTH: 33
<212> TYPE: DNA
<213> ORGANISM: Oryza sativa

<400> SEQUENCE: 29
tattgaaatt agcaggmaga tatgaaaagc aga                          33

<210> SEQ ID NO 30
<211> LENGTH: 41
<212> TYPE: DNA
<213> ORGANISM: Oryza sativa

<400> SEQUENCE: 30
gcctaaaaga ttgttttcgc rtattcacat aaacaagtat a                 41

<210> SEQ ID NO 31
<211> LENGTH: 33
<212> TYPE: DNA
<213> ORGANISM: Oryza sativa

<400> SEQUENCE: 31
ggattaatgc catactrcta ggacaaatta aaa                          33
```

<210> SEQ ID NO 32
<211> LENGTH: 33
<212> TYPE: DNA
<213> ORGANISM: Oryza sativa

<400> SEQUENCE: 32
cctctattgc tggcaayttg acatcaactc tgt                             33

<210> SEQ ID NO 33
<211> LENGTH: 33
<212> TYPE: DNA
<213> ORGANISM: Oryza sativa

<400> SEQUENCE: 33
ccacttgttt tcaatcmacc ttcggcacct gga                             33

<210> SEQ ID NO 34
<211> LENGTH: 33
<212> TYPE: DNA
<213> ORGANISM: Oryza sativa

<400> SEQUENCE: 34
gtactcatcc atacgcmtta tatatagact gta                             33

<210> SEQ ID NO 35
<211> LENGTH: 33
<212> TYPE: DNA
<213> ORGANISM: Oryza sativa

<400> SEQUENCE: 35
aaggtttcca gtgtccmgta agtaaatccc tcc                             33

<210> SEQ ID NO 36
<211> LENGTH: 33
<212> TYPE: DNA
<213> ORGANISM: Oryza sativa

<400> SEQUENCE: 36
atttgtcata agcagcrgtc tgaattcttg atc                             33

<210> SEQ ID NO 37
<211> LENGTH: 33
<212> TYPE: DNA
<213> ORGANISM: Oryza sativa

<400> SEQUENCE: 37
aatccaaggt gatgctygcc aaatgtctga tga                             33

<210> SEQ ID NO 38
<211> LENGTH: 33
<212> TYPE: DNA
<213> ORGANISM: Oryza sativa

<400> SEQUENCE: 38
gctagcttcc ttttctwgct atcttggtgc att                             33

<210> SEQ ID NO 39
<211> LENGTH: 33
<212> TYPE: DNA
<213> ORGANISM: Oryza sativa

<400> SEQUENCE: 39
gcagtggacc aagaccract aactgtatct att                             33

<210> SEQ ID NO 40
<211> LENGTH: 33
<212> TYPE: DNA
<213> ORGANISM: Oryza sativa

<400> SEQUENCE: 40
tttgccgaat cgggcayccg atccaaagtt ttg         33

<210> SEQ ID NO 41
<211> LENGTH: 33
<212> TYPE: DNA
<213> ORGANISM: Oryza sativa

<400> SEQUENCE: 41
gacgtgccgt atccgcwgta tcaggtattg cag         33

<210> SEQ ID NO 42
<211> LENGTH: 33
<212> TYPE: DNA
<213> ORGANISM: Oryza sativa

<400> SEQUENCE: 42
caagaagtgt cgtttgratc aactccggca cat         33

<210> SEQ ID NO 43
<211> LENGTH: 33
<212> TYPE: DNA
<213> ORGANISM: Oryza sativa

<400> SEQUENCE: 43
aggaagagga ctacttytat gctaaccctc aag         33

<210> SEQ ID NO 44
<211> LENGTH: 33
<212> TYPE: DNA
<213> ORGANISM: Oryza sativa

<400> SEQUENCE: 44
gatccccttg aagagtygaa taagttgctc tct         33

<210> SEQ ID NO 45
<211> LENGTH: 33
<212> TYPE: DNA
<213> ORGANISM: Oryza sativa

<400> SEQUENCE: 45
gttcttaacg gcccttraaa gcttacaaaa tta         33

<210> SEQ ID NO 46
<211> LENGTH: 33
<212> TYPE: DNA
<213> ORGANISM: Oryza sativa

<400> SEQUENCE: 46
gcggaacgcc tgtgacyaag ctccgtgatg aag         33

<210> SEQ ID NO 47
<211> LENGTH: 33
<212> TYPE: DNA
<213> ORGANISM: Oryza sativa

<400> SEQUENCE: 47
tcgtcaacta cgagttrgag ttctagacgt caa         33

```
<210> SEQ ID NO 48
<211> LENGTH: 33
<212> TYPE: DNA
<213> ORGANISM: Oryza sativa

<400> SEQUENCE: 48
aaaaggtagg aaaaaaktgt ggaaaagaag tcc                              33

<210> SEQ ID NO 49
<211> LENGTH: 33
<212> TYPE: DNA
<213> ORGANISM: Oryza sativa

<400> SEQUENCE: 49
gttccatcaa cgagtayttt gagatcaagc agt                              33

<210> SEQ ID NO 50
<211> LENGTH: 33
<212> TYPE: DNA
<213> ORGANISM: Oryza sativa

<400> SEQUENCE: 50
tgattgagca aaggcawact actgagggtt cta                              33

<210> SEQ ID NO 51
<211> LENGTH: 33
<212> TYPE: DNA
<213> ORGANISM: Oryza sativa

<400> SEQUENCE: 51
agcaagttta ggcccakgag gcgagcagca ttt                              33

<210> SEQ ID NO 52
<211> LENGTH: 33
<212> TYPE: DNA
<213> ORGANISM: Oryza sativa

<400> SEQUENCE: 52
cacagaggca tggactragg gcaaattttt ctt                              33

<210> SEQ ID NO 53
<211> LENGTH: 33
<212> TYPE: DNA
<213> ORGANISM: Oryza sativa

<400> SEQUENCE: 53
tagattgcca cttgtcrgtt taggagcgtt tat                              33

<210> SEQ ID NO 54
<211> LENGTH: 33
<212> TYPE: DNA
<213> ORGANISM: Oryza sativa

<400> SEQUENCE: 54
tatgggcata ggactaycct agcttttagc cca                              33

<210> SEQ ID NO 55
<211> LENGTH: 33
<212> TYPE: DNA
<213> ORGANISM: Oryza sativa

<400> SEQUENCE: 55
```
agcacgcagc tgcgcgktga gcataaagcg aac                                    33

<210> SEQ ID NO 56
<211> LENGTH: 33
<212> TYPE: DNA
<213> ORGANISM: Oryza sativa

<400> SEQUENCE: 56
tccaatatga tcgactratc cgctgcatag cga                                    33

<210> SEQ ID NO 57
<211> LENGTH: 33
<212> TYPE: DNA
<213> ORGANISM: Oryza sativa

<400> SEQUENCE: 57
tgaaggcgac tccgatkctg aatttctcat caa                                    33

<210> SEQ ID NO 58
<211> LENGTH: 33
<212> TYPE: DNA
<213> ORGANISM: Oryza sativa

<400> SEQUENCE: 58
aacgtgtgtc cgagttyatc ttagaagttg cct                                    33

<210> SEQ ID NO 59
<211> LENGTH: 33
<212> TYPE: DNA
<213> ORGANISM: Oryza sativa

<400> SEQUENCE: 59
ccactctacg gctgttkatc tgcatcattg cat                                    33

<210> SEQ ID NO 60
<211> LENGTH: 33
<212> TYPE: DNA
<213> ORGANISM: Oryza sativa

<400> SEQUENCE: 60
cgcttccatc aactgcmtta attctgattc cga                                    33

<210> SEQ ID NO 61
<211> LENGTH: 33
<212> TYPE: DNA
<213> ORGANISM: Oryza sativa

<400> SEQUENCE: 61
ttatgcaatg ttttatsgct gaagcagtgc ata                                    33

<210> SEQ ID NO 62
<211> LENGTH: 33
<212> TYPE: DNA
<213> ORGANISM: Oryza sativa

<400> SEQUENCE: 62
atgattatgt cagttaygat gcgggcgctt taa                                    33

<210> SEQ ID NO 63
<211> LENGTH: 33
<212> TYPE: DNA
<213> ORGANISM: Oryza sativa

<400> SEQUENCE: 63
cgagggcgct tgtcawgtc ctgaacacac atc                                  33

<210> SEQ ID NO 64
<211> LENGTH: 33
<212> TYPE: DNA
<213> ORGANISM: Oryza sativa

<400> SEQUENCE: 64
aaggttatcg ttgcctrtca aaattcttgc gat                                 33

<210> SEQ ID NO 65
<211> LENGTH: 33
<212> TYPE: DNA
<213> ORGANISM: Oryza sativa

<400> SEQUENCE: 65
actgtactac acatgayacc tgcggtgaag taa                                 33

<210> SEQ ID NO 66
<211> LENGTH: 33
<212> TYPE: DNA
<213> ORGANISM: Oryza sativa

<400> SEQUENCE: 66
tagctgccag aagctaytca acatgccct aaa                                  33

<210> SEQ ID NO 67
<211> LENGTH: 33
<212> TYPE: DNA
<213> ORGANISM: Oryza sativa

<400> SEQUENCE: 67
gtcgtccggg accgatygag ttcatcagac acc                                 33

<210> SEQ ID NO 68
<211> LENGTH: 33
<212> TYPE: DNA
<213> ORGANISM: Oryza sativa

<400> SEQUENCE: 68
acgacaactt tctgcaktttt ggacttgctc gcg                                33

<210> SEQ ID NO 69
<211> LENGTH: 33
<212> TYPE: DNA
<213> ORGANISM: Oryza sativa

<400> SEQUENCE: 69
actggcactc ataatargat gctttgttac aaa                                 33

<210> SEQ ID NO 70
<211> LENGTH: 33
<212> TYPE: DNA
<213> ORGANISM: Oryza sativa

<400> SEQUENCE: 70
ctccgcgcat aaggttycca catattcctc tca                                 33

<210> SEQ ID NO 71
<211> LENGTH: 33
<212> TYPE: DNA
<213> ORGANISM: Oryza sativa

<400> SEQUENCE: 71
tgcagctcgt ttggctygcg agctaagacc cta    33

<210> SEQ ID NO 72
<211> LENGTH: 33
<212> TYPE: DNA
<213> ORGANISM: Oryza sativa

<400> SEQUENCE: 72
tcctctaacc cattgtyttg acattcctt taa    33

<210> SEQ ID NO 73
<211> LENGTH: 33
<212> TYPE: DNA
<213> ORGANISM: Oryza sativa

<400> SEQUENCE: 73
gttcccgtga gtccgtract tagcagcact tgt    33

<210> SEQ ID NO 74
<211> LENGTH: 33
<212> TYPE: DNA
<213> ORGANISM: Oryza sativa

<400> SEQUENCE: 74
ctgattaaca ttttctratt ggcggagtca ata    33

<210> SEQ ID NO 75
<211> LENGTH: 33
<212> TYPE: DNA
<213> ORGANISM: Oryza sativa

<400> SEQUENCE: 75
cgtttctctc aggccakgct tggaagctac ttt    33

<210> SEQ ID NO 76
<211> LENGTH: 33
<212> TYPE: DNA
<213> ORGANISM: Oryza sativa

<400> SEQUENCE: 76
tcttcctcct tggaagmagc tacagcagca gcg    33

<210> SEQ ID NO 77
<211> LENGTH: 33
<212> TYPE: DNA
<213> ORGANISM: Oryza sativa

<400> SEQUENCE: 77
cttcctgcac aagatcraag ctcgccgcta aca    33

<210> SEQ ID NO 78
<211> LENGTH: 33
<212> TYPE: DNA
<213> ORGANISM: Oryza sativa

<400> SEQUENCE: 78
caagggtagc gagtacyaac cagaccatat atg    33

<210> SEQ ID NO 79
<211> LENGTH: 33
<212> TYPE: DNA
<213> ORGANISM: Oryza sativa

```
<400> SEQUENCE: 79
gatctttaga gagacayaca ttgcacagca ccc                                33

<210> SEQ ID NO 80
<211> LENGTH: 33
<212> TYPE: DNA
<213> ORGANISM: Oryza sativa

<400> SEQUENCE: 80
catgagcttg tgtatartac tgacaacagc ttt                                33

<210> SEQ ID NO 81
<211> LENGTH: 33
<212> TYPE: DNA
<213> ORGANISM: Oryza sativa

<400> SEQUENCE: 81
acctatcagc ccacgaygtt ggtaaaaaga ggg                                33

<210> SEQ ID NO 82
<211> LENGTH: 33
<212> TYPE: DNA
<213> ORGANISM: Oryza sativa

<400> SEQUENCE: 82
aagtatgacc agaagtwtta tgatttgaca ggt                                33

<210> SEQ ID NO 83
<211> LENGTH: 33
<212> TYPE: DNA
<213> ORGANISM: Oryza sativa

<400> SEQUENCE: 83
ttgtgcttgc tgcattmaga ggggaagaca tgt                                33

<210> SEQ ID NO 84
<211> LENGTH: 33
<212> TYPE: DNA
<213> ORGANISM: Oryza sativa

<400> SEQUENCE: 84
ttccacttaa attgctsagt aaatccctgc tcc                                33

<210> SEQ ID NO 85
<211> LENGTH: 33
<212> TYPE: DNA
<213> ORGANISM: Oryza sativa

<400> SEQUENCE: 85
tgttaggcaa aaggacwgtg tgaccaccac ctc                                33

<210> SEQ ID NO 86
<211> LENGTH: 33
<212> TYPE: DNA
<213> ORGANISM: Oryza sativa

<400> SEQUENCE: 86
cgtacgttgt agagttyaat gacaactagc cgg                                33

<210> SEQ ID NO 87
<211> LENGTH: 33
<212> TYPE: DNA
```

<213> ORGANISM: Oryza sativa

<400> SEQUENCE: 87
aacaccaatc gatttcrtat gcttgatcaa atg     33

<210> SEQ ID NO 88
<211> LENGTH: 33
<212> TYPE: DNA
<213> ORGANISM: Oryza sativa

<400> SEQUENCE: 88
tagccgctgc tgtcctygtc ggaaatgcct gcc     33

<210> SEQ ID NO 89
<211> LENGTH: 33
<212> TYPE: DNA
<213> ORGANISM: Oryza sativa

<400> SEQUENCE: 89
gccgcaacca aggagrcaa gcaaaggaag caa     33

<210> SEQ ID NO 90
<211> LENGTH: 33
<212> TYPE: DNA
<213> ORGANISM: Oryza sativa

<400> SEQUENCE: 90
acgagcggtg agctgtyata cagtgacaag cat     33

<210> SEQ ID NO 91
<211> LENGTH: 33
<212> TYPE: DNA
<213> ORGANISM: Oryza sativa

<400> SEQUENCE: 91
ctatttgtta atcaggytaa gccacaagag gag     33

<210> SEQ ID NO 92
<211> LENGTH: 33
<212> TYPE: DNA
<213> ORGANISM: Oryza sativa

<400> SEQUENCE: 92
aattccgtct catcatyggg tggaggagcg aaa     33

<210> SEQ ID NO 93
<211> LENGTH: 33
<212> TYPE: DNA
<213> ORGANISM: Oryza sativa

<400> SEQUENCE: 93
ttgtgtttcg tcagagygta cgggaaaaga gac     33

<210> SEQ ID NO 94
<211> LENGTH: 33
<212> TYPE: DNA
<213> ORGANISM: Oryza sativa

<400> SEQUENCE: 94
tcctctcatg catgctyggt attgcagtgt gca     33

<210> SEQ ID NO 95
<211> LENGTH: 33

```
<212> TYPE: DNA
<213> ORGANISM: Oryza sativa

<400> SEQUENCE: 95
aaacagcgaa cagcaasgcg cccatggaga ttc                                33

<210> SEQ ID NO 96
<211> LENGTH: 33
<212> TYPE: DNA
<213> ORGANISM: Oryza sativa

<400> SEQUENCE: 96
aactctacat gctttaycaa tggcaccaca ctt                                33

<210> SEQ ID NO 97
<211> LENGTH: 33
<212> TYPE: DNA
<213> ORGANISM: Oryza sativa

<400> SEQUENCE: 97
tgatctgcaa caggaawcgc gattgcgaat cag                                33

<210> SEQ ID NO 98
<211> LENGTH: 33
<212> TYPE: DNA
<213> ORGANISM: Oryza sativa

<400> SEQUENCE: 98
ctcttggccg tcacgamcag tgttgtactt ctg                                33

<210> SEQ ID NO 99
<211> LENGTH: 33
<212> TYPE: DNA
<213> ORGANISM: Oryza sativa

<400> SEQUENCE: 99
attactagtt tcttgayaaa gtatgcaatt gtg                                33

<210> SEQ ID NO 100
<211> LENGTH: 33
<212> TYPE: DNA
<213> ORGANISM: Oryza sativa

<400> SEQUENCE: 100
gggcttgttg caggctygag gcagcaacct cga                                33

<210> SEQ ID NO 101
<211> LENGTH: 33
<212> TYPE: DNA
<213> ORGANISM: Oryza sativa

<400> SEQUENCE: 101
tgcattccac tgttatygct gatgataaca aca                                33

<210> SEQ ID NO 102
<211> LENGTH: 33
<212> TYPE: DNA
<213> ORGANISM: Oryza sativa

<400> SEQUENCE: 102
tctccatatc tgcaagmttc tccaacacag cat                                33

<210> SEQ ID NO 103
```

```
<211> LENGTH: 33
<212> TYPE: DNA
<213> ORGANISM: Oryza sativa

<400> SEQUENCE: 103
caggtatcag atgttasaca gatgcttcct gga                                33

<210> SEQ ID NO 104
<211> LENGTH: 33
<212> TYPE: DNA
<213> ORGANISM: Oryza sativa

<400> SEQUENCE: 104
ttaggtatag gtgcaamtga gctagttcca agt                                33

<210> SEQ ID NO 105
<211> LENGTH: 33
<212> TYPE: DNA
<213> ORGANISM: Oryza sativa

<400> SEQUENCE: 105
ggcccatttg acgaggwaag cccaataacc caa                                33

<210> SEQ ID NO 106
<211> LENGTH: 33
<212> TYPE: DNA
<213> ORGANISM: Oryza sativa

<400> SEQUENCE: 106
tggtctatca aatcaawcca acttgcattt tac                                33

<210> SEQ ID NO 107
<211> LENGTH: 33
<212> TYPE: DNA
<213> ORGANISM: Oryza sativa

<400> SEQUENCE: 107
caacatccaa cggctgmata gtgcaaagag taa                                33

<210> SEQ ID NO 108
<211> LENGTH: 33
<212> TYPE: DNA
<213> ORGANISM: Oryza sativa

<400> SEQUENCE: 108
ctctttaact atggagrtat caatcgatca atc                                33

<210> SEQ ID NO 109
<211> LENGTH: 33
<212> TYPE: DNA
<213> ORGANISM: Oryza sativa

<400> SEQUENCE: 109
tacatgactt gtgctcrgaa aatggttcgt tca                                33

<210> SEQ ID NO 110
<211> LENGTH: 33
<212> TYPE: DNA
<213> ORGANISM: Oryza sativa

<400> SEQUENCE: 110
gatcgagggc tccgacract ttacttcatc ttc                                33
```

<210> SEQ ID NO 111
<211> LENGTH: 33
<212> TYPE: DNA
<213> ORGANISM: Oryza sativa

<400> SEQUENCE: 111
gattgattct cacttgyagg tgacccatga ggc        33

<210> SEQ ID NO 112
<211> LENGTH: 33
<212> TYPE: DNA
<213> ORGANISM: Oryza sativa

<400> SEQUENCE: 112
acgcgtctcg gtcgtaytgg atacgtgcat tta        33

<210> SEQ ID NO 113
<211> LENGTH: 33
<212> TYPE: DNA
<213> ORGANISM: Oryza sativa

<400> SEQUENCE: 113
gctattccat acctaayggt gcaaagccat cat        33

<210> SEQ ID NO 114
<211> LENGTH: 33
<212> TYPE: DNA
<213> ORGANISM: Oryza sativa

<400> SEQUENCE: 114
gttggtaaac aaaaaakaat gaggcaagct aat        33

<210> SEQ ID NO 115
<211> LENGTH: 33
<212> TYPE: DNA
<213> ORGANISM: Oryza sativa

<400> SEQUENCE: 115
ttcttctaga ttgcagkatt ataggctaca gag        33

<210> SEQ ID NO 116
<211> LENGTH: 33
<212> TYPE: DNA
<213> ORGANISM: Oryza sativa

<400> SEQUENCE: 116
ctatatgcat gcttatmtcg ttgatttcgc tat        33

<210> SEQ ID NO 117
<211> LENGTH: 33
<212> TYPE: DNA
<213> ORGANISM: Oryza sativa

<400> SEQUENCE: 117
ctgtatgttc agctatstca gaacctttga ttt        33

<210> SEQ ID NO 118
<211> LENGTH: 33
<212> TYPE: DNA
<213> ORGANISM: Oryza sativa

<400> SEQUENCE: 118
gcattacagg attctarcat gacgaacaaa cat        33

```
<210> SEQ ID NO 119
<211> LENGTH: 33
<212> TYPE: DNA
<213> ORGANISM: Oryza sativa

<400> SEQUENCE: 119
gatttgctcg atagtaygtc ttaacaacat atc                          33

<210> SEQ ID NO 120
<211> LENGTH: 33
<212> TYPE: DNA
<213> ORGANISM: Oryza sativa

<400> SEQUENCE: 120
actctaggct cacttcrctg tcgggattac cct                          33

<210> SEQ ID NO 121
<211> LENGTH: 33
<212> TYPE: DNA
<213> ORGANISM: Oryza sativa

<400> SEQUENCE: 121
ccactatttg ctcccaraga agtggaatgg agc                          33

<210> SEQ ID NO 122
<211> LENGTH: 33
<212> TYPE: DNA
<213> ORGANISM: Oryza sativa

<400> SEQUENCE: 122
ctctcacatg ttctgcyaat ggatcaacta gtt                          33

<210> SEQ ID NO 123
<211> LENGTH: 33
<212> TYPE: DNA
<213> ORGANISM: Oryza sativa

<400> SEQUENCE: 123
acaaacagtg gcaacayttt taaagtctga ctg                          33

<210> SEQ ID NO 124
<211> LENGTH: 33
<212> TYPE: DNA
<213> ORGANISM: Oryza sativa

<400> SEQUENCE: 124
tgctcgccag ctaaccsttg tctcagccca tga                          33

<210> SEQ ID NO 125
<211> LENGTH: 33
<212> TYPE: DNA
<213> ORGANISM: Oryza sativa

<400> SEQUENCE: 125
tgagaagaac aggcagwaca gacatacata tag                          33

<210> SEQ ID NO 126
<211> LENGTH: 41
<212> TYPE: DNA
<213> ORGANISM: Oryza sativa

<400> SEQUENCE: 126
aaagttccgc acaagtttaa ygttacactt actaaaccag t                 41
```

<210> SEQ ID NO 127
<211> LENGTH: 33
<212> TYPE: DNA
<213> ORGANISM: Oryza sativa

<400> SEQUENCE: 127
cgattgaatg ttgcaawttt tgatgagcag agc                                    33

<210> SEQ ID NO 128
<211> LENGTH: 33
<212> TYPE: DNA
<213> ORGANISM: Oryza sativa

<400> SEQUENCE: 128
ttgatcgagg ccgcttkctg tcgcctatcg acc                                    33

<210> SEQ ID NO 129
<211> LENGTH: 33
<212> TYPE: DNA
<213> ORGANISM: Oryza sativa

<400> SEQUENCE: 129
tttaaatttt tatttgmttg cacaatggtc aat                                    33

<210> SEQ ID NO 130
<211> LENGTH: 33
<212> TYPE: DNA
<213> ORGANISM: Oryza sativa

<400> SEQUENCE: 130
accgaagttg ctgcacytaa gcgcccatgt cct                                    33

<210> SEQ ID NO 131
<211> LENGTH: 33
<212> TYPE: DNA
<213> ORGANISM: Oryza sativa

<400> SEQUENCE: 131
ctgccggcct gcgctayaac aagccagata cct                                    33

<210> SEQ ID NO 132
<211> LENGTH: 33
<212> TYPE: DNA
<213> ORGANISM: Oryza sativa

<400> SEQUENCE: 132
atttgctttg ccacacyatc taggctgaca tga                                    33

<210> SEQ ID NO 133
<211> LENGTH: 33
<212> TYPE: DNA
<213> ORGANISM: Oryza sativa

<400> SEQUENCE: 133
accggcaagc ccaagakaga gaaaagtgtg ctg                                    33

<210> SEQ ID NO 134
<211> LENGTH: 33
<212> TYPE: DNA
<213> ORGANISM: Oryza sativa

<400> SEQUENCE: 134
tctattgaag taggttrttg aatgatctga acg    33

<210> SEQ ID NO 135
<211> LENGTH: 33
<212> TYPE: DNA
<213> ORGANISM: Oryza sativa

<400> SEQUENCE: 135
gtacatgtcc aaagtaygta cagacgcttg gct    33

<210> SEQ ID NO 136
<211> LENGTH: 33
<212> TYPE: DNA
<213> ORGANISM: Oryza sativa

<400> SEQUENCE: 136
taaccatcaa gtatcakgtg attcctacca cgt    33

<210> SEQ ID NO 137
<211> LENGTH: 33
<212> TYPE: DNA
<213> ORGANISM: Oryza sativa

<400> SEQUENCE: 137 gtaattttc tgggtcygcc gctggatagg atg    33

<210> SEQ ID NO 138
<211> LENGTH: 33
<212> TYPE: DNA
<213> ORGANISM: Oryza sativa

<400> SEQUENCE: 138
agctcttgca ggtctgraca tcctcgtgca aca    33

<210> SEQ ID NO 139
<211> LENGTH: 33
<212> TYPE: DNA
<213> ORGANISM: Oryza sativa

<400> SEQUENCE: 139
cgtttagctg atgtcawcca aaacatcgtt tgt    33

<210> SEQ ID NO 140
<211> LENGTH: 33
<212> TYPE: DNA
<213> ORGANISM: Oryza sativa

<400> SEQUENCE: 140
agtagcggta gttaaawgca aacgtgaccg taa    33

<210> SEQ ID NO 141
<211> LENGTH: 33
<212> TYPE: DNA
<213> ORGANISM: Oryza sativa

<400> SEQUENCE: 141
atatgcttta tgcattygga tgacagatga act    33

<210> SEQ ID NO 142
<211> LENGTH: 33
<212> TYPE: DNA
<213> ORGANISM: Oryza sativa

<400> SEQUENCE: 142
tctgaaggga ccagccyagt tttcgcttta gcc                33

<210> SEQ ID NO 143
<211> LENGTH: 33
<212> TYPE: DNA
<213> ORGANISM: Oryza sativa

<400> SEQUENCE: 143
ggatgagatg gtcggcytga cccacaatcc ttt                33

<210> SEQ ID NO 144
<211> LENGTH: 33
<212> TYPE: DNA
<213> ORGANISM: Oryza sativa

<400> SEQUENCE: 144
cagaaaggag gtgcgawaac aactgcgaca gat                33

<210> SEQ ID NO 145
<211> LENGTH: 33
<212> TYPE: DNA
<213> ORGANISM: Oryza sativa

<400> SEQUENCE: 145
ccatgttcac aatttcstaa aacttactaa ttc                33

<210> SEQ ID NO 146
<211> LENGTH: 33
<212> TYPE: DNA
<213> ORGANISM: Oryza sativa

<400> SEQUENCE: 146
atctatcaat ccctacygtc catccacgtt gca                33

<210> SEQ ID NO 147
<211> LENGTH: 33
<212> TYPE: DNA
<213> ORGANISM: Oryza sativa

<400> SEQUENCE: 147
aagggcacct gttttyggc gtcaccgagg gcg                 33

<210> SEQ ID NO 148
<211> LENGTH: 33
<212> TYPE: DNA
<213> ORGANISM: Oryza sativa

<400> SEQUENCE: 148
tggacgtgac ctcattmtgg gatgttttag gca                33

<210> SEQ ID NO 149
<211> LENGTH: 33
<212> TYPE: DNA
<213> ORGANISM: Oryza sativa

<400> SEQUENCE: 149
atgacgggct tggtacytac gaaacgagtt gat                33

<210> SEQ ID NO 150
<211> LENGTH: 33
<212> TYPE: DNA
<213> ORGANISM: Oryza sativa

<400> SEQUENCE: 150
gagaaaaatg tcgaagytaa tctagttcga gca        33

<210> SEQ ID NO 151
<211> LENGTH: 33
<212> TYPE: DNA
<213> ORGANISM: Oryza sativa

<400> SEQUENCE: 151
gcggcaactt ttgtcarggt cttctaggtt atc        33

<210> SEQ ID NO 152
<211> LENGTH: 33
<212> TYPE: DNA
<213> ORGANISM: Oryza sativa

<400> SEQUENCE: 152
atcgggatct actggarcgc agatcagctt ttc        33

<210> SEQ ID NO 153
<211> LENGTH: 33
<212> TYPE: DNA
<213> ORGANISM: Oryza sativa

<400> SEQUENCE: 153
atagccaaaa gtctgtrcac ccgctaggac gac        33

<210> SEQ ID NO 154
<211> LENGTH: 33
<212> TYPE: DNA
<213> ORGANISM: Oryza sativa

<400> SEQUENCE: 154
cctcggagtt cacctcrata tacaccagca aag        33

<210> SEQ ID NO 155
<211> LENGTH: 33
<212> TYPE: DNA
<213> ORGANISM: Oryza sativa

<400> SEQUENCE: 155
gccgattttg gaagccyagc ggttgctgat cca        33

<210> SEQ ID NO 156
<211> LENGTH: 33
<212> TYPE: DNA
<213> ORGANISM: Oryza sativa

<400> SEQUENCE: 156
cagagagcct agagtcstat aagacagcta aat        33

<210> SEQ ID NO 157
<211> LENGTH: 33
<212> TYPE: DNA
<213> ORGANISM: Oryza sativa

<400> SEQUENCE: 157
atttttcgta actttcrttc actcagtctt agc        33

<210> SEQ ID NO 158
<211> LENGTH: 33
<212> TYPE: DNA
<213> ORGANISM: Oryza sativa

```
<400> SEQUENCE: 158
atttcctgaa aaacgcrgtg agaaatggtg cag                                    33

<210> SEQ ID NO 159
<211> LENGTH: 33
<212> TYPE: DNA
<213> ORGANISM: Oryza sativa

<400> SEQUENCE: 159
tcaaatgcat actgtcrata ttccctgtgc ttc                                    33

<210> SEQ ID NO 160
<211> LENGTH: 33
<212> TYPE: DNA
<213> ORGANISM: Oryza sativa

<400> SEQUENCE: 160
aggctgagaa aaacacrggg cacaaatttg ttt                                    33

<210> SEQ ID NO 161
<211> LENGTH: 33
<212> TYPE: DNA
<213> ORGANISM: Oryza sativa

<400> SEQUENCE: 161
cgatagcaaa gcagcgyatt acagaaccac gac                                    33

<210> SEQ ID NO 162
<211> LENGTH: 33
<212> TYPE: DNA
<213> ORGANISM: Oryza sativa

<400> SEQUENCE: 162
tcatcacact aatatgytaa ggaccggaat caa                                    33

<210> SEQ ID NO 163
<211> LENGTH: 33
<212> TYPE: DNA
<213> ORGANISM: Oryza sativa

<400> SEQUENCE: 163
taggcccgga tccaaaygct tcattcaatg aga                                    33

<210> SEQ ID NO 164
<211> LENGTH: 33
<212> TYPE: DNA
<213> ORGANISM: Oryza sativa

<400> SEQUENCE: 164
tccaatgtct ctgctcygtg ctcgaaccag aac                                    33

<210> SEQ ID NO 165
<211> LENGTH: 33
<212> TYPE: DNA
<213> ORGANISM: Oryza sativa

<400> SEQUENCE: 165
tttgctgtta gtaccamgaa atgctagact atg                                    33

<210> SEQ ID NO 166
<211> LENGTH: 33
<212> TYPE: DNA
```

<210> SEQ ID NO 166
<211> LENGTH: 33
<212> TYPE: DNA
<213> ORGANISM: Oryza sativa

<400> SEQUENCE: 166
tctatcaatc acccatygtt ttttatctaa aac                    33

<210> SEQ ID NO 167
<211> LENGTH: 33
<212> TYPE: DNA
<213> ORGANISM: Oryza sativa

<400> SEQUENCE: 167
ttaatgctat aatctcrtta cgaagcattc aaa                    33

<210> SEQ ID NO 168
<211> LENGTH: 33
<212> TYPE: DNA
<213> ORGANISM: Oryza sativa

<400> SEQUENCE: 168
ttaaggccaa cattttraaa gtgtacaaca tgg                    33

<210> SEQ ID NO 169
<211> LENGTH: 33
<212> TYPE: DNA
<213> ORGANISM: Oryza sativa

<400> SEQUENCE: 169
tgggacaaag tggcagyaat ctttcaaggc aag                    33

<210> SEQ ID NO 170
<211> LENGTH: 33
<212> TYPE: DNA
<213> ORGANISM: Oryza sativa

<400> SEQUENCE: 170
ccaacacatg tgcagcktat caaccggacg ctg                    33

<210> SEQ ID NO 171
<211> LENGTH: 33
<212> TYPE: DNA
<213> ORGANISM: Oryza sativa

<400> SEQUENCE: 171
tgtagaatca ttcagakttta cttctgttat gtt                   33

<210> SEQ ID NO 172
<211> LENGTH: 33
<212> TYPE: DNA
<213> ORGANISM: Oryza sativa

<400> SEQUENCE: 172 tttttctgt actcacmcat tgttctgtta gta                     33

<210> SEQ ID NO 173
<211> LENGTH: 33
<212> TYPE: DNA
<213> ORGANISM: Oryza sativa

<400> SEQUENCE: 173
tttcggtttg agcttaygat tgttatatgc aac                    33

<210> SEQ ID NO 174
<211> LENGTH: 33

<212> TYPE: DNA
<213> ORGANISM: Oryza sativa

<400> SEQUENCE: 174
tcaatctgaa caggacraat gggatagcca ctt                33

<210> SEQ ID NO 175
<211> LENGTH: 33
<212> TYPE: DNA
<213> ORGANISM: Oryza sativa

<400> SEQUENCE: 175
cgtatcttta ccggcaygtc ttctgctatc ccg                33

<210> SEQ ID NO 176
<211> LENGTH: 33
<212> TYPE: DNA
<213> ORGANISM: Oryza sativa

<400> SEQUENCE: 176
tatatggatc acagtaygtg tttgcacagc aca                33

<210> SEQ ID NO 177
<211> LENGTH: 33
<212> TYPE: DNA
<213> ORGANISM: Oryza sativa

<400> SEQUENCE: 177
tcatgatgcc tggtgcytga tcatgacgag ttg                33

<210> SEQ ID NO 178
<211> LENGTH: 33
<212> TYPE: DNA
<213> ORGANISM: Oryza sativa

<400> SEQUENCE: 178
aggcggctgg tagctgmtta tcccggcgcc att                33

<210> SEQ ID NO 179
<211> LENGTH: 33
<212> TYPE: DNA
<213> ORGANISM: Oryza sativa

<400> SEQUENCE: 179
tcaacgatgc acatggycag tgtcattggg aat                33

<210> SEQ ID NO 180
<211> LENGTH: 33
<212> TYPE: DNA
<213> ORGANISM: Oryza sativa

<400> SEQUENCE: 180
agtgagagtt gcacagytat gccacgactg aac                33

<210> SEQ ID NO 181
<211> LENGTH: 33
<212> TYPE: DNA
<213> ORGANISM: Oryza sativa

<400> SEQUENCE: 181
agacctatgg atggacrtga taaccaaggg ctt                33

<210> SEQ ID NO 182

```
<211> LENGTH: 33
<212> TYPE: DNA
<213> ORGANISM: Oryza sativa

<400> SEQUENCE: 182
aagccaaaac aggagtraat tgcaactcca tct                          33

<210> SEQ ID NO 183
<211> LENGTH: 33
<212> TYPE: DNA
<213> ORGANISM: Oryza sativa

<400> SEQUENCE: 183
ggtggtttga aagcacmttg tgcatgctca agc                          33

<210> SEQ ID NO 184
<211> LENGTH: 33
<212> TYPE: DNA
<213> ORGANISM: Oryza sativa

<400> SEQUENCE: 184
ggacaccgaa ctatcgrcgg catcgttcat cag                          33

<210> SEQ ID NO 185
<211> LENGTH: 33
<212> TYPE: DNA
<213> ORGANISM: Oryza sativa

<400> SEQUENCE: 185
ctgattcagc cctactyttg taattttcct ggc                          33

<210> SEQ ID NO 186
<211> LENGTH: 33
<212> TYPE: DNA
<213> ORGANISM: Oryza sativa

<400> SEQUENCE: 186
aatgtgcaac cacttartct gtgtgtggta gta                          33

<210> SEQ ID NO 187
<211> LENGTH: 33
<212> TYPE: DNA
<213> ORGANISM: Oryza sativa

<400> SEQUENCE: 187
acagaagtat tcgtcamgtg agccaaaaga aga                          33

<210> SEQ ID NO 188
<211> LENGTH: 33
<212> TYPE: DNA
<213> ORGANISM: Oryza sativa

<400> SEQUENCE: 188
catttactct tttcctygtc tttgcagatc tac                          33

<210> SEQ ID NO 189
<211> LENGTH: 33
<212> TYPE: DNA
<213> ORGANISM: Oryza sativa

<400> SEQUENCE: 189
tcttgtttgc gcaggakatt atgaagggtc aca                          33
```

```
<210> SEQ ID NO 190
<211> LENGTH: 33
<212> TYPE: DNA
<213> ORGANISM: Oryza sativa

<400> SEQUENCE: 190
tattattcta tcgcctsatc agtgtgtgca tgt                                33

<210> SEQ ID NO 191
<211> LENGTH: 33
<212> TYPE: DNA
<213> ORGANISM: Oryza sativa

<400> SEQUENCE: 191
cacccactcc tagttgmaga tgatgatcaa gat                                33

<210> SEQ ID NO 192
<211> LENGTH: 33
<212> TYPE: DNA
<213> ORGANISM: Oryza sativa

<400> SEQUENCE: 192
ctgtgctttc ctgccaygag tccttttgaa agt                                33

<210> SEQ ID NO 193
<211> LENGTH: 33
<212> TYPE: DNA
<213> ORGANISM: Oryza sativa

<400> SEQUENCE: 193 ttcttttttct tgatttstcg cccgacccga cga                              33

<210> SEQ ID NO 194
<211> LENGTH: 33
<212> TYPE: DNA
<213> ORGANISM: Oryza sativa

<400> SEQUENCE: 194
actcaagagt ttcacgkccg aatgcgaaac act                                33

<210> SEQ ID NO 195
<211> LENGTH: 33
<212> TYPE: DNA
<213> ORGANISM: Oryza sativa

<400> SEQUENCE: 195
ctcatgtcat gtggtaygcc aatgcataaa act                                33

<210> SEQ ID NO 196
<211> LENGTH: 33
<212> TYPE: DNA
<213> ORGANISM: Oryza sativa

<400> SEQUENCE: 196
tacatttgct actcatyaca tgctgatcaa cta                                33

<210> SEQ ID NO 197
<211> LENGTH: 33
<212> TYPE: DNA
<213> ORGANISM: Oryza sativa

<400> SEQUENCE: 197
tgaagctgca gaagtarcta tgagtggaga taa                                33
```

<210> SEQ ID NO 198
<211> LENGTH: 33
<212> TYPE: DNA
<213> ORGANISM: Oryza sativa

<400> SEQUENCE: 198
cgcccacttc ggcaaaygtc agttaactcg atc                         33

<210> SEQ ID NO 199
<211> LENGTH: 33
<212> TYPE: DNA
<213> ORGANISM: Oryza sativa

<400> SEQUENCE: 199
ccacttgcat aaaaggrata caatgctcaa tcc                         33

<210> SEQ ID NO 200
<211> LENGTH: 2501
<212> TYPE: DNA
<213> ORGANISM: Oryza sativa

<400> SEQUENCE: 200
cctgttctgc taggaataat agaactacat actgctatga ttttccactg gtgagttgac    60
tgctccctta tattcaatgc attaccatag caaattcata ttcgttcatg ttgtcaaaat   120
aagccgatga aaattcaaaa ctgtaggcat ttgaaactgc agtgaggaag tcatggtcct   180
ctagtacctc tggtgcttct aaaggtgttg aaaatgccca atgttatgtt aaagctacag   240
agttggtatt tgcggacaaa catgggtcat ggggcactcc tttagttcaa atggaccggc   300
ctgctgggct caatgacatt ggtatggtag cttggacctt gaagatgtcc actcctgaat   360
ttcctagtgg tagggagatt attgttgttg caaatgatat tacgttcaga gctggatcat   420
ttggcccaag ggaagatgca ttttttgaag ctgttaccaa cctagcctgt gagaagaaac   480
ttcctcttat ttatttggca gcaaattctg gtgctcgaat tggcatagca gatgaagtga   540
aatcttgctt ccgtgttggg tggtctgatg atggcagccc tgaacgtggg tttcagtaca   600
tttatctaag cgaagaagac tatgctcgta ttggcacttc tgtcatagca cataagatgc   660
agctagacag tggtgaaatt aggtgggtta ttgattctgt tgtgggcaag gaagatggac   720
ttggtgtgga gaatatacat ggaagtgctg ctattgccag tgcttattct agggcatata   780
aggagacatt tacacttaca tttgtgactg gaagaactgt tggaataggg gcttatcttg   840
ctcgacttgg catccggtgc atacagcgtc ttgaccagcc tattattctt acaggctatt   900
ctgcactgaa caagcttctt gggcgggaag tgtacagctc ccacatgcag ttgggtggtc   960
ccaaaatcat ggcaactaat ggtgttgtcc atcttactgt ttcagatgac cttgaaggcg  1020
tttctaatat attgaggtgg ctcagttatg ttcctgccta cattggtgga ccacttccag  1080
taacaacacc gttggaccca ccggacagac ctgttgcata cattcctgag aactcgtgtg  1140
atcctcgagc ggctatccgt ggtgttgatg acagccaagg gaaatggtta ggtggtatgt  1200
ttgataaaga cagctttgtg gaaacatttg aaggttgggc taagacagtg gttactggca  1260
gagcaaagct tggtggaatt ccagtgggtg tgatagctgt ggagactcag accatgatgc  1320
aaactatccc tgctgacccc tggtcagcttg attcccgtga gcaatctgtt cctcgtgctg  1380
gacaagtgtg gtttccagat tctgcaacca agactcgcga ggcattgctg gacttcaacc  1440
gtgaaggatt acctctgttc atcctcgcta actggagagg cttctctggt ggacaaagag  1500
atctttttga aggaattctt caggctggct cgactattgt tgagaacctt aggacataca  1560

```
atcagcctgc ctttgtctac attcccatgg ctgcagagct acgaggaggg gcttgggttg   1620
tggttgatag caagataaac ccagaccgca ttgagtgcta tgctgagagg actgcaaaag   1680
gcaatgttct ggaaccgcaa gggttaattg agatcaagtt caggtcagag gaactccagg   1740
attgcatgag tcggcttgac ccaacattaa ttgatctgaa agcaaaactc gaagtagcaa   1800
ataaaaatgg aagtgctgac acaaaatcgc ttcaagaaaa tatagaagct cgaacaaaac   1860
agttgatgcc tctatatact cagattgcga tacggtttgc tgaattgcat gatacatccc   1920
tcagaatggc tgcgaaaggt gtgattaaga aagttgtgga ctgggaagaa tcacgatctt   1980
tcttctataa agattacgg aggaggatct ctgaggatgt tcttgcaaaa gaaattagag   2040
ctgtagcagg tgagcagttt tcccaccaac cagcaatcga gctgatcaag aaatggtatt   2100
cagcttcaca tgcagctgaa tgggatgatg acgatgcttt tgttgcttgg atggataacc   2160
ctgaaaacta caaggattat attcaatatc ttaaggctca aagagtatcc caatccctct   2220
caagtctttc agattccagc tcagatttgc aagccctgcc acagggtctt tccatgttac   2280
tagataaggt aattagctta ctgatgctta tataaattct tttcattac atatggctgg   2340 agaactatct aatcaaataa tgattataat tccaatcgtt cttttatgc cattatgatc   2400 ttctgaaatt tccttctttg gacacttatt cagatggatc cctctagaag agctcaactt   2460
gttgaagaaa tcaggaaggt ccttggttga atcatatgat g                      2501

<210> SEQ ID NO 201
<211> LENGTH: 2501
<212> TYPE: DNA
<213> ORGANISM: Oryza sativa

<400> SEQUENCE: 201
cctgttctgc taggaataat agaactacat actgctatga ttttccactg gtgagttgac     60
tgctccctta tattcaatgc attaccatag caaattcata ttcgttcatg ttgtcaaaat    120
aagccgatga aaattcaaaa ctgtaggcat ttgaaactgc agtgaggaag tcatggtcct    180
ctagtacctc tggtgcttct aaaggtgttg aaaatgccca atgttatgtt aaagctacag    240
agttggtatt tgcggacaaa catgggtcat ggggcactcc tttagttcaa atggaccggc    300
ctgctgggct caatgacatt ggtatggtag cttggacctt gaagatgtcc actcctgaat    360
ttcctagtgg tagggagatt attgttgttg caatgatat tacgttcaga gctggatcat    420
ttggcccaag ggaagatgca tttttttgaag ctgttaccaa cctagcctgt gagaagaaac    480
ttcctcttat ttatttggca gcaaattctg gtgctcgaat tggcatagca gatgaagtga    540
aatcttgctt ccgtgttggg tggtctgatg atggcagccc tgaacgtggg tttcagtaca    600
tttatctaag cgaagaagac tatgctcgta ttggcacttc tgtcatagca cataagatgc    660
agctagacag tggtgaaatt aggtgggtta ttgattctgt tgtgggcaag gaagatggac    720
ttggtgtgga gaatatacat ggaagtgctg ctattgccag tgcttattct agggcatata    780
aggagacatt tacacttaca tttgtgactg gaagaactgt tggaatagga gcttatcttg    840
ctcgacttgg catccggtgc atacagcgtc ttgaccagcc tattattctt acaggctatt    900
ctgcactgaa caagcttctt gggcgggaag tgtacagctc ccacatgcag ttgggtggtc    960
ccaaaatcat ggcaactaat ggtgttgtcc atcttactgt ttcagatgac cttgaaggcg   1020
tttctaatat attgaggtgg ctcagttatg ttcctgccta cattggtgga ccacttccag   1080
taacaacacc gttggaccca ccggacagac ctgttgcata cattcctgag aactcgtgtg   1140
```

```
atcctcgagc ggctatccgt ggtgttgatg acagccaagg gaaatggtta ggtggtatgt    1200
ttgataaaga cagcttttgtg gaaacatttg aaggttgggc taagacagtg gttactggca    1260
gagcaaagct tggtggaatt ccagtgggtg tgatagctgt ggagactcag accatgatgc    1320
aaactatccc tgctgacccct ggtcagcttg attcccgtga gcaatctgtt cctcgtgctg    1380
gacaagtgtg gtttccagat tctgcaacca agactgcgca ggcattgctg gacttcaacc    1440
gtgaaggatt acctctgttc atcctcgcta actggagagg cttctctggt ggacaaagag    1500 atcttttttga aggaattctt caggctggct cgactattgt tgagaacctt aggacataca    1560
atcagcctgc ctttgtctac attcccatgg ctgcagagct acgaggaggg gcttgggttg    1620
tggttgatag caagataaac ccagaccgca ttgagtgcta tgctgagagg actgcaaaag    1680
gcaatgttct ggaaccgcaa gggttaattg agatcaagtt caggtcagag gaactccagg    1740
attgcatgag tcggcttgac ccaacattaa ttgatctgaa agcaaaactc gaagtagcaa    1800
ataaaaatgg aagtgctgac acaaaatcgc ttcaagaaaa tatagaagct cgaacaaaac    1860
agttgatgcc tctatatact cagattgcga tacggtttgc tgaattgcat gatacatccc    1920
tcagaatggc tgcgaaaggt gtgattaaga aagttgtgga ctgggaagaa tcacgatctt    1980
tcttctataa gagattacgg aggaggatct ctgaggatgt tcttgcaaaa gaaattagag    2040
ctgtagcagg tgagcagttt tcccaccaac cagcaatcga gctgatcaag aaatggtatt    2100
cagcttcaca tgcagctgaa tgggatgatg acgatgcttt tgttgcttgg atggataacc    2160
ctgaaaacta caaggattat attcaatatc ttaaggctca aagagtatcc caatccctct    2220
caagtctttc agattccagc tcagatttgc aagccctgcc acagggtctt tccatgttac    2280
tagataaggt aattagctta ctgatgctta tataaattct ttttcattac atatggctgg    2340
agaactatct aatcaaataa tgattataat tccaatcgtt cttttttatgc cattatgatc    2400 ttctgaaatt tccttctttg gacacttatt cagatggatc cctctagaag agctcaactt    2460
gttgaagaaa tcaggaaggt ccttggttga atcatatgat g                        2501
```

<210> SEQ ID NO 202
<211> LENGTH: 2501
<212> TYPE: DNA
<213> ORGANISM: Oryza sativa

<400> SEQUENCE: 202

```
cctgttctgc taggaataat agaactacat actgctatga ttttccactg gtgagttgac     60
tgctccctta tattcaatgc attaccatag caaattcata ttcgttcatg ttgtcaaaat    120
aagccgatga aaattcaaaa ctgtaggcat ttgaaactgc agtgaggaag tcatggtcct    180
ctagtacctc tggtgcttct aaaggtgttg aaaatgccca atgttatgtt aaagctacag    240
agttggtatt tgcggacaaa catgggtcat ggggcactcc tttagttcaa atggaccggc    300
ctgctgggct caatgacatt ggtatggtag cttggacctt gaagatgtcc actcctgaat    360
ttcctagtgg tagggagatt attgttgttg caaatgatat tacgttcaga gctggatcat    420
ttggcccaag ggaagatgca tttttttgaag ctgttaccaa cctagcctgt gagaagaaac    480
ttcctcttat ttatttggca gcaaattctg gtgctcgaat tggcatagca gatgaagtga    540
aatcttgctt ccgtgttggg tggtctgatg atggcagccc tgaacgtggg tttcagtaca    600
tttatctaag cgaagaagac tatgctcgta ttggcacttc tgtcatagca cataagatgc    660
agctagacag tggtgaaatt aggtgggtta ttgattctgt tgtgggcaag gaagatggac    720
ttggtgtgga gaatatacat ggaagtgctg ctattgccag tgcttattct agggcatata    780
```

```
aggagacatt tacacttaca tttgtgactg gaagaactgt tggaatagga gcttatcttg    840
ctcgacttgg catccggtgc atacagcgtc ttgaccagcc tattattctt acaggctatt    900
ctgcactgaa caagcttctt gggcgggaag tgtacagctc ccacatgcag ttgggtggtc    960
ccaaaatcat ggcaactaat ggtgttgtcc atcttactgt ttcagatgac cttgaaggcg   1020
tttctaatat attgaggtgg ctcagttatg ttcctgccta cattggtgga ccacttccag   1080
taacaacacc gttggaccca ccggacagac ctgttgcata cattcctgag aactcgtgtg   1140
atcctcgagc ggctatccgt ggtgttgatg acagccaagg gaaatggtta ggtggtatgt   1200
ttgataaaga cagctttgtg gaaacatttg aaggttgggc taagacagtg gttactggca   1260
gagcaaagct tggtggaatt ccagtgggtg tgatagctgt ggagactcag accatgatgc   1320
aaactatccc tgctgaccct ggtcagcttg attcccgtga gcaatctgtt cctcgtgctg   1380
gacaagtgtg gtttccagat tctgcaacca agactgcgca ggcattgctg gacttcaacc   1440
gtgaaggatt acctctgttc atcctcgcta actggagagg cttctctggt ggacaaagag   1500
atctttttga aggaattctt caggctggct cgactattgt tgagaacctt aggacataca   1560
atcagcctgc ctttgtctac attcccatgg ctgcagagct acgaggaggg gcttgggttg   1620
tggttgatag caagataaac ccagaccgca ttgagtgcta tgctgagagg actgcaaaaa   1680
gcaatgttct ggaaccgcaa gggttaattg agatcaagtt caggtcagag gaactccagg   1740
attgcatgag tcggcttgac ccaacattaa ttgatctgaa agcaaaactc gaagtagcaa   1800
ataaaaatgg aagtgctgac acaaaatcgc ttcaagaaaa tatagaagct cgaacaaaac   1860
agttgatgcc tctatatact cagattgcga tacggtttgc tgaattgcat gatacatccc   1920
tcagaatggc tgcgaaaggt gtgattaaga aagttgtgga ctgggaagaa tcacgatctt   1980
tcttctataa gagattacgg aggaggatct ctgaggatgt tcttgcaaaa gaaattagag   2040
ctgtagcagg tgagcagttt tcccaccaac cagcaatcga gctgatcaag aaatggtatt   2100
cagcttcaca tgcagctgaa tgggatgatg acgatgcttt tgttgcttgg atggataacc   2160
ctgaaaacta caaggattat attcaatatc ttaaggctca agagtatccc aatccctct    2220 caagtctttc agattccagc tcagatttgc aagccctgcc acagggtctt tccatgttac   2280
tagataaggt aattagctta ctgatgctta tataaattct tttcattac atatggctgg    2340 agaactatct aatcaaataa tgattataat tccaatcgtt ctttttatgc cattatgatc   2400
ttctgaaatt ccttctttg gacacttatt cagatggatc cctctagaag agctcaactt    2460
gttgaagaaa tcaggaaggt ccttggttga atcatatgat g                       2501
```

<210> SEQ ID NO 203
<211> LENGTH: 674
<212> TYPE: PRT
<213> ORGANISM: Oryza sativa

<400> SEQUENCE: 203

Met Asp Arg Pro Ala Gly Leu Asn Asp Ile Gly Met Val Ala Trp Thr
1               5                  10                  15

Leu Lys Met Ser Thr Pro Glu Phe Pro Ser Gly Arg Glu Ile Ile Val
            20                  25                  30

Val Ala Asn Asp Ile Thr Phe Arg Ala Gly Ser Phe Gly Pro Arg Glu
        35                  40                  45

Asp Ala Phe Phe Glu Ala Val Thr Asn Leu Ala Cys Glu Lys Lys Leu
    50                  55                  60

-continued

```
Pro Leu Ile Tyr Leu Ala Ala Asn Ser Gly Ala Arg Ile Gly Ile Ala
 65                  70                  75                  80

Asp Glu Val Lys Ser Cys Phe Arg Val Gly Trp Ser Asp Asp Gly Ser
                 85                  90                  95

Pro Glu Arg Gly Phe Gln Tyr Ile Tyr Leu Ser Glu Glu Asp Tyr Ala
            100                 105                 110

Arg Ile Gly Thr Ser Val Ile Ala His Lys Met Gln Leu Asp Ser Gly
            115                 120                 125

Glu Ile Arg Trp Val Ile Asp Ser Val Val Gly Lys Glu Asp Gly Leu
        130                 135                 140

Gly Val Glu Asn Ile His Gly Ser Ala Ala Ile Ala Ser Ala Tyr Ser
145                 150                 155                 160

Arg Ala Tyr Lys Glu Thr Phe Thr Leu Thr Phe Val Thr Gly Arg Thr
                165                 170                 175

Val Gly Ile Gly Ala Tyr Leu Ala Arg Leu Gly Ile Arg Cys Ile Gln
            180                 185                 190

Arg Leu Asp Gln Pro Ile Ile Leu Thr Gly Tyr Ser Ala Leu Asn Lys
        195                 200                 205

Leu Leu Gly Arg Glu Val Tyr Ser Ser His Met Gln Leu Gly Gly Pro
210                 215                 220

Lys Ile Met Ala Thr Asn Gly Val Val His Leu Thr Val Ser Asp Asp
225                 230                 235                 240

Leu Glu Gly Val Ser Asn Ile Leu Arg Trp Leu Ser Tyr Val Pro Ala
                245                 250                 255

Tyr Ile Gly Gly Pro Leu Pro Val Thr Thr Pro Leu Asp Pro Pro Asp
            260                 265                 270

Arg Pro Val Ala Tyr Ile Pro Glu Asn Ser Cys Asp Pro Arg Ala Ala
        275                 280                 285

Ile Arg Gly Val Asp Asp Ser Gln Gly Lys Trp Leu Gly Gly Met Phe
    290                 295                 300

Asp Lys Asp Ser Phe Val Glu Thr Phe Glu Gly Trp Ala Lys Thr Val
305                 310                 315                 320

Val Thr Gly Arg Ala Lys Leu Gly Gly Ile Pro Val Gly Val Ile Ala
                325                 330                 335

Val Glu Thr Gln Thr Met Met Gln Thr Ile Pro Ala Asp Pro Gly Gln
            340                 345                 350

Leu Asp Ser Arg Glu Gln Ser Val Pro Arg Ala Gly Gln Val Trp Phe
        355                 360                 365

Pro Asp Ser Ala Thr Lys Thr Ala Gln Ala Leu Leu Asp Phe Asn Arg
    370                 375                 380

Glu Gly Leu Pro Leu Phe Ile Leu Ala Asn Trp Arg Gly Phe Ser Gly
385                 390                 395                 400

Gly Gln Arg Asp Leu Phe Glu Gly Ile Leu Gln Ala Gly Ser Thr Ile
                405                 410                 415

Val Glu Asn Leu Arg Thr Tyr Asn Gln Pro Ala Phe Val Tyr Ile Pro
            420                 425                 430

Met Ala Ala Glu Leu Arg Gly Gly Ala Trp Val Val Asp Ser Lys
        435                 440                 445

Ile Asn Pro Asp Arg Ile Glu Cys Tyr Ala Glu Arg Thr Ala Lys Gly
    450                 455                 460

Asn Val Leu Glu Pro Gln Gly Leu Ile Glu Ile Lys Phe Arg Ser Glu
465                 470                 475                 480

Glu Leu Gln Asp Cys Met Ser Arg Leu Asp Pro Thr Leu Ile Asp Leu
```

```
            485                 490                 495
Lys Ala Lys Leu Glu Val Ala Asn Lys Asn Gly Ser Ala Asp Thr Lys
            500                 505                 510

Ser Leu Gln Glu Asn Ile Glu Ala Arg Thr Lys Gln Leu Met Pro Leu
            515                 520                 525

Tyr Thr Gln Ile Ala Ile Arg Phe Ala Glu Leu His Asp Thr Ser Leu
            530                 535                 540

Arg Met Ala Ala Lys Gly Val Ile Lys Val Val Asp Trp Glu Glu
545                 550                 555                 560

Ser Arg Ser Phe Phe Tyr Lys Arg Leu Arg Arg Ile Ser Glu Asp
                    565                 570                 575

Val Leu Ala Lys Glu Ile Arg Ala Val Ala Gly Glu Gln Phe Ser His
            580                 585                 590

Gln Pro Ala Ile Glu Leu Ile Lys Lys Trp Tyr Ser Ala Ser His Ala
            595                 600                 605

Ala Glu Trp Asp Asp Asp Ala Phe Val Ala Trp Met Asp Asn Pro
610                 615                 620

Glu Asn Tyr Lys Asp Tyr Ile Gln Tyr Leu Lys Ala Gln Arg Val Ser
625                 630                 635                 640

Gln Ser Leu Ser Ser Leu Ser Asp Ser Ser Asp Leu Gln Ala Leu
                    645                 650                 655

Pro Gln Gly Leu Ser Met Leu Leu Asp Lys Val Ile Ser Leu Leu Met
            660                 665                 670

Leu Ile

<210> SEQ ID NO 204
<211> LENGTH: 674
<212> TYPE: PRT
<213> ORGANISM: Oryza sativa

<400> SEQUENCE: 204

Met Asp Arg Pro Ala Gly Leu Asn Asp Ile Gly Met Val Ala Trp Thr
1               5                   10                  15

Leu Lys Met Ser Thr Pro Glu Phe Pro Ser Gly Arg Glu Ile Ile Val
            20                  25                  30

Val Ala Asn Asp Ile Thr Phe Arg Ala Gly Ser Phe Gly Pro Arg Glu
        35                  40                  45

Asp Ala Phe Phe Glu Ala Val Thr Asn Leu Ala Cys Glu Lys Lys Leu
    50                  55                  60

Pro Leu Ile Tyr Leu Ala Ala Asn Ser Gly Ala Arg Ile Gly Ile Ala
65                  70                  75                  80

Asp Glu Val Lys Ser Cys Phe Arg Val Gly Trp Ser Asp Asp Gly Ser
                85                  90                  95

Pro Glu Arg Gly Phe Gln Tyr Ile Tyr Leu Ser Glu Glu Asp Tyr Ala
            100                 105                 110

Arg Ile Gly Thr Ser Val Ile Ala His Lys Met Gln Leu Asp Ser Gly
        115                 120                 125

Glu Ile Arg Trp Val Ile Asp Ser Val Val Gly Lys Glu Asp Gly Leu
    130                 135                 140

Gly Val Glu Asn Ile His Gly Ser Ala Ala Ile Ala Ser Ala Tyr Ser
145                 150                 155                 160

Arg Ala Tyr Lys Glu Thr Phe Thr Leu Thr Phe Val Thr Gly Arg Thr
                165                 170                 175

Val Gly Ile Gly Ala Tyr Leu Ala Arg Leu Gly Ile Arg Cys Ile Gln
```

-continued

```
            180                 185                 190
Arg Leu Asp Gln Pro Ile Ile Leu Thr Gly Tyr Ser Ala Leu Asn Lys
            195                 200                 205
Leu Leu Gly Arg Glu Val Tyr Ser Ser His Met Gln Leu Gly Gly Pro
            210                 215                 220
Lys Ile Met Ala Thr Asn Gly Val Val His Leu Thr Val Ser Asp Asp
225                 230                 235                 240
Leu Glu Gly Val Ser Asn Ile Leu Arg Trp Leu Ser Tyr Val Pro Ala
                245                 250                 255
Tyr Ile Gly Gly Pro Leu Pro Val Thr Thr Pro Leu Asp Pro Pro Asp
                260                 265                 270
Arg Pro Val Ala Tyr Ile Pro Glu Asn Ser Cys Asp Pro Arg Ala Ala
            275                 280                 285
Ile Arg Gly Val Asp Asp Ser Gln Gly Lys Trp Leu Gly Gly Met Phe
            290                 295                 300
Asp Lys Asp Ser Phe Val Glu Thr Phe Glu Gly Trp Ala Lys Thr Val
305                 310                 315                 320
Val Thr Gly Arg Ala Lys Leu Gly Gly Ile Pro Val Gly Val Ile Ala
                325                 330                 335
Val Glu Thr Gln Thr Met Met Gln Thr Ile Pro Ala Asp Pro Gly Gln
            340                 345                 350
Leu Asp Ser Arg Glu Gln Ser Val Pro Arg Ala Gly Gln Val Trp Phe
            355                 360                 365
Pro Asp Ser Ala Thr Lys Thr Ala Gln Ala Leu Leu Asp Phe Asn Arg
            370                 375                 380
Glu Gly Leu Pro Leu Phe Ile Leu Ala Asn Trp Arg Gly Phe Ser Gly
385                 390                 395                 400
Gly Gln Arg Asp Leu Phe Glu Gly Ile Leu Gln Ala Gly Ser Thr Ile
                405                 410                 415
Val Glu Asn Leu Arg Thr Tyr Asn Gln Pro Ala Phe Val Tyr Ile Pro
            420                 425                 430
Met Ala Ala Glu Leu Arg Gly Gly Ala Trp Val Val Val Asp Ser Lys
            435                 440                 445
Ile Asn Pro Asp Arg Ile Glu Cys Tyr Ala Glu Arg Thr Ala Lys Gly
            450                 455                 460
Asn Val Leu Glu Pro Gln Gly Leu Ile Glu Ile Lys Phe Arg Ser Glu
465                 470                 475                 480
Glu Leu Gln Asp Cys Met Ser Arg Leu Asp Pro Thr Leu Ile Asp Leu
                485                 490                 495
Lys Ala Lys Leu Glu Val Ala Asn Lys Asn Gly Ser Ala Asp Thr Lys
            500                 505                 510
Ser Leu Gln Glu Asn Ile Glu Ala Arg Thr Lys Gln Leu Met Pro Leu
            515                 520                 525
Tyr Thr Gln Ile Ala Ile Arg Phe Ala Glu Leu His Asp Thr Ser Leu
            530                 535                 540
Arg Met Ala Ala Lys Gly Val Ile Lys Lys Val Val Asp Trp Glu Glu
545                 550                 555                 560
Ser Arg Ser Phe Phe Tyr Lys Arg Leu Arg Arg Ile Ser Glu Asp
                565                 570                 575
Val Leu Ala Lys Glu Ile Arg Ala Val Ala Gly Glu Gln Phe Ser His
            580                 585                 590
Gln Pro Ala Ile Glu Leu Ile Lys Lys Trp Tyr Ser Ala Ser His Ala
            595                 600                 605
```

-continued

Ala Glu Trp Asp Asp Asp Ala Phe Val Ala Trp Met Asp Asn Pro
        610             615                 620

Glu Asn Tyr Lys Asp Tyr Ile Gln Tyr Leu Lys Ala Gln Arg Val Ser
625             630                 635                 640

Gln Ser Leu Ser Ser Leu Ser Asp Ser Ser Asp Leu Gln Ala Leu
            645                 650                 655

Pro Gln Gly Leu Ser Met Leu Leu Asp Lys Val Ile Ser Leu Leu Met
            660                 665                 670

Leu Ile

<210> SEQ ID NO 205
<211> LENGTH: 674
<212> TYPE: PRT
<213> ORGANISM: Oryza sativa

<400> SEQUENCE: 205

Met Asp Arg Pro Ala Gly Leu Asn Asp Ile Gly Met Val Ala Trp Thr
1               5                   10                  15

Leu Lys Met Ser Thr Pro Glu Phe Pro Ser Gly Arg Glu Ile Ile Val
            20                  25                  30

Val Ala Asn Asp Ile Thr Phe Arg Ala Gly Ser Phe Gly Pro Arg Glu
        35                  40                  45

Asp Ala Phe Phe Glu Ala Val Thr Asn Leu Ala Cys Glu Lys Lys Leu
50                  55                  60

Pro Leu Ile Tyr Leu Ala Ala Asn Ser Gly Ala Arg Ile Gly Ile Ala
65              70                  75                  80

Asp Glu Val Lys Ser Cys Phe Arg Val Gly Trp Ser Asp Asp Gly Ser
                85                  90                  95

Pro Glu Arg Gly Phe Gln Tyr Ile Tyr Leu Ser Glu Glu Asp Tyr Ala
            100                 105                 110

Arg Ile Gly Thr Ser Val Ile Ala His Lys Met Gln Leu Asp Ser Gly
        115                 120                 125

Glu Ile Arg Trp Val Ile Asp Ser Val Val Gly Lys Glu Asp Gly Leu
    130                 135                 140

Gly Val Glu Asn Ile His Gly Ser Ala Ala Ile Ala Ser Ala Tyr Ser
145                 150                 155                 160

Arg Ala Tyr Lys Glu Thr Phe Thr Leu Thr Phe Val Thr Gly Arg Thr
                165                 170                 175

Val Gly Ile Gly Ala Tyr Leu Ala Arg Leu Gly Ile Arg Cys Ile Gln
            180                 185                 190

Arg Leu Asp Gln Pro Ile Ile Leu Thr Gly Tyr Ser Ala Leu Asn Lys
        195                 200                 205

Leu Leu Gly Arg Glu Val Tyr Ser Ser His Met Gln Leu Gly Gly Pro
210                 215                 220

Lys Ile Met Ala Thr Asn Gly Val Val His Leu Thr Val Ser Asp Asp
225                 230                 235                 240

Leu Glu Gly Val Ser Asn Ile Leu Arg Trp Leu Ser Tyr Val Pro Ala
                245                 250                 255

Tyr Ile Gly Gly Pro Leu Pro Val Thr Thr Pro Leu Asp Pro Pro Asp
            260                 265                 270

Arg Pro Val Ala Tyr Ile Pro Glu Asn Ser Cys Asp Pro Arg Ala Ala
        275                 280                 285

Ile Arg Gly Val Asp Asp Ser Gln Gly Lys Trp Leu Gly Gly Met Phe
    290                 295                 300

Asp Lys Asp Ser Phe Val Glu Thr Phe Glu Gly Trp Ala Lys Thr Val
305                 310                 315                 320

Val Thr Gly Arg Ala Lys Leu Gly Gly Ile Pro Val Gly Val Ile Ala
            325                 330                 335

Val Glu Thr Gln Thr Met Met Gln Thr Ile Pro Ala Asp Pro Gly Gln
            340                 345                 350

Leu Asp Ser Arg Glu Gln Ser Val Pro Arg Ala Gly Gln Val Trp Phe
            355                 360                 365

Pro Asp Ser Ala Thr Lys Thr Ala Gln Ala Leu Leu Asp Phe Asn Arg
            370                 375                 380

Glu Gly Leu Pro Leu Phe Ile Leu Ala Asn Trp Arg Gly Phe Ser Gly
385                 390                 395                 400

Gly Gln Arg Asp Leu Phe Glu Gly Ile Leu Gln Ala Gly Ser Thr Ile
            405                 410                 415

Val Glu Asn Leu Arg Thr Tyr Asn Gln Pro Ala Phe Val Tyr Ile Pro
            420                 425                 430

Met Ala Ala Glu Leu Arg Gly Gly Ala Trp Val Val Asp Ser Lys
            435                 440                 445

Ile Asn Pro Asp Arg Ile Glu Cys Tyr Ala Glu Arg Thr Ala Lys Ser
450                 455                 460

Asn Val Leu Glu Pro Gln Gly Leu Ile Glu Ile Lys Phe Arg Ser Glu
465                 470                 475                 480

Glu Leu Gln Asp Cys Met Ser Arg Leu Asp Pro Thr Leu Ile Asp Leu
            485                 490                 495

Lys Ala Lys Leu Glu Val Ala Asn Lys Asn Gly Ser Ala Asp Thr Lys
            500                 505                 510

Ser Leu Gln Glu Asn Ile Glu Ala Arg Thr Lys Gln Leu Met Pro Leu
            515                 520                 525

Tyr Thr Gln Ile Ala Ile Arg Phe Ala Glu Leu His Asp Thr Ser Leu
            530                 535                 540

Arg Met Ala Ala Lys Gly Val Ile Lys Lys Val Val Asp Trp Glu Glu
545                 550                 555                 560

Ser Arg Ser Phe Phe Tyr Lys Arg Leu Arg Arg Ile Ser Glu Asp
            565                 570                 575

Val Leu Ala Lys Glu Ile Arg Ala Val Ala Gly Glu Gln Phe Ser His
            580                 585                 590

Gln Pro Ala Ile Glu Leu Ile Lys Lys Trp Tyr Ser Ala Ser His Ala
            595                 600                 605

Ala Glu Trp Asp Asp Asp Ala Phe Val Ala Trp Met Asp Asn Pro
610                 615                 620

Glu Asn Tyr Lys Asp Tyr Ile Gln Tyr Leu Lys Ala Gln Arg Val Ser
625                 630                 635                 640

Gln Ser Leu Ser Ser Leu Ser Asp Ser Ser Asp Leu Gln Ala Leu
            645                 650                 655

Pro Gln Gly Leu Ser Met Leu Leu Asp Lys Val Ile Ser Leu Leu Met
            660                 665                 670

Leu Ile

<210> SEQ ID NO 206
<211> LENGTH: 201
<212> TYPE: DNA
<213> ORGANISM: Oryza sativa

<400> SEQUENCE: 206

```
ataaagatga ggtgtttgat gaattaaagg ccgcagggtt gaagaggcca tgtagcttta    60
cagatatttc cagtgaaaat gctttgcttc ttgaatttga kacagcaact gatgcagctg   120
ctgcgaaagc ccatattagg cgccagcttc atccagatgt ctgttcccag acaagaata    180 cttctggtca tgaactttt g                                              201
```

<210> SEQ ID NO 207
<211> LENGTH: 201
<212> TYPE: DNA
<213> ORGANISM: Oryza sativa

<400> SEQUENCE: 207

```
tcacatgatc tgcaactgtc aacagtctta ccggaattgg attctgaagg tggatactcc    60
acctgtccac cataagtcct tatttgtcag aggttacaat ygcatgatgt gtctatactc   120
tatactgcaa agatgaatac taacaagttt ttcttgggct taaaagaaga aaaactagga   180
acagcctcac tagtttgcta g                                             201
```

<210> SEQ ID NO 208
<211> LENGTH: 201
<212> TYPE: DNA
<213> ORGANISM: Oryza sativa

<400> SEQUENCE: 208

```
tgtttcaagt ttggttgctg aaaaacgtac ggacaaacca tgaactaact tgctattttg    60
ctccacatgg gtttgtctcg aagcaaccag gaattgatca rcttcggtgg tttgccaaga   120
acatgaaacc tggggataag gatttttttc gactttgcta atgctggtcg tctggattag   180
gaacagaaca ggtattgcta c                                             201
```

<210> SEQ ID NO 209
<211> LENGTH: 201
<212> TYPE: DNA
<213> ORGANISM: Oryza sativa

<400> SEQUENCE: 209

```
agtctaaatg ggctgcactt tgattgggct gggttcatat gagattaggg gaaaaaacac    60
gaacattcca gtaaatggg gagtgtgaac tgtgaagaag rgggtaaacg gtgtgcggac    120
gtgagacgag aaaagcatga gagaaaacga tctgtgtgca tgcatagggc tggacgaaaa   180
gctcgtgact cgttagctcg c                                             201
```

<210> SEQ ID NO 210
<211> LENGTH: 201
<212> TYPE: DNA
<213> ORGANISM: Oryza sativa

<400> SEQUENCE: 210

```
tagggcttct gatagccctc catctgtccg tcctttgccc gtttgcttct tggcctaaac    60
caccgaaaag gtgggtccgt tttgctggac gcctggaata ytcttcaact cgattggaac   120
agcaggctcc gtgtatgtgt aactatggct gtgtttagat ctaaagttta gattcaaagt   180
atagatttaa acttcagtca t                                             201
```

<210> SEQ ID NO 211
<211> LENGTH: 201
<212> TYPE: DNA
<213> ORGANISM: Oryza sativa

<400> SEQUENCE: 211

```
tgctgattct caggctgatt ctacttggtt ggtagaaaat ctacttatcc aggaacaagc    60
gtagggtaac ttttccttttt tttctcagct atgtgaaaag rgagaaaact cgctacactt   120
tataggaaat gaactactct tctaccgacg gatatcctaa aggctatcct ctggtacctc   180
ggccttacgc taactcaaaa c                                              201
```

<210> SEQ ID NO 212
<211> LENGTH: 201
<212> TYPE: DNA
<213> ORGANISM: Oryza sativa

<400> SEQUENCE: 212

```
cgatcccagg gaggttgtgg aagtgcttct catgaccttc gaggcactgc ggcgtaggca    60
tcttcaattg gatgagacac aagagactag caaacgtgca racctgaagg ctggtgccat   120
catgttggcc agtaatctga gggctaacat tgggaagagg attggagctg tccctggagt   180
tgaagtaggg gatattttct a                                              201
```

<210> SEQ ID NO 213
<211> LENGTH: 201
<212> TYPE: DNA
<213> ORGANISM: Oryza sativa

<400> SEQUENCE: 213

```
aattccaatt tcatcccatt tgtcccattc cctcctgatt actttgccaa gaaaaataag    60
cctgtggaga attcatcaga tgcaggaata gtgccagaag rccctccatc agctgaaaaa   120
ttaccagaaa caaaatattc atctggaaat ctgggaaatt ttcagaacag ctcacaggtg   180
atgggcagtc aggcagcaaa c                                              201
```

<210> SEQ ID NO 214
<211> LENGTH: 201
<212> TYPE: DNA
<213> ORGANISM: Oryza sativa

<400> SEQUENCE: 214

```
gttttggttg ctattaatcg attgagcaag taggggaaat attcctatca tctatgcttc    60
aaataaagtt ttctcttaaa ttactcatcc gatttacaat ycgattacac cgttgtgttc   120
gtaataatta aatctttaca acaagatctc acatgattat attttgatga aaatcacaa   180
attacttta tgatatgtct a                                              201
```

<210> SEQ ID NO 215
<211> LENGTH: 201
<212> TYPE: DNA
<213> ORGANISM: Oryza sativa

<400> SEQUENCE: 215

```
gtcccgcctg gtgacgattt ccatgggcat tgcgccgact gactgtgtcg gcagcatgca    60
tcgtctcggg cgttcaacgt gtggagggga cgacgtataa ragtacacgc gaagactgta   120
ggtagaggtg cttttcccgc gaaaagtggc agtagcggcg gttggacagt aaccttcgtg   180
tatggttgtg tgttcatctc a                                              201
```

<210> SEQ ID NO 216
<211> LENGTH: 201
<212> TYPE: DNA
<213> ORGANISM: Oryza sativa

<400> SEQUENCE: 216

```
tgcttgtgcg ttcactgttc agagaagctg gttatcctcc ctgataagaa cagccgggag      60
gtcagtgtgc tatggttttg tttagttctg gaatgatcca rtcacccagc acaattgact     120
ggctgagtgt tgcattaagc aaatctggac cggatttgag ggaattttct cgcgcagtgg     180
agatctatga taaatctcgt a                                                201
```

<210> SEQ ID NO 217
<211> LENGTH: 201
<212> TYPE: DNA
<213> ORGANISM: Oryza sativa

<400> SEQUENCE: 217

```
ctgcttcgcc aacggcctcg aggcgaggct ggcaggtact ggtagtcaaa tttacaagaa      60
ctacacgata actcggcttc catgcactga tgtgctgaaa rcgtaccagc tttatttggc     120
agcttgccca tttaagaaga tctctcatta ctttgccaat caaacaattt tgaatgctgt     180
ggagaaggcc aagaaagttc a                                                201
```

<210> SEQ ID NO 218
<211> LENGTH: 201
<212> TYPE: DNA
<213> ORGANISM: Oryza sativa

<400> SEQUENCE: 218

```
tcacattctg gttgttgagg gtccactgat acctttacct gttgcagttt attgttttaa      60
ataatccaat caaacttttg tttgagctta ttgctgaata rcacagcagc agtacatgca     120
atgcaagatg cccagatgat gagaataaag gcaatggcaa aaatataagt gctagttcta     180
tttcaaaata acaaacagac a                                                201
```

<210> SEQ ID NO 219
<211> LENGTH: 201
<212> TYPE: DNA
<213> ORGANISM: Oryza sativa

<400> SEQUENCE: 219

```
tatgatgatg cttattatag cctaaggtat gtacttttaa gatttagttc gaagtaatgc      60
ccatctggca agttaattcc agcattaacg tgttctaaaa rccactctac ttatgagaag     120
ccgggccacc acattcatac attacagcca gaaacaacaa atccaggaag ttaatacgtg     180
attaagaatg catcaaacaa g                                                201
```

<210> SEQ ID NO 220
<211> LENGTH: 201
<212> TYPE: DNA
<213> ORGANISM: Oryza sativa

<400> SEQUENCE: 220

```
tcgatatgtt gggtttttc tctttactag tagcatgcca tctagtgtgc atcttacgta       60
gtggaatatt atcgggcacc caatattcgg ctcgcacaaa rctccgagga cgaggaggag    120
gacgactaat ttggcagctc agctcacctg cacggctgca ctgtgctgtg cccggtgggc    180
gaagccattt cacccgcggg c                                                201
```

<210> SEQ ID NO 221
<211> LENGTH: 201
<212> TYPE: DNA

<213> ORGANISM: Oryza sativa

<400> SEQUENCE: 221

| tctgaaaacg catggccgaa ataagatgca agaacacctg caaaataatc tcaggatcag | 60 |
| tccaggtacg cattctctac tgttatctac tgaaccagag rggaaaaaaa caaaaactag | 120 |
| gatgaatgca gtgtcacttt gctgcttgta attctctgaa tttctgaatg aaagaaaaga | 180 |
| aaagaaaaga agcgaaactg g | 201 |

<210> SEQ ID NO 222
<211> LENGTH: 201
<212> TYPE: DNA
<213> ORGANISM: Oryza sativa

<400> SEQUENCE: 222

| cttaaattct catgttttat tcccgttgca acgaacggtc atttcttta gtgtccataa | 60 |
| atagctataa gaggcatcga tcatcgcagc aagccgactg rgtgtggcgc ctacgtgatc | 120 |
| gttggtttgt ttcgcttgtt tgggcataca gctatgagaa ctttgttggg ggcccatact | 180 |
| acttatcatc atgtgtctaa t | 201 |

<210> SEQ ID NO 223
<211> LENGTH: 201
<212> TYPE: DNA
<213> ORGANISM: Oryza sativa

<400> SEQUENCE: 223

| gaactaaaca cacccggaat gtgatggatc cgaatctgct gtagttgata ctgtgaatgt | 60 |
| aacttgtagg cctcatttga ttttctagaa aaaatggag raaaaacata ggaataagaa | 120 |
| tcctatgtga attggtactg ttcatccctt tgatttgtag gaattgaaca aaggaaaagc | 180 |
| atggggaaaa aaatcctatg a | 201 |

<210> SEQ ID NO 224
<211> LENGTH: 201
<212> TYPE: DNA
<213> ORGANISM: Oryza sativa

<400> SEQUENCE: 224

| agcgccacgc cgcggccagc gccgtggtgt tctccgggtg gcatcgcttg agctacatca | 60 |
| ccaccgatgg ccacttaaag tccgttgagc tcgatcgcca ratccggcgg ctccacaggg | 120 |
| ccgtcggcaa cgcggtcgtc gacgacaagt acttggtctt cgggaccggc tccacccacc | 180 |
| tgatcaacgc gctggtgtac g | 201 |

<210> SEQ ID NO 225
<211> LENGTH: 201
<212> TYPE: DNA
<213> ORGANISM: Oryza sativa

<400> SEQUENCE: 225

| acgggcggta ccagctacct gtcacagaca tgtgggccca gcttaacgct aacgcgctga | 60 |
| tggccccaca tggcagcgac ctgcccccctc tgtccctccg ytccacggc gcaccgagcg | 120 |
| tccaccgccc ccgcgatat ccgggggttt aggcgatatt tagccacgag aggggagggg | 180 |
| gagagtagga gaccgacgct t | 201 |

<210> SEQ ID NO 226
<211> LENGTH: 201

```
<212> TYPE: DNA
<213> ORGANISM: Oryza sativa

<400> SEQUENCE: 226
agaaagactt gctttagctt tattgtttct tttccatatt ctatattctt gaaaaggact    60
gcaaagctct tctagtatat gcaattagct gctttggaag rcacttcaaa agggatgaag   120
gaaagaaggc tgtcatatca attactcaat catgaccaga tcatcgatct gatgcagtta   180
aaaatttcat taattttgcc a                                             201

<210> SEQ ID NO 227
<211> LENGTH: 401
<212> TYPE: DNA
<213> ORGANISM: Oryza sativa

<400> SEQUENCE: 227
atcgatgtaa ttagtgatgt caatcaatgg tccagatggc atttggagtc ttcgagcctt    60
atctttagtg tcacttgcat tttcagttcc aaatgaacat ctggaagaag cttggatat   120 ctttggaatt tcattgatag gatgaaaatc tcttgccgca tgaagcctga cggagtttcc   180
gttagccaaa gtggcatcag rtacagcata ttccaaggaa tctgtgtgct tcctatcagg   240
ttttgctgga atggaaaatt gtgctggctc agttttgctg ttcccctac ttttcaataa    300 atcaggttca ccttctttc gcagaccagt tgaattttgt atattctctt tacaagcaga    360
tgctgaagag tggcctaata aattatttgg tgaaacctct a                       401

<210> SEQ ID NO 228
<211> LENGTH: 401
<212> TYPE: DNA
<213> ORGANISM: Oryza sativa

<400> SEQUENCE: 228
taaccttata gtgggacaag gactgaaaag cagttcctct tgctttaacc cagagagggt    60
caacattttt ctccctgtaa gttccaatgc tccacaatat ttgtatcaag tgttttgagg   120
ttccaggata tgcttcagaa tccattgctc cccatctcaa tagaatgcat aagctgaaaa   180
ggcaagaaaa agtggaataa raaatagatt ttctacaagc acatgatcat tggtgggcac   240
tgcccacaga taaaactagc tagctctcgg cagtcttacc catgggaaac agtaggatct   300
atcgaaaaat caagcagctg ctttgatata actttccagg cagtatagaa atctggcaaa   360
gagattagca gctcacctca gaagtgaaat ttggagggca a                       401

<210> SEQ ID NO 229
<211> LENGTH: 398
<212> TYPE: DNA
<213> ORGANISM: Oryza sativa

<400> SEQUENCE: 229
ccaagcggag acatcgcttc catgagcaat tcacggtttt tcactagatc tctcacccctt   60 tctctgatcc attctggacc agcctctaat gcgtagagcg ccaggcgctg cccgatgatg   120
gaagcacaga taggtatgtt atcttgcact ttgagcagct gtgcatgaag accgtcagct   180
tcgtttgggt gggcaatmtg cagcagtcag ctcatcagtt cttgtaagac tcactgatca   240
acacagattg tgcagccact aagttactta tactgcattg ctatggtgat aatttaaggg   300
aatgccctgg taaagattcc aagtggatgc gggaaattca tgaaactgaa agaactcaat   360
attgactctt acatcagcat tttcaagcct aagcagag                           398
```

<210> SEQ ID NO 230
<211> LENGTH: 401
<212> TYPE: DNA
<213> ORGANISM: Oryza sativa

<400> SEQUENCE: 230
tttaaatcaa atcttaaaaa tataaatcat aaataactat caagttgttg agtttaaaaa     60
tataaaaatt atataaatat atttgtcttg aaaaatactt tcataaaagt atacatatat    120 cacttttttaa taaatatttt tataaaaaca agaagtcaaa gttatgtttt agagaccgcg    180
tctctgttct aaacgacttc ytttataagt atggagggag tatccatttc acatatactt    240
atggtcttgt ttacatccca acaaatttta gccaaaaaca tcacatcaaa tatttagcca    300
catgtatagg acattaaata taaaaaaaca attacacagt ttgcatgtaa attgcgagac    360
gaatcttttg agcctaatta cgccattatt tgacaatgtg g                       401

<210> SEQ ID NO 231
<211> LENGTH: 401
<212> TYPE: DNA
<213> ORGANISM: Oryza sativa

<400> SEQUENCE: 231
cggaactatg actaactcct ctccgtaagc ttctttgtaa tatgtattgc tgctgtactt     60
ggtctcatta tctccttaca gatatatata cattttttgc agggtatatc cacttcatct    120
tctccgtgac attgagacta gggtttggct cctggccgtg gagtcagaga gtcagtgtaa    180
agctgacgga gaatatgcac yttccagtgt tactcaaaat ctagctactg aaacaaatac    240
caatattata gaacaaacag ctgatgttat cacaaaaata gacaatagta tgagttcacc    300
acggatgaga ataacagaaa ggaatggtat aagggacaac accaccccat cattccatca    360
acatttgcaa ctctttgagt ctaatggcga aggcgtacat a                       401

<210> SEQ ID NO 232
<211> LENGTH: 375
<212> TYPE: DNA
<213> ORGANISM: Oryza sativa

<400> SEQUENCE: 232
caactactga caacaagtgc catgtctaaa tttctgaaca tgcacacaac acacaaatga     60
tgaatatggt gaaaccgcaa ttagcattag aaagttttaa ctctagaaat caatttccaa    120
gttgtaatcc ccatactccc aacccagaag ggaaaaaaaa caactccaaa acccycaact    180
tttaaaaatg tgggaacaat caaaccatat gcttgagata tacccacaaa gccatcggcg    240
gccgcttaca gcagagtaca ccctcatctt gcacgcctcc gaagaagcag agccgtgat    300 caacacgagc atcttgtcct gctccacccc acacagtgac gagtctaggg cacgacgaag    360
gcgcgctcct aaacc                                                    375

<210> SEQ ID NO 233
<211> LENGTH: 401
<212> TYPE: DNA
<213> ORGANISM: Oryza sativa

<400> SEQUENCE: 233
cttcctgtcg tgagtgactg ggtggtgggc tcaatcggcc tggcccgata cgatgcaagc     60
gcgtggctgg gcaggagatc ggacggtgct gattgttggg gcgacgtggc cgcgtgggcg    120
aatgaatagt gaacagtacc gacgtgaggt ttataggatt ttatatgact aggggtgaac    180

```
gttggataga agggaatgtg ytagtgctgt tctgaacctc ttgcgcatac attaacatgt    240
tttatctaat ctaataaaca tgattaaatt tagcgtttgc ttttacagta gtagaaatat    300
gaaattgaac aatggttagt ctgaggaatc ataagcctat gatctagctg gagtcttctc    360
cggtttaagc taccaattga aacatattaa ttgatgcctg a                       401

<210> SEQ ID NO 234
<211> LENGTH: 401
<212> TYPE: DNA
<213> ORGANISM: Oryza sativa

<400> SEQUENCE: 234
aatgtgctca acttcatata tatgtgtgtt gagcacatag ctcatatata agatcaatgg     60
ttagatcaat ggttttttggg ttagatcaat ggttgagcac atagctcata tatatgtgtg   120
ctcaacggct cacacacaac ttcatatata tgtacccaaa aaagcactat tagatcaatg   180
gttataattg tttcaccacg raatattcaa ctttactcaa tgttttgttt aacaagttcc    240
ttttggtcac ttgccaattt ttctagatca tacagtacaa tctattgatc acaattcaca   300
ttgaataact aggtcaagcc attctgtaca tgcccatgca tgaacttact gtactaatat   360
tatcttagat taatttatcc tgaaacttat agtcatatgt g                       401

<210> SEQ ID NO 235
<211> LENGTH: 201
<212> TYPE: DNA
<213> ORGANISM: Oryza sativa
<220> FEATURE:
<221> NAME/KEY: misc_feature
<222> LOCATION: (102)..(102)
<223> OTHER INFORMATION: May or may not be present

<400> SEQUENCE: 235
gcatgaaagc tgagaccatc accaggttga tcgttgttgc tgctattata agatgccaaa     60
atcggcaaat cggtcattca ctcaaggatt ggacacaaga caaaaaaaaa gtaacaggta    120
gcagactttc aactaacctg gcatgaaagc ttggattgtc actggtttga ttgttgctgc    180
tgctgttatg aaagctgtat a                                             201

<210> SEQ ID NO 236
<211> LENGTH: 201
<212> TYPE: DNA
<213> ORGANISM: Oryza sativa

<400> SEQUENCE: 236
acgttgctta ggtagcacct tgatttaatc aaatgctagc tagttgatgc caggtggcac     60
actgcggacg gatttgtttg tcagtttccc tgcattacac wttgtacagg agtgtactac   120
atccacatac aatgaacagt agtagtagca gcagctatat actccagttg cctagtcgta   180
cacaaagtat aattaatcac a                                             201
```